US012287338B2

(12) United States Patent
Zhai et al.

(10) Patent No.: US 12,287,338 B2
(45) Date of Patent: Apr. 29, 2025

(54) METHOD AND COMPOSITIONS FOR PREDICTING ANTI-CANCER EFFICACY OF COMPOUNDS TARGETING APOPTOSIS PATHWAY

(71) Applicants: Ascentage Pharma (Suzhou) Co., Ltd., Jiangsu (CN); Ascentage Pharma Group Corp Limited, Hong Kong (CN)

(72) Inventors: Yifan Zhai, Jiangsu (CN); Dajun Yang, Jiangsu (CN); Douglas Dong Fang, Jiangsu (CN); Ran Tao, Jiangsu (CN)

(73) Assignees: Ascentage Pharma (Suzhou) Co., Ltd., Jiangsu (CN); Ascentage Pharma Group Corp Limited, Hong Kong (CN)

( * ) Notice: Subject to any disclaimer, the term of this patent is extended or adjusted under 35 U.S.C. 154(b) by 759 days.

(21) Appl. No.: 17/297,188

(22) PCT Filed: Nov. 27, 2020

(86) PCT No.: PCT/CN2020/132191
§ 371 (c)(1),
(2) Date: May 26, 2021

(87) PCT Pub. No.: WO2021/104442
PCT Pub. Date: Jun. 3, 2021

(65) Prior Publication Data
US 2022/0317127 A1    Oct. 6, 2022

(51) Int. Cl.
| | |
|---|---|
| G01N 33/574 | (2006.01) |
| A61K 31/407 | (2006.01) |
| A61K 31/496 | (2006.01) |
| A61K 31/519 | (2006.01) |
| A61P 35/00 | (2006.01) |

(52) U.S. Cl.
CPC ..... *G01N 33/57484* (2013.01); *A61K 31/407* (2013.01); *A61K 31/496* (2013.01); *A61K 31/519* (2013.01); *A61P 35/00* (2018.01)

(58) Field of Classification Search
CPC . G01N 33/57484; A61P 35/00; A61K 31/496; A61K 31/407; A61K 31/519
USPC ....................................................... 514/409
See application file for complete search history.

(56) References Cited

U.S. PATENT DOCUMENTS

| | | | |
|---|---|---|---|
| 9,096,625 B2* | 8/2015 | Wang | A61K 45/06 |
| 9,901,574 B2* | 2/2018 | Warner | A61P 35/00 |
| 2010/0028889 A1* | 2/2010 | Anderson | C12Q 1/6886 |
| | | | 435/6.16 |
| 2014/0272969 A1* | 9/2014 | Sokolova | G01N 33/57419 |
| | | | 435/6.11 |
| 2016/0178612 A1* | 6/2016 | Cardone | G01N 33/5011 |
| | | | 435/7.1 |

FOREIGN PATENT DOCUMENTS

| | | |
|---|---|---|
| CN | 101541977 A | 9/2009 |
| WO | WO-2007133551 A2 | 11/2007 |
| WO | WO-2011068863 A1 | 6/2011 |
| WO | WO-2012154567 A2 | 11/2012 |
| WO | WO-2014113413 A1 | 7/2014 |
| WO | WO-2015161032 A1 | 10/2015 |
| WO | WO-2016172214 A1 | 10/2016 |
| WO | WO-2018027097 A1 | 2/2018 |

OTHER PUBLICATIONS

Starmans MH, Boutros PC. Biomarkers and subtypes of cancer. Aging (Albany NY). May 2015;7(5):280-1. doi: 10.18632/aging.100741. (Year: 2015).*
Merino D, Kelly GL, Lessene G, Wei AH, Roberts AW, Strasser A. BH3-Mimetic Drugs: Blazing the Trail for New Cancer Medicines. Cancer Cell. Dec. 10, 2018;34(6):879-891. doi: 10.1016/j.ccell.2018.11.004. (Year: 2018).*
Gay CM, Tong P, Cardnell RJ, Sen T, Su X, Ma J, Bara RO, Johnson FM, Wakefield C, Heymach JV, Wang J, Byers LA. Differential Sensitivity Analysis for Resistant Malignancies (DISARM) Identifies Common Candidate Therapies across Platinum-Resistant Cancers. Clin Cancer Res. Jan. 1, 2019;25(1):346-357. (Year: 2019).*
Liu Y, Mondello P, Erazo T, Tannan NB, Asgari Z, de Stanchina E, Nanjangud G, Seshan VE, Wang S, Wendel HG, Younes A. Noxa genetic amplification or pharmacologic induction primes lymphoma cells to BCL2 inhibitor-induced cell death. Proc Natl Acad Sci U S A. Nov. 20, 2018;115(47):12034-12039. (Year: 2018).*
Kendall LV, Riley LK. Reverse transcriptase polymerase chain reaction (RT-PCR). Contemp Top Lab Anim Sci. Jan. 2000;39(1):42. PMID: 11178315. (Year: 2000).*
Shen J, Swift B, Mamelok R, Pine S, Sinclair J, Attar M. Design and Conduct Considerations for First-in-Human Trials. Clin Transl Sci. Jan. 2019;12(1):6-19. doi: 10.1111/cts.12582. Epub Aug. 24, 2018. PMID: 30048046; PMCID: PMC6342261. (Year: 2019).*
Augustyn, et al.ASCL1 is a lineage oncogene providing therapeutic targets for high-grade neuroendocrine lung cancers, Proc. Natl. Acad. Sci. USA, 111(41) 14788-14793, https://doi.org/10.1073/pnas.1410419111. (Year: 2014).*
Gay, C. M. et al., Differential Sensitivity Analysis for Resistant Malignancies (DISARM) identifies common candidate therapies across platinum-resistant cancers, Clin Cancer Res, Jan. 2019, 25(1):346-357 (23 total pages).

(Continued)

*Primary Examiner* — Kahsay Habte
(74) *Attorney, Agent, or Firm* — COOLEY LLP; Heidi Erlacher; Xixi Sun

(57) ABSTRACT

Provided are biomarkers for predicting the efficacy of MDM2 inhibitor or Bcl-2/Bcl-xL dual inhibitors or Bcl-2 inhibitor or Bcl-xL inhibitor in treating cancer patients. Also provided are compositions, e.g., kits, for evaluating gene levels of the biomarkers and methods of using such gene levels to predict a cancer patient's response to the MDM2 inhibitors or Bcl-2/Bcl-xL dual inhibitors or Bcl-2 inhibitor or Bcl-xL inhibitor. Such information can be used in determining prognosis and treatment options for cancer patients.

12 Claims, 15 Drawing Sheets
Specification includes a Sequence Listing.

(56) References Cited

OTHER PUBLICATIONS

Olejniczak, E. T. et al., "Integrative Genomic Analysis of Small-Cell Lung Carcinoma Reveals Correlates of Sensitivity to Bcl-2 Antagonists and Uncovers Novel Chromosomal Gains," Mol Cancer Res, 5(4):331-339 (Apr. 2007).

* cited by examiner

DNA coding sequences and protein (amino acids) sequences of biomarkers with SEQ
ID numbers mentioned in the present disclosure.

1. Bcl-2α

Nucleotide Sequence (720 nt): (SEQ ID No: 2)
ATGGCGCACGCTGGGAGAACAGGGTACGATAACCGGGAGATAGTGATGAAGTACATCCATTATAAGCTGT
CGCAGAGGGGCTACGAGTGGGATGCGGGAGATGTGGGCGCCGCGCCCCGGGGGCCGCCCCCGCACCGGGCATCT
TCTCCTCCCAGCCCGGGCACACGCCCCATCCAGCCGCATCCCGGGACCCGGTCGCCAGGACCTCGCCGCTGCAGACC
CCGGCTGCCCCGGCGCCGCCGCGGGGCCTGCGCTCAGCCCGGTGCCACCTGTGGTCCACCTGACCCTCCGCCAGGC
CGGCGACGACTTCTCCCGCCGCTACCGCCGCGACTTCGCCGAGATGTCCAG
CCAGCTGCACCTGACGCCCTTCACCGCGCGGGGACGCTTTGCCACGGTGGTGGAGGAGCTCTTCAGGGAC
GGGGTGAACTGGGGGAGGATTGTGGCCTTCTTTGAGTTCGGTGGGGTCATGTGTGTGGAGAGCGTCAACC
GGGAGATGTCGCCCCTGGTGGACAACATCGCCCTGTGGATGACTGAGTACCTGAACCGGCACCTGCACAC
CTGGATCCAGGATAACGGAGGCTGGGATGCCTTTGTGGAACTGTACGGCCCCAGCATGCGGCCTCTGTTT
GATTTCTCCTGGCTGTCTCTGAAGACTCTGCTCAGTTTGGCCCTGGTGGGAGCTTGCATCACCCTGGGTG
CCTATCTGGGCCACAAGTGA

Protein Sequence (239 aa): (SEQ ID No: 1)
MAHAGRTGYDNREIVMKYIHYKLSQRGYEWDAGDVGAAPPGAAPAPGIFSSQPGHTPHPAASRDPVARTS
PLQTPAAPGAAAGPALSPVPPVVHLTLRQAGDDFSRRYRRDFAEMSSQLHLTPFTARGRFATVVEELFRD
GVNWGRIVAFFEFGGVMCVESVNREMSPLVDNIALWMTEYLNRHLHTWIQDNGGWDAFVELYGPSMRPLF
DFSWLSLKTLLSLALVGACITLGAYLGHK

2. Bcl-2 β :

Nucleotide Sequence (618 nt): (SEQ ID No: 14)
ATGGCGCACGCTGGGAGAACAGGGTACGATAACCGGGAGATAGTGATGAAGTACATCCATTATAAGCTGT
CGCAGAGGGGCTACGAGTGGGATGCGGGAGATGTGGGCGCCGCGCCCCGGGGGCCGCCCCCGCACCGGGCATCT
TCTCCTCCCAGCCCGGGCACACGCCCCATCCAGCCGCATCCCGGGACCCGGTCGCCAGGACCTCGCCGCTGCAGACC
CCGGCTGCCCCGGCGCCGCCGCGGGGCCTGCGCTCAGCCCGGTGCCACCTGTGGTCCACCTGACCCTCCGCCAGGC
CGGCGACGACTTCTCCCGCCGCTACCGCCGCGACTTCGCCGAGATGTCCAG
CCAGCTGCACCTGACGCCCTTCACCGCGCGGGGACGCTTTGCCACGGTGGTGGAGGAGCTCTTCAGGGAC
GGGGTGAACTGGGGGAGGATTGTGGCCTTCTTTGAGTTCGGTGGGGTCATGTGTGTGGAGAGCGTCAACC
GGGAGATGTCGCCCCTGGTGGACAACATCGCCCTGTGGATGACTGAGTACCTGAACCGGCACCTGCACAC
CTGGATCCAGGATAACGGAGGCTGGGTAGGTGCACTTGGTGATGTGAGTCTGGGCTGA

Protein Sequence (205 aa): (SEQ ID No: 13)
MAHAGRTGYDNREIVMKYIHYKLSQRGYEWDAGDVGAAPPGAAPAPGIFSSQPGHTPHPAASRDPVARTS
PLQTPAAPGAAAGPALSPVPPVVHLTLRQAGDDFSRRYRRDFAEMSSQLHLTPFTARGRFATVVEELFRD
GVNWGRIVAFFEFGGVMCVESVNREMSPLVDNIALWMTEYLNRHLHTWIQDNGGWVGALGDVSLG

FIG 6

3. Bcl-xL (one of Bcl-xL 8 isoforms):

Nucleotide Sequence (702 nt): (SEQ ID No: 4)
ATGTCTCAGAGCAACCGGGAGCTGGTGGTTGACTTTCTCTCCTACAAGCTTTCCCAGAAAGGATACAGCT
GGAGTCAGTTTAGTGATGTGGAAGAGAACAGGACTGAGGCCCCAGAAGGGACTGAATCGGAGATGGAGACCCCCA
GTGCCATCAATGGCAACCCATCCTGGCACCTGGCAGACAGCCCCGCGGTGAATGGAGCCACTGGC
CACAGCAGCAGTTTGGATGCCCGGGAGGTGATCCCCATGGCAGCAGTAAAGCAAGCGCTGAGGGAGGCAGGCGAC
GAGTTTGAACTGCGGTACCGGCGGGCATTCAGTGACCTGACATCCCAGCTCCACATCACCCCAGG
GACAGCATATCAGAGCTTTGAACAGGTAGTGAATGAACTCTTCCGGGATGGGGTAAACTGGGGTCGCATT
GTGGCCTTTTTCTCCTTCGGCGGGGCACTGTGCGTGGAAAGCGTAGACAAGGAGATGCAGGTATTGGTGA
GTCGGATCGCAGCTTGGATGGCCACTTACCTGAATGACCACCTAGAGCCTTGGATCCAGGAGAACGGCGG
CTGGGATACTTTTGTGGAACTCTATGGGAACAATGCAGCAGCCGAGAGCCGAAAGGGCCAGGAACGCTTC
AACCGCTGGTTCCTGACGGGCATGACTGTGGCCGGCGTGGTTCTGCTGGGCTCACTCTTCAGTCGGAAAT
GA

Protein Sequence (233 aa): (SEQ ID No: 3)
MSQSNRELVVDFLSYKLSQKGYSWSQFSDVEENRTEAPEGTESEMETPSAINGNPSWHLADSPAVNGATG
HSSSLDAREVIPMAAVKQALREAGDEFELRYRRAFSDLTSQLHITPGTAYQSFEQVVNELFRDGVNWGRI
VAFFSFGGALCVESVDKEMQVLVSRIAAWMATYLNDHLEPWIQENGGWDTFVELYGNNAAAESRKGQERF
NRWFLTGMTVAGVVLLGSLFSRK

4. BimEL (one of BIM 16 isoforms)

Nucleotide Sequence (597 nt): (SEQ ID NO: 6)
ATGGCAAAGCAACCTTCTGATGTAAGTTCTGAGTGTGACCGAGAAGGTAGACAATTGCAGCCTGCGGAGA
GGCCTCCCCAGCTCAGACCTGGGGCCCCTACCTCCCTACAGACAGAGCCACAAGGTAATCCTGAAGGCAA
TCACGGAGGTGAAGGGGACAGCTGCCCCACGGCAGCCCTCAGGGCCCGCTGGCCCCACCTGCCAGCCCT
GGCCCTTTTGCTACCAGATCCCCGCTTTTCATCTTTATGAGAAGATCCTCCCTGCTGTCTCGATCCTCCA
GTGGGTATTTCTCTTTTGACACAGACAGGAGCCCAGCACCCATGAGTTGTGACAAATCAACACAAACCCC
AAGTCCTCCTTGCCAGGCCTTCAACCACTATCTCAGTGCAATGGCTTCCATGAGGCAGGCTGAACCTGCA
GATATGCGCCCAGAGATATGGATCGCCCAAGAGTTGCGGCGTATTGGAGACGAGTTTAACGCTTACTATG
CAAGGAGGGTATTTTTGAATAATTACCAAGCAGCCGAAGACCACCCACGAATGGTTATCTTACGACTGTT
ACGTTACATTGTCCGCCTGGTGTGGAGAATGCATTGA

Protein Sequence (198 aa): (SEQ ID No: 5)
MAKQPSDVSSECDREGRQLQPAERPPQLRPGAPTSLQTEPQGNPEGNHGGEGDSCPHGSPQGPLAPPASP
GPFATRSPLFIFMRRSSLLSRSSSGYFSFDTDRSPAPMSCDKSTQTPSPPCQAFNHYLSAMASMRQAEPA
DMRPEIWIAQELRRIGDEFNAYYARRVFLNNYQAAEDHPRMVILRLLRYIVRLVWRMH

FIG 6 (Continued)

5. BimL (one of BIM 16 isoforms)

Nucleotide Sequence (417 nt): (SEQ ID NO: 16)
ATGGCAAAGCAACCTTCTGATGTAAGTTCTGAGTGTGACCGAGAAGGTAGACAATTGCAGCCTGCGGAGA
GGCCTCCCCAGCTCAGACCTGGGGCCCCTACCTCCCTACAGACAGAGCCACAAGACAGGAGCCCAGCACC
CATGAGTTGTGACAAATCAACACAAACCCCAAGTCCTCCTTGCCAGGCCTTCAACCACTATCTCAGTGCA
ATGGCTTCCATGAGGCAGGCTGAACCTGCAGATATGCGCCCAGAGATATGGATCGCCCAAGAGTTGCGGC
GTATTGGAGACGAGTTTAACGCTTACTATGCAAGGAGGGTATTTTTGAATAATTACCAAGCAGCCGAAGA
CCACCCACGAATGGTTATCTTACGACTGTTACGTTACATTGTCCGCCTGGTGTGGAGAATGCATTGA

Protein Sequence (138 aa): (SEQ ID No: 15)
MAKQPSDVSSECDREGRQLQPAERPPQLRPGAPTSLQTEPQDRSPAPMSCDKSTQTPSPPCQAFNHYLSA
MASMRQAEPADMRPEIWIAQELRRIGDEFNAYYARRVFLNNYQAAEDHPRMVILRLLRYIVRLVWRMH

6. PUMA (PUMA-gamma)

Nucleotide Sequence (786 nt): (SEQ ID NO: 10)
ATGAAATTTGGCATGGGGTCTGCCCAGGCATGTCCATGCCAGGTGCCCAGGGCTGCTTCCACGACGTGGG
TCCCCTGCCAGATTTGTGGCCCCAGGGAGCGCCATGGCCCGCGCACGCCAGGAGGGCAGCTCCCCGGAGC
CCGTAGAGGGCCTGGCCCGCGACGGCCCGCGCCCCTTCCCGCTCGGCCGCCTGGTGCCCTCGGCAGTGTC
CTGCGGCCTCTGCGAGCCCGGCCTGGCTGCCGCCCCCGCCGCCCCCACCCTGCTGCCCGCTGCCTACCTC
TGCGCCCCCACCGCCCCACCCGCCGTCACCGCCGCCCTGGGGGGTTCCCGCTGGCCTGGGGGTCCCCGCA
GCCGGCCCCGAGGCCCGCGCCCGGACGGTCCTCAGCCCTCGCTCTCGCTGGCGGAGCAGCACCTGGAGTC
GCCCGTGCCCAGCGCCCCGGGGGCTCTGGCGGGCGGTCCCACCCAGGCGGCCCCGGGAGTCCGCGGGGAGGAGG
AACAGTGGGCCCGGGAGATCGGGGCCCAGCTGCGGCGGATGGCGGACGACCTCAACGCACAGTACGAGCGGCGGA
GACAAGAGGAGCAGCAGCGGCACCGCCCCTCACCCTGGAGGGTCCTGTACAATCTCATCATGGGACTCCTGCCCTTA
CCCAGGGGCCACAGAGCCCCCGAGATGGAGCCCAATTAGGTGCCTGCACCCGCCCGGTGGACGTCAGGGACTCGGG
GGGCAGGCCCCTCCCACCTCCTGACACCCTGGCCAGCGCGGGGGACTTTCTCTGCACCATGTAG

Protein Sequence (261 aa): (SEQ ID No: 9)
MKFGMGSAQACPCQVPRAASTTWVPCQICGPRERHGPRTPGGQLPGARRGPGPRRPAPLPARPPGALGSV
LRPLRARPGCRPRRPHPAARCLPLRPHRPTRRHRRPGGFPLAWGSPQPAPRPAPGRSSALALAGGAAPGV
ARAQRPGGSGGRSHPGGPGSPRGGGTVGPGDRGPAAADGGRPQRTVRAAETRGAAAAPPLTLEGPVQSHH
GTPALTQGPQSPRDGAQLGACTRPVDVRDSGGRPLPPPDTLASAGDFLCTM

FIG 6 (Continued)

7. Mcl-1（Mcl-1ES）

Nucleotide Sequence (594 nt): (SEQ ID No: 12)
ATGTTTGGCCTCAAAAGAAACGCGGTAATCGGACTCAACCTCTACTGTGGGGGGGCCGGCTTGGGGGCCG
GCAGCGGCGGCGCCACCCGCCCGGGAGGGCGACTTTTGGCCACCGGCGCCAAGGACACAAAGCCAATGGGCAGGT
CTGGGGCCACCAGCAGGAAGGCGCTGGAGACCTTACGACGGGTTGGGGATGGCGTGCAGCGCAACCACGAGACGG
CCTTCCAAGGCATGCTTCGGAAACTGGACATCAAAAACGAAGACGATGTGAAATCGTTGTCTCGAGTGATGATCCATG
TTTTCAGCGACGGCGTAACAAACTGGGGCAGGATTGTGACTCTCATTTCTTT
TGGTGCCTTTGTGGCTAAACACTTGAAGACCATAAACCAAGAAAGCTGCATCGAACCATTAGCAGAAAGT
ATCACAGACGTTCTCGTAAGGACAAAACGGGACTGGCTAGTTAAACAAAGAGGCTGGGATGGGTTTGTGG
AGTTCTTCCATGTAGAGGACCTAGAAGGTGGCATCAGGAATGTGCTGCTGGCTTTTGCAGGTGTTGCTGG
AGTAGGAGCTGGTTTGGCATATCTAATAAGATAG

Protein Sequence (197 aa): (SEQ ID No: 11)
MFGLKRNAVIGLNLYCGGAGLGAGSGGATRPGGRLLATGAKDTKPMGRSGATSRKALETLRRVGDGVQRN
HETAFQGMLRKLDIKNEDDVKSLSRVMIHVFSDGVTNWGRIVTLISFGAFVAKHLKTINQESCIEPLAES
ITDVLVRTKRDWLVKQRGWDGFVEFFHVEDLEGGIRNVLLAFAGVAGVGAGLAYLIR

FIG 6 (Continued)

8. Mcl-1L (long)

Nucleotide Sequence (1053 nt): (SEQ ID No: 18)
ATGTTTGGCCTCAAAAGAAACGCGGTAATCGGACTCAACCTCTACTGTGGGGGGGCCGGCTTGGGGGCCG
GCAGCGGCGGCGCCACCCGCCCGGGAGGGCGACTTTTGGCTACGGAGAAGGAGGCCTCGGCCCGGCGAGAGATAG
GGGGAGGGGAGGCCGGCGCGGTGATTGGCGGAAGCGCCGGCGCAAGCCCCCCGTCCACCCTCACGCCAGACTCCC
GGAGGGTCGCGCGGCCGCCGCCCATTGGCGCCGAGGTCCCCGACGTCACCGCGACCCCCGCGAGGCTGCTTTTCTT
CGCGCCCACCCGCCGCGCGGCGCCGCTTGAGGAGATGGAAGCCCCGGCCGCTGACGCCATCATGTCGCCCGAAGAG
GAGCTGGACGGGTACGAGCCGGAGCCTCTCGGGAAGCGGCCGGCTGTCCTGCCGCTGCTGGAGTTGGTCGGGGAA
TCTGGTAATAACACCAGTACGGACGGGTCACTACCCTCGACGCCGCCGCCAGCAGAGGAGGAGGAGGACGAGTTGT
ACCGGCAGTCGCTGGAGATTATCTCTCGGTACCTTCGGGAGCAGGCCACCGGCGCCAAGGACACAAAGCCAATGGG
CAGGTCTGGGGCCACCAGCAGGAAGGCGCTGGAGACCTTACGACGGGTTGGGGATGGCGTGCAGCGCAACCACGA
GACGGCCTTCCAAGGCATGCTTCGGAAACTGGACATCAAAAACGAAGACGATGTGAAATCGTTGTCTCGAGTGATGA
TCCATGTTTTCAGCGACGGCGTAACAAACTGGGGCAGGATTGTGACTCTCATTTCTTTTGGTGCCTTTGTGGCTAAACA
CTTGAAGACCATAAACCAAGAAAGCTGCATCGAACCATTAGCAGAAAGTATCACAGACGTTCTCGTAAGGACAAAAC
GGGACTGGCTAGTTAAACAAAGAGGCTGGGATGGGTTTGTGGAGTTCTTCCATGTAGAGGACCTAGAAGGTGG
CATCAGGAATGTGCTGCTGGCTTTTGCAGGTGTTGCTGGAGTAGGAGCTGGTTTGGCATATCTAATAAGATAG

Protein Sequence (350 aa): (SEQ ID No: 17)
MFGLKRNAVIGLNLYCGGAGLGAGSGGATRPGGRLLATEKEASARREIGGGEAGAVIGGSAGASPPSTLT
PDSRRVARPPPIGAEVPDVTATPARLLFFAPTRRAAPLEEMEAPAADAIMSPEEELDGYEPEPLGKRPAV
LPLLELVGESGNNTSTDGSLPSTPPPAEEEEDELYRQSLEIISRYLREQATGAKDTKPMGRSGATSRKAL
ETLRRVGDGVQRNHETAFQGMLRKLDIKNEDDVKSLSRVMIHVFSDGVTNWGRIVTLISFGAFVAKHLKT
INQESCIEPLAESITDVLVRTKRDWLVKQRGWDGFVEFFHVEDLEGGIRNVLLAFAGVAGVGAGLAYLIR

9. Mcl-1S (short)

Nucleotide Sequence (816 nt): (SEQ ID No: 20)
ATGTTTGGCCTCAAAAGAAACGCGGTAATCGGACTCAACCTCTACTGTGGGGGGGCCGGCTTGGGGGCCG
GCAGCGGCGGCGCCACCCGCCCGGGAGGGCGACTTTTGGCTACGGAGAAGGAGGCCTCGGCCCGGCGAGAGATAG
GGGGAGGGGAGGCCGGCGCGGTGATTGGCGGAAGCGCCGGCGCAAGCCCCCCGTCCACCCTCACGCCAGACTCCC
GGAGGGTCGCGCGGCCGCCGCCCATTGGCGCCGAGGTCCCCGACGTCACCGCGACCCCCGCGAGGCTGCTTTTCTT
CGCGCCCACCCGCCGCGCGGCGCCGCTTGAGGAGATGGAAGCCCCGGCCGCTGACGCCATCATGTCGCCCGAAGAG
GAGCTGGACGGGTACGAGCCGGAGCCTCTCGGGAAGCGGCCGGCTGTCCTGCCGCTGCTGGAGTTGGTCGGGGAA
TCTGGTAATAACACCAGTACGGACGGGTCACTACCCTCGACGCCGCCGCCAGCAGAGGAGGAGGAGGACGAGTTGT
ACCGGCAGTCGCTGGAGATTATCTCTCGGTACCTTCGGGAGCAGGCCACCGGCGCCAAGGACACAAAGCCAATGGG
CAGGTCTGGGGCCACCAGCAGGAAGGCGCTGGAGACCTTACGACGGGTTGGGGATGGCGTGCAGCGCAACCACGA
GACGGCCTTCCAAGGATGGGTTTGTGGAGTTCTTCCATGTAGAGGACCTAGAAGGTGGCATCAGGAATGTGCTGCTG
GCTTTTGCAGGTGTTGCTGGAGTAGGAGCTGGTTTGGCATATCTAATAAGATAGCCTTACTGTAA

Protein Sequence (271 aa): (SEQ ID No: 19)
MFGLKRNAVIGLNLYCGGAGLGAGSGGATRPGGRLLATEKEASARREIGGGEAGAVIGGSAGASPPSTLT
PDSRRVARPPPIGAEVPDVTATPARLLFFAPTRRAAPLEEMEAPAADAIMSPEEELDGYEPEPLGKRPAV
LPLLELVGESGNNTSTDGSLPSTPPPAEEEEDELYRQSLEIISRYLREQATGAKDTKPMGRSGATSRKAL
ETLRRVGDGVQRNHETAFQGWVCGVLPCRGPRRWHQECAAGFCRCCWSRSWFGISNKIALL

FIG 6 (Continued)

10.  Noxa

[Homo sapiens]Noxa CDS(DNA coding sequence)(165nt) (SEQ ID NO: 8)
ATGCCTGGGAAGAAGGCGCGCAAGAACGCTCAACCGAGCCCCGCGCGGGCTCCA
GCAGAGCTGGAAGTCGAGTGTGCTACTCAACTCAGGAGATTTGGAGACAAACTG
AACTTCCGGCAGAAACTTCTGAATCTGATATCCAAACTCTTCTGCTCAGGAACCT
GA

[Homo sapiens] Noxa protein sequence(54aa) (SEQ ID NO: 7)
MPGKKARKNAQPSPARAPAELEVECATQLRRFGDKLNFRQKLLNLISKLFCSGT

11.  ASCL 1

[Homo sapiens]ASCL1 CDS(DNA coding sequence)(711nt) (SEQ ID NO: 22)
ATGGAAAGCTCTGCCAAGATGGAGAGCGGCGGCGCCGGCCAGCAGCCCCAGCCGCAGCCCCAGCA
GCCCTTCCTGCCGCCCGCAGCCTGTTTCTTTGCCACGGCCGCAGCCGCGGCGGCCGCAGCCGCCGCA
GCGGCAGCGCAGAGCGCGCAGCAGCAGCAGCAGCAGCAGCAGCAGCAGCAGGCGCCGCAGC
TGAGACCGGCGGCCGACGGCCAGCCCTCAGGGGGCGGTCACAAGTCAGCGCCCAAGCAAGTCAAG
CGACAGCGCTCGTCTTCGCCCGAACTGATGCGCTGCAAACGCCGGCTCAACTTCAGCGGCTTTGGCT
ACAGCCTGCCGCAGCAGCAGCCGGCCGCCGTGGCGCGCCGCAACGAGCGCGAGCGCAACCGCGTC
AAGTTGGTCAACCTGGGCTTTGCCACCCTTCGGGAGCACGTCCCCAACGGCGCGGCCAACAAGAAG
ATGAGTAAGGTGGAGACACTGCGCTCGGCGGTCGAGTACATCCGCGCGCTGCAGCAGCTGCTGGAC
GAGCATGACGCGGTGAGCGCCGCCTTCCAGGCAGGCGTCCTGTCGCCCACCATCTCCCCCAACTACT
CCAACGACTTGAACTCCATGGCCGGCTCGCCGGTCTCATCCTACTCGTCGGACGAGGGCTCTTACGA
CCCGCTCAGCCCCGAGGAGCAGGAGCTTCTCGACTTCACCAACTGGTTCTGA

[Homo sapiens] ASCL1 protein sequence(236aa) (SEQ ID NO: 21)
MESSAKMESGGAGQQPQPQPQQPFLPPAACFFATAAAAAAAAAAAAAQSAQQQQQQQQQQQA
PQLRPAADGQPSGGGHKSAPKQVKRQRSSSPELMRCKRRLNFSGFGYSLPQQQPAAVARRNERERNR
VKLVNLGFATLREHVPNGAANKKMSKVETLRSAVEYIRALQQLLDEHDAVSAAFQAGVLSPTISPNYSND
LNSMAGSPVSSYSSDEGSYDPLSPEEQELLDFTNWF

FIG 6 (Continued)

SEQUENCE LISTING

```
<160> NUMBER OF SEQ ID NOS: 22

<210> SEQ ID NO 1
<211> LENGTH: 239
<212> TYPE: PRT
<213> ORGANISM: Homo sapiens

<400> SEQUENCE: 1

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110
```

```
Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
                180                 185                 190

Gly Gly Trp Asp Ala Phe Val Glu Leu Tyr Gly Pro Ser Met Arg Pro
            195                 200                 205

Leu Phe Asp Phe Ser Trp Leu Ser Leu Lys Thr Leu Leu Ser Leu Ala
        210                 215                 220

Leu Val Gly Ala Cys Ile Thr Leu Gly Ala Tyr Leu Gly His Lys
225                 230                 235

<210> SEQ ID NO 2
<211> LENGTH: 720
<212> TYPE: DNA
<213> ORGANISM: Homo sapiens

<400> SEQUENCE: 2
atggcgcacg ctgggagaac agggtacgat aaccgggaga tagtgatgaa gtacatccat      60
tataagctgt cgcagagggg ctacgagtgg gatgcgggag atgtgggcgc cgcgcccccg     120
ggggccgccc ccgcaccggg catcttctcc tcccagcccg gcacacgcc  ccatccagcc     180 gcatcccggg accggtcgc  caggacctcg ccgctgcaga ccccggctgc ccccggcgcc     240 gccgcgggc  ctgcgctcag cccggtgcca cctgtggtcc acctgaccct ccgccaggcc     300
ggcgacgact ctctcccgccg ctaccgccgc gacttcgccg agatgtccag ccagctgcac     360
ctgacgccct tcaccgcgcg gggacgcttt gccacggtgg tggaggagct cttcagggac     420
ggggtgaact gggggaggat tgtggccttc tttgagttcg gtggggtcat gtgtgtggag     480
agcgtcaacc gggagatgtc gcccctggtg acaacatcg  ccctgtggat gactgagtac     540
ctgaaccggc acctgcacac ctggatccag gataacggag ctgggatgc  ctttgtggaa     600 ctgtacggcc ccagcatgcg gcctctgttt gatttctcct ggctgtctct gaagactctg     660
ctcagtttgg ccctggtggg agcttgcatc accctgggtg cctatctggg ccacaagtga     720

<210> SEQ ID NO 3
<211> LENGTH: 233
<212> TYPE: PRT
<213> ORGANISM: Homo sapiens

<400> SEQUENCE: 3

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80
```

```
Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 4
<211> LENGTH: 702
<212> TYPE: DNA
<213> ORGANISM: Homo sapiens

<400> SEQUENCE: 4
atgtctcaga gcaaccggga gctggtggtt gactttctct cctacaagct ttcccagaaa    60
ggatacagct ggagtcagtt tagtgatgtg aagagaaca ggactgaggc cccagaaggg   120
actgaatcgg agatggagac ccccagtgcc atcaatggca acccatcctg gcacctggca   180
gacagccccg cggtgaatgg agccactggc cacagcagca gtttggatgc ccggaggtg    240 atccccatgg cagcagtaaa gcaagcgctg agggaggcag gcgacgagtt tgaactgcgg   300
taccggcggg cattcagtga cctgacatcc cagctccaca tcaccccagg acagcatat    360 cagagctttg aacaggtagt gaatgaactc ttccgggatg gggtaaactg gggtcgcatt   420
gtggcctttt tctccttcgg cggggcactg tgcgtggaaa gcgtagacaa ggagatgcag   480
gtattggtga gtcggatcgc agcttggatg gccacttacc tgaatgacca cctagagcct   540
tggatccagg agaacggcgg ctgggatact tttgtggaac tctatgggaa caatgcagca   600
gccgagagcc gaaagggcca ggaacgcttc aaccgctggt tcctgacggg catgactgtg   660
gccggcgtgg ttctgctggg ctcactcttc agtcggaaat ga                      702

<210> SEQ ID NO 5
<211> LENGTH: 198
<212> TYPE: PRT
<213> ORGANISM: Homo sapiens

<400> SEQUENCE: 5

Met Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Glu Gly Asn His
        35                  40                  45
```

```
Gly Gly Glu Gly Asp Ser Cys Pro His Gly Ser Pro Gln Gly Pro Leu
         50                  55                  60
Ala Pro Pro Ala Ser Pro Gly Pro Phe Ala Thr Arg Ser Pro Leu Phe
 65                  70                  75                  80
Ile Phe Met Arg Arg Ser Ser Leu Leu Ser Arg Ser Ser Gly Tyr
                 85                  90                  95
Phe Ser Phe Asp Thr Asp Arg Ser Pro Ala Pro Met Ser Cys Asp Lys
                100                 105                 110
Ser Thr Gln Thr Pro Ser Pro Pro Cys Gln Ala Phe Asn His Tyr Leu
            115                 120                 125
Ser Ala Met Ala Ser Met Arg Gln Ala Glu Pro Ala Asp Met Arg Pro
        130                 135                 140
Glu Ile Trp Ile Ala Gln Glu Leu Arg Arg Ile Gly Asp Glu Phe Asn
145                 150                 155                 160
Ala Tyr Tyr Ala Arg Arg Val Phe Leu Asn Asn Tyr Gln Ala Ala Glu
                165                 170                 175
Asp His Pro Arg Met Val Ile Leu Arg Leu Leu Arg Tyr Ile Val Arg
            180                 185                 190
Leu Val Trp Arg Met His
            195

<210> SEQ ID NO 6
<211> LENGTH: 597
<212> TYPE: DNA
<213> ORGANISM: Homo sapiens

<400> SEQUENCE: 6
atggcaaagc aaccttctga tgtaagttct gagtgtgacc gagaaggtag acaattgcag      60
cctgcggaga ggcctcccca gctcagacct ggggcccccta cctccctaca gacagagcca    120
caaggtaatc ctgaaggcaa tcacggaggt gaaggggaca gctgccccca cggcagccct    180
cagggcccgc tggccccacc tgccagccct ggccttttg ctaccagatc cccgcttttc     240
atctttatga agatcctc cctgctgtct cgatcctcca gtgggtattt ctcttttgac       300
acagacagga gcccagcacc catgagttgt gacaaatcaa cacaaacccc aagtcctcct    360
tgccaggcct tcaaccacta tctcagtgca atggcttcca tgaggcaggc tgaacctgca    420
gatatgcgcc cagagatatg gatcgcccaa gagttgcggc gtattggaga cgagtttaac    480
gcttactatg caaggagggt attttgaat aattaccaag cagccgaaga ccacccacga    540
atggttatct tacgactgtt acgttacatt gtccgcctgg tgtggagaat gcattga      597

<210> SEQ ID NO 7
<211> LENGTH: 54
<212> TYPE: PRT
<213> ORGANISM: Homo sapiens

<400> SEQUENCE: 7

Met Pro Gly Lys Lys Ala Arg Lys Asn Ala Gln Pro Ser Pro Ala Arg
 1               5                  10                  15
Ala Pro Ala Glu Leu Glu Val Glu Cys Ala Thr Gln Leu Arg Arg Phe
             20                  25                  30
Gly Asp Lys Leu Asn Phe Arg Gln Lys Leu Leu Asn Leu Ile Ser Lys
         35                  40                  45
Leu Phe Cys Ser Gly Thr
     50
```

<210> SEQ ID NO 8
<211> LENGTH: 165
<212> TYPE: DNA
<213> ORGANISM: Homo sapiens

<400> SEQUENCE: 8
atgcctggga agaaggcgcg caagaacgct caaccgagcc ccgcgcgggc tccagcagag    60
ctggaagtcg agtgtgctac tcaactcagg agatttggag acaaactgaa cttccggcag   120
aaacttctga atctgatatc caaactcttc tgctcaggaa cctga                    165

<210> SEQ ID NO 9
<211> LENGTH: 261
<212> TYPE: PRT
<213> ORGANISM: Homo sapiens

<400> SEQUENCE: 9

Met Lys Phe Gly Met Gly Ser Ala Gln Ala Cys Pro Cys Gln Val Pro
1               5                   10                  15

Arg Ala Ala Ser Thr Thr Trp Val Pro Cys Gln Ile Cys Gly Pro Arg
            20                  25                  30

Glu Arg His Gly Pro Arg Thr Pro Gly Gly Gln Leu Pro Gly Ala Arg
        35                  40                  45

Arg Gly Pro Gly Pro Arg Arg Pro Ala Pro Leu Pro Ala Arg Pro Pro
    50                  55                  60

Gly Ala Leu Gly Ser Val Leu Arg Pro Leu Arg Ala Arg Pro Gly Cys
65                  70                  75                  80

Arg Pro Arg Arg Pro His Pro Ala Ala Arg Cys Leu Pro Leu Arg Pro
                85                  90                  95

His Arg Pro Thr Arg Arg His Arg Arg Pro Gly Gly Phe Pro Leu Ala
            100                 105                 110

Trp Gly Ser Pro Gln Pro Ala Pro Arg Pro Ala Pro Gly Arg Ser Ser
        115                 120                 125

Ala Leu Ala Leu Ala Gly Gly Ala Pro Gly Val Ala Arg Ala Gln
    130                 135                 140

Arg Pro Gly Gly Ser Gly Gly Arg Ser His Pro Gly Gly Pro Gly Ser
145                 150                 155                 160

Pro Arg Gly Gly Gly Thr Val Gly Pro Gly Asp Arg Gly Pro Ala Ala
                165                 170                 175

Ala Asp Gly Gly Arg Pro Gln Arg Thr Val Arg Ala Ala Glu Thr Arg
            180                 185                 190

Gly Ala Ala Ala Pro Pro Leu Thr Leu Glu Gly Pro Val Gln Ser
        195                 200                 205

His His Gly Thr Pro Ala Leu Thr Gln Gly Pro Gln Ser Pro Arg Asp
    210                 215                 220

Gly Ala Gln Leu Gly Ala Cys Thr Arg Pro Val Asp Val Arg Asp Ser
225                 230                 235                 240

Gly Gly Arg Pro Leu Pro Pro Asp Thr Leu Ala Ser Ala Gly Asp
                245                 250                 255

Phe Leu Cys Thr Met
            260

<210> SEQ ID NO 10
<211> LENGTH: 786
<212> TYPE: DNA
<213> ORGANISM: Homo sapiens

<400> SEQUENCE: 10

```
atgaaatttg gcatggggtc tgcccaggca tgtccatgcc aggtgcccag ggctgcttcc      60
acgacgtggg tccctgcca gatttgtggc cccagggagc gccatggccc gcgcacgcca     120
ggagggcagc tccccggagc ccgtagaggg cctggcccgc gacggcccgc gccccttccc     180
gctcggccgc ctggtgccct cggcagtgtc ctgcggcctc tgcgagcccg gcctggctgc     240
cgcccccgcc gccccacccc tgctgccgc tgcctacctc tgcgcccca ccgcccacc       300
cgccgtcacc gccgccctgg ggggttcccg ctggcctggg ggtccccgca gccggccccg     360
aggcccgcgc ccggacggtc ctcagccctc gctctcgctg gcggagcagc acctggagtc     420
gcccgtgccc agcgccccgg gggctctggc gggcggtccc acccaggcgg ccccgggagt     480
ccgcggggag gaggaacagt gggcccggga gatcggggcc cagctgcggc ggatggcgga     540
cgacctcaac gcacagtacg agcggcggag acaagaggag cagcagcggc accgcccctc     600
accctggagg gtcctgtaca atctcatcat gggactcctg cccttaccca ggggccacag     660
agcccccgag atggagccca attaggtgcc tgcacccgcc cggtgacgt cagggactcg      720
gggggcaggc ccctcccacc tcctgacacc ctggccagcg cggggactt tctctgcacc      780
atgtag                                                                786
```

<210> SEQ ID NO 11
<211> LENGTH: 197
<212> TYPE: PRT
<213> ORGANISM: Homo sapiens

<400> SEQUENCE: 11

```
Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Gly Ala Lys Asp Thr Lys Pro Met Gly Arg
        35                  40                  45

Ser Gly Ala Thr Ser Arg Lys Ala Leu Glu Thr Leu Arg Arg Val Gly
    50                  55                  60

Asp Gly Val Gln Arg Asn His Glu Thr Ala Phe Gln Gly Met Leu Arg
65                  70                  75                  80

Lys Leu Asp Ile Lys Asn Glu Asp Val Lys Ser Leu Ser Arg Val
                85                  90                  95

Met Ile His Val Phe Ser Asp Gly Val Thr Asn Trp Gly Arg Ile Val
            100                 105                 110

Thr Leu Ile Ser Phe Gly Ala Phe Val Ala Lys His Leu Lys Thr Ile
        115                 120                 125

Asn Gln Glu Ser Cys Ile Glu Pro Leu Ala Glu Ser Ile Thr Asp Val
    130                 135                 140

Leu Val Arg Thr Lys Arg Asp Trp Leu Val Lys Gln Arg Gly Trp Asp
145                 150                 155                 160

Gly Phe Val Glu Phe His Val Glu Asp Leu Glu Gly Ile Arg
                165                 170                 175

Asn Val Leu Leu Ala Phe Ala Gly Val Ala Gly Val Gly Ala Gly Leu
            180                 185                 190

Ala Tyr Leu Ile Arg
        195
```

<210> SEQ ID NO 12

-continued

```
<211> LENGTH: 594
<212> TYPE: DNA
<213> ORGANISM: Homo sapiens

<400> SEQUENCE: 12
atgtttggcc tcaaaagaaa cgcggtaatc ggactcaacc tctactgtgg ggggccggc      60 ttgggggccg gcagcggcgg cgccacccgc ccgggagggc gacttttggc caccggcgcc    120
aaggacacaa agccaatggg caggtctggg gccaccagca ggaaggcgct ggagacctta    180 cgacggggttg gggatggcgt gcagcgcaac cacgagacgg ccttccaagg catgcttcgg   240
aaactggaca tcaaaaacga agacgatgtg aaatcgttgt ctcgagtgat gatccatgtt    300
ttcagcgacg gcgtaacaaa ctggggcagg attgtgactc tcatttcttt tggtgccttt    360
gtggctaaac acttgaagac cataaaccaa gaaagctgca tcgaaccatt agcagaaagt    420
atcacagacg ttctcgtaag gacaaaacgg gactggctag ttaaacaaag aggctgggat    480
gggtttgtgg agttcttcca tgtagaggac ctagaaggtg gcatcaggaa tgtgctgctg    540
gcttttgcag gtgttgctgg agtaggagct ggtttggcat atctaataag atag          594
```

```
<210> SEQ ID NO 13
<211> LENGTH: 205
<212> TYPE: PRT
<213> ORGANISM: Homo sapiens

<400> SEQUENCE: 13

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Leu Gly Asp Val Ser Leu Gly
        195                 200                 205
```

```
<210> SEQ ID NO 14
<211> LENGTH: 618
<212> TYPE: DNA
<213> ORGANISM: Homo sapiens
```

<400> SEQUENCE: 14

```
atggcgcacg ctgggagaac agggtacgat aaccgggaga tagtgatgaa gtacatccat      60
tataagctgt cgcagagggg ctacgagtgg gatgcgggag atgtgggcgc cgcgcccccg     120
ggggccgccc ccgcaccggg catcttctcc tcccagcccg gcacacgcc ccatccagcc      180
gcatcccggg accggtcgc caggacctcg ccgctgcaga ccccggctgc cccggcgcc       240
gccgcgggc ctgcgctcag cccggtgcca cctgtggtcc acctgaccct ccgcaggcc       300
ggcgacgact tctcccgccg ctaccgccgc gacttcgccg agatgtccag ccagctgcac     360
ctgacgccct tcaccgcgcg gggacgcttt gccacggtgg tggaggagct cttcagggac     420
ggggtgaact gggggaggat tgtggccttc tttgagttcg gtggggtcat gtgtgtggag     480
agcgtcaacc gggagatgtc gcccctggtg gacaacatcg ccctgtggat gactgagtac     540
ctgaaccggc acctgcacac ctggatccag gataacggag gctgggtagg tgcacttggt     600
gatgtgagtc tgggctga                                                    618
```

<210> SEQ ID NO 15
<211> LENGTH: 138
<212> TYPE: PRT
<213> ORGANISM: Homo sapiens

<400> SEQUENCE: 15

```
Met Ala Lys Gln Pro Ser Asp Val Ser Ser Glu Cys Asp Arg Glu Gly
1               5                   10                  15
Arg Gln Leu Gln Pro Ala Glu Arg Pro Pro Gln Leu Arg Pro Gly Ala
            20                  25                  30
Pro Thr Ser Leu Gln Thr Glu Pro Gln Asp Arg Ser Pro Ala Pro Met
        35                  40                  45
Ser Cys Asp Lys Ser Thr Gln Thr Pro Ser Pro Pro Cys Gln Ala Phe
    50                  55                  60
Asn His Tyr Leu Ser Ala Met Ala Ser Met Arg Gln Ala Glu Pro Ala
65                  70                  75                  80
Asp Met Arg Pro Glu Ile Trp Ile Ala Gln Glu Leu Arg Arg Ile Gly
                85                  90                  95
Asp Glu Phe Asn Ala Tyr Tyr Ala Arg Arg Val Phe Leu Asn Asn Tyr
            100                 105                 110
Gln Ala Ala Glu Asp His Pro Arg Met Val Ile Leu Arg Leu Leu Arg
        115                 120                 125
Tyr Ile Val Arg Leu Val Trp Arg Met His
    130                 135
```

<210> SEQ ID NO 16
<211> LENGTH: 417
<212> TYPE: DNA
<213> ORGANISM: Homo sapiens

<400> SEQUENCE: 16

```
atggcaaagc aaccttctga tgtaagttct gagtgtgacc gagaaggtag acaattgcag      60
cctgcggaga ggcctcccca gctcagacct ggggccccta cctccctaca gacagagcca     120
caagacagga gcccagcacc catgagttgt gacaaatcaa cacaaacccc aagtcctcct     180
tgccaggcct tcaaccacta tctcagtgca atggcttcca tgaggcaggc tgaacctgca     240
gatatgcgcc cagagatatg gatcgcccaa gagttgcggc gtattggaga cgagtttaac     300
gcttactatg caaggagggt atttttgaat aattaccaag cagccgaaga ccacccacga     360
```

```
atggttatct tacgactgtt acgttacatt gtccgcctgg tgtggagaat gcattga            417
```

<210> SEQ ID NO 17
<211> LENGTH: 350
<212> TYPE: PRT
<213> ORGANISM: Homo sapiens

<400> SEQUENCE: 17

```
Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
            260                 265                 270

Phe Val Ala Lys His Leu Lys Thr Ile Asn Gln Glu Ser Cys Ile Glu
        275                 280                 285

Pro Leu Ala Glu Ser Ile Thr Asp Val Leu Val Arg Thr Lys Arg Asp
    290                 295                 300

Trp Leu Val Lys Gln Arg Gly Trp Asp Gly Phe Val Glu Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350
```

<210> SEQ ID NO 18
<211> LENGTH: 1053

```
<212> TYPE: DNA
<213> ORGANISM: Homo sapiens

<400> SEQUENCE: 18
atgtttggcc tcaaaagaaa cgcggtaatc ggactcaacc tctactgtgg gggggccggc    60
ttggggccg gcagcggcgg cgccacccgc ccgggagggc gacttttggc tacggagaag    120
gaggcctcgg cccggcgaga gataggggga ggggaggccg gcgcggtgat tggcggaagc    180
gccggcgcaa gccccccgtc caccctcacg ccagactccc ggagggtcgc gcggccgccg    240
cccattggcg ccgaggtccc cgacgtcacc gcgaccccg cgaggctgct tttcttcgcg     300
cccaccgcc gcgcggcgcc gcttgaggag atggaagccc cggccgctga cgccatcatg     360
tcgcccgaag aggagctgga cgggtacgag ccggagcctc tcgggaagcg gccggctgtc    420
ctgccgctgc tggagttggt cggggaatct ggtaataaca ccagtacgga cgggtcacta    480
ccctcgacgc cgccgccagc agaggaggag gaggacgagt tgtaccggca gtcgctggag    540
attatctctc ggtaccttcg ggagcaggcc accggcgcca aggacacaaa gccaatgggc    600
aggtctgggg ccaccagcag gaaggcgctg agaccttac gacgggttgg ggatggcgtg     660
cagcgcaacc acgagacggc cttccaaggc atgcttcgga aactggacat caaaaacgaa    720
gacgatgtga atcgttgtc tcgagtgatg atccatgttt tcagcgacgg cgtaacaaac    780
tggggcagga ttgtgactct catttctttt ggtgcctttg tggctaaaca cttgaagacc    840
ataaaccaag aaagctgcat cgaaccatta gcagaaagta tcacagacgt tctcgtaagg    900
acaaaacggg actggctagt taaacaaaga ggctgggatg ggttgtgga gttcttccat     960
gtagaggacc tagaaggtgg catcaggaat gtgctgctgg cttttgcagg tgttgctgga   1020
gtaggagctg gtttggcata tctaataaga tag                               1053

<210> SEQ ID NO 19
<211> LENGTH: 271
<212> TYPE: PRT
<213> ORGANISM: Homo sapiens

<400> SEQUENCE: 19

Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160
```

```
Pro Ser Thr Pro Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Trp Val Cys Gly Val Leu Pro Cys Arg Gly
225                 230                 235                 240

Pro Arg Arg Trp His Gln Glu Cys Ala Ala Gly Phe Cys Arg Cys Cys
                245                 250                 255

Trp Ser Arg Ser Trp Phe Gly Ile Ser Asn Lys Ile Ala Leu Leu
            260                 265                 270

<210> SEQ ID NO 20
<211> LENGTH: 816
<212> TYPE: DNA
<213> ORGANISM: Homo sapiens

<400> SEQUENCE: 20
atgtttggcc tcaaaagaaa cgcggtaatc ggactcaacc tctactgtgg ggggccggc      60 ttggggccg gcagcggcgg cgccacccgc ccgggagggc gacttttggc tacgagaag     120 gaggcctcgg cccggcgaga gatagggga ggggaggccg gcgcggtgat tggcggaagc    180
gccggcgcaa gccccccgtc caccctcacg ccagactccc ggagggtcgc gcggccgccg   240
cccattggcg ccgaggtccc cgacgtcacc gcgaccccg cgaggctgct tttcttcgcg    300
cccacccgcc gcgcggcgcc gcttgaggag atggaagccc cggccgctga cgccatcatg    360
tcgcccgaag aggagctgga cgggtacgag ccggagcctc tcgggaagcg gccggctgtc   420
ctgccgctgc tggagttggt cggggaatct ggtaataaca ccagtacgga cgggtcacta   480
ccctcgacgc cgccgccagc agaggaggag gaggacgagt tgtaccggca gtcgctggag   540
attatctctc ggtaccttcg ggagcaggcc accggcgcca aggacacaaa gccaatgggc   600
aggtctgggg ccaccagcag gaaggcgctg gagaccttac gacgggttgg ggatggcgtg   660
cagcgcaacc acgagacggc cttccaagga tgggtttgtg gagttcttcc atgtagagga   720
cctagaaggt ggcatcagga atgtgctgct ggcttttgca ggtgttgctg gagtaggagc   780
tggtttggca tatctaataa gatagcctta ctgtaa                              816

<210> SEQ ID NO 21
<211> LENGTH: 236
<212> TYPE: PRT
<213> ORGANISM: Homo sapiens

<400> SEQUENCE: 21

Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Gln Ala Pro
    50                  55                  60

Gln Leu Arg Pro Ala Ala Asp Gly Gln Pro Ser Gly Gly Gly His Lys
65                  70                  75                  80
```

```
Ser Ala Pro Lys Gln Val Lys Arg Gln Arg Ser Ser Pro Glu Leu
            85                  90                  95

Met Arg Cys Lys Arg Arg Leu Asn Phe Ser Gly Phe Gly Tyr Ser Leu
            100                 105                 110

Pro Gln Gln Gln Pro Ala Ala Val Ala Arg Arg Asn Glu Arg Glu Arg
        115                 120                 125

Asn Arg Val Lys Leu Val Asn Leu Gly Phe Ala Thr Leu Arg Glu His
        130                 135                 140

Val Pro Asn Gly Ala Ala Asn Lys Lys Met Ser Lys Val Glu Thr Leu
145                 150                 155                 160

Arg Ser Ala Val Glu Tyr Ile Arg Ala Leu Gln Gln Leu Leu Asp Glu
                165                 170                 175

His Asp Ala Val Ser Ala Ala Phe Gln Ala Gly Val Leu Ser Pro Thr
                180                 185                 190

Ile Ser Pro Asn Tyr Ser Asn Asp Leu Asn Ser Met Ala Gly Ser Pro
            195                 200                 205

Val Ser Ser Tyr Ser Ser Asp Glu Gly Ser Tyr Asp Pro Leu Ser Pro
        210                 215                 220

Glu Glu Gln Glu Leu Leu Asp Phe Thr Asn Trp Phe
225                 230                 235

<210> SEQ ID NO 22
<211> LENGTH: 711
<212> TYPE: DNA
<213> ORGANISM: Homo sapiens

<400> SEQUENCE: 22
atggaaagct ctgccaagat ggagagcggc ggcgccggcc agcagcccca gccgcagccc      60
cagcagccct cctgccgcc cgcagcctgt ttctttgcca cggccgcagc cgcggcggcc     120
gcagccgccg cagcggcagc gcagagcgcg cagcagcagc agcagcagca gcagcagcag     180
cagcaggcgc cgcagctgag accggcggcc gacggccagc cctcagggg cggtcacaag     240 tcagcgccca gcaagtcaa gcgacagcgc tcgtcttcgc ccgaactgat gcgctgcaaa     300
cgccggctca acttcagcgg ctttggctac agcctgccgc agcagcagcc ggccgccgtg     360
gcgcgccgca acgagcgcga gcgcaaccgc gtcaagttgg tcaacctggg ctttgccacc     420
cttcgggagc acgtccccaa cggcgcggcc aacaagaaga tgagtaaggt ggagacactg     480
cgctcggcgg tcgagtacat ccgcgcgctg cagcagctgc tggacgagca tgacgcggtg     540
agcgccgcct tccaggcagg cgtcctgtcg cccaccatct cccccaacta ctccaacgac     600
ttgaactcca tggccggctc gccggtctca tcctactcgt cggacgaggg ctcttacgac     660
ccgctcagcc ccgaggagca ggagcttctc gacttcacca actggttctg a             711
```

METHOD AND COMPOSITIONS FOR PREDICTING ANTI-CANCER EFFICACY OF COMPOUNDS TARGETING APOPTOSIS PATHWAY

RELATED APPLICATIONS

This application is a U.S. National Phase application, filed under 35 U.S.C. § 371(c), of International Application No. PCT/CN2020/132191, filed Nov. 27, 2020, which claims priority to, and the benefit of, Chinese Application No. PCT/CN2019/121214, filed on Nov. 27, 2019, the disclosures of which are incorporated herein by reference in its entirety.

REFERENCE TO AN ELECTRONIC SEQUENCE LISTING

The contents of the electronic sequence listing (APGC_005_N01US_SeqList_ST25.txt; Size: 31,896 bytes; and Date of Creation: Dec. 18, 2024) are herein incorporated by reference in its entirety.

FIELD OF THE INVENTION

The present invention generally relates to cancer treatment.

BACKGROUND

The evasion of apoptosis is a hallmark of human cancer and is a frequent cause of therapeutic resistance (Hanahan D et al, Cell (2000) 100:57-70; Delbridge A R et al, Cold Spring Harb Perspect Biol (2012) 4). Therefore, targeting key apoptosis players in human cancer is an attractive new strategy for the development of entirely new classes of anticancer therapies.

Clinical responses to anticancer therapies are often restricted to a subset of patients. To maximize the efficiency of anticancer therapy, personalized chemotherapy based on molecular biomarkers has been proposed. However, the identification of predicative biomarkers capable of predicting response to anticancer therapies still remains a challenge. Therefore, there is a continuing need for development of biomarkers for predicting anti-cancer efficacy of compounds targeting apoptosis pathway.

SUMMARY OF INVENTION

In one aspect, the present disclosure provides a method for treating cancer in a subject in need thereof. In one embodiment, the method comprises: measuring a level of at least one biomarker comprising Noxa, in a test sample derived from the subject; comparing the level of the at least one biomarker with a corresponding reference level of the at least one biomarker to determine difference from the reference level; and administering an effective amount of an MDM2 inhibitor or a Bcl-2/Bcl-xL dual inhibitor or a Bcl-xL inhibitor or a Bcl-2 inhibitor to the subject when the difference reaches a predetermined threshold.

In another aspect, the present disclosure provides a method for identifying a subject having cancer as likely to respond to treatment with an MDM2 inhibitor or a Bcl-2/Bcl-xL dual inhibitor or a Bcl-xL inhibitor or a Bcl-2 inhibitor. In one embodiment, the method comprises: measuring a level of at least one biomarker comprising Noxa, in a test sample derived from the subject; and comparing the level of the at least one biomarker with a corresponding reference level of the at least one biomarker to determine difference from the reference level; and identifying the subject as likely to respond to the treatment with the MDM2 inhibitor or Bcl-2/Bcl-xL dual inhibitor or Bcl-xL inhibitor or Bcl-2 inhibitor when the difference reaches a predetermined threshold.

In one embodiment, the method for identifying a subject having cancer as likely to respond to treatment with an MDM2 inhibitor or a Bcl-2/Bcl-xL dual inhibitor or a Bcl-xL inhibitor or a Bcl-2 inhibitor further comprises administering an effective amount of the MDM2 inhibitor or Bcl-2/Bcl-xL dual inhibitor or Bcl-xL inhibitor or Bcl-2 inhibitor to the subject identified as likely to respond to the treatment with an MDM2 inhibitor an Bcl-2/Bcl-xL dual inhibitor or a Bcl-xL inhibitor or a Bcl-2 inhibitor.

In another aspect, the present disclosure provides a method for monitoring therapeutic efficacy in a subject having cancer and having been treated with an MDM2 inhibitor or a Bcl-2/Bcl-xL dual inhibitor or a Bcl-xL inhibitor or a Bcl-2 inhibitor for a therapeutic period. In one embodiment, the method comprises: obtaining a test sample from the subject after the therapeutic period; measuring a level of at least one biomarker comprising Noxa, in the test sample to obtain a post-treatment level of the at least one biomarker; comparing the post-treatment level with a baseline level of the at least one biomarker in the sample derived from the subject before the therapeutic period, to determine post-treatment change in the level of the at least one biomarker; and continuing administering the MDM2 inhibitor or Bcl-2/Bcl-xL dual inhibitor or Bcl-xL inhibitor or Bcl-2 inhibitor to the subject when the post-treatment change reaches a predetermined threshold, or when the post-treatment change does not reach the predetermined threshold, increasing the dose of the MDM2 inhibitor or Bcl-2/Bcl-xL dual inhibitor or Bcl-xL inhibitor or Bcl-2 inhibitor to the subject, or administering an effective amount of second anti-cancer therapeutic agent in combination to the MDM2 inhibitor Bcl-2/Bcl-xL dual inhibitor or Bcl-xL inhibitor or Bcl-2 inhibitor to the subject, or discontinuing the administering the MDM2 inhibitor or Bcl-2/Bcl-xL dual inhibitor or Bcl-xL inhibitor or Bcl-2 inhibitor to the subject.

In certain embodiments, an elevation or maintenance of the level of Noxa in the sample after the therapeutic period indicates likelihood of continued responsiveness to the treatment with the MDM2 inhibitor or Bcl-2/Bcl-xL dual inhibitor or Bcl-xL inhibitor or Bcl-2 inhibitor. In certain embodiments, a reduction of the level of Noxa in the sample indicates likelihood of decreased responsiveness to the treatment with the MDM2 inhibitor Bcl-2/Bcl-xL dual inhibitor or Bcl-xL inhibitor or Bcl-2 inhibitor.

In some embodiments, the second anti-therapeutic agent is can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof.

In some embodiments, an immune checkpoint molecule is administered as a second anti-cancer therapeutic agent in combination with an MDM2 inhibitor. In some embodiments, a chemotherapeutic agent is administered as a second anti-cancer therapeutic agent in combination with a Bcl-2/Bcl-xL inhibitor or a Bcl-2 inhibitor or a Bcl-xL inhibitor.

In some embodiments, the second anti-cancer therapeutic can be administered simultaneously, separately or sequentially with the MDM2 inhibitor or Bcl-2/Bcl-xL inhibitor or Bcl-2 inhibitor or Bcl-xL inhibitor.

In certain embodiments, the cancer is solid tumor or hematological cancer. In certain embodiments, the cancer is selected from adrenocortical carcinoma, anal cancer, astrocytoma, childhood cerebellar or cerebral, basal-cell carcinoma, bile duct cancer, bladder cancer (e.g. urinary bladder cancer), bone tumor, brain cancer, cerebellar astrocytoma, cerebral astrocytoma/malignant glioma, ependymoma, medulloblastoma, supratentorial primitive neuroectodermal tumors, visual pathway and hypothalamic glioma, breast cancer, Burkitt's lymphoma, cervical cancer, colon cancer, emphysema, endometrial cancer, esophageal cancer, Ewing's sarcoma, retinoblastoma, gastric (stomach) cancer, glioma, head and neck cancer, heart cancer, Hodgkin lymphoma, islet cell carcinoma (endocrine pancreas), Kaposi sarcoma, kidney cancer (renal cell cancer), laryngeal cancer, liver cancer (e.g. hepatocellular carcinoma), lung cancer (such as small cell lung cancer, non-small cell lung cancer, lung adenocarcinoma, lung squamous cell carcinoma), neuroblastoma, non-Hodgkin lymphoma, ovarian cancer, pancreatic cancer, gastro-intestinal cancer, pharyngeal cancer, prostate cancer, rectal cancer, renal cell carcinoma (kidney cancer), retinoblastoma, Ewing family of tumors, skin cancer, stomach cancer, testicular cancer, throat cancer, thyroid cancer, cholangiocarcinoma, vaginal cancer, and small cell carcinoma (e.g. small cell lung cancer (SCLC), extrapulmonary small-cell carcinoma (EPSCC), small-cell carcinoma of the prostate, or small-cell carcinoma of the bladder), melanoma, cutaneous squamous cell carcinoma, glioblastoma, hysterocarcinoma, osteosarcoma, uterine cancer, uterine CS, colorectal cancer, cervical cancer, sarcoma, chromophobe, renal cell carcinoma (RCC), clear cell RCC, papillary RCC, uveal melanoma, testicular germ cell, low grade glioma (LGG), mesothelioma, PCPG, or thymoma. In certain embodiments, the cancer is selected from chronic lymphocytic leukemia (CLL), acute myeloid leukemia (AML), T-cell prolymphocytic leukemia, multiple myeloma (MM), Waldenstrom macroglobulinemia (WM), acute lymphoblastic leukemia (ALL) and lymphoma (e.g., mantel cell lymphoma, diffuse large B cell lymphoma).

In one aspect, the present disclosure provides a method for treating cancer in a subject in need thereof. In one embodiment, the method comprises: measuring a level of at least one biomarker comprising ASCL1, in a test sample derived from the subject; comparing the level of the at least one biomarker with a corresponding reference level of the at least one biomarker to determine difference from the reference level; and administering an effective amount of an MDM2 inhibitor or a Bcl-2/Bcl-xL dual inhibitor or a Bcl-xL inhibitor or a Bcl-2 inhibitor to the subject when the difference reaches a predetermined threshold.

In another aspect, the present disclosure provides a method for identifying a subject having cancer as likely to respond to treatment with an MDM2 inhibitor or a Bcl-2/Bcl-xL dual inhibitor or a Bcl-xL inhibitor or a Bcl-2 inhibitor. In one embodiment, the method comprises: measuring a level of at least one biomarker comprising ASCL1, in a test sample derived from the subject; and comparing the level of the at least one biomarker with a corresponding reference level of the at least one biomarker to determine difference from the reference level; and identifying the subject as likely to respond to the treatment with the MDM2 inhibitor or Bcl-2/Bcl-xL dual inhibitor or Bcl-xL inhibitor or Bcl-2 inhibitor when the difference reaches a predetermined threshold.

In one embodiment, the method for identifying a subject having cancer as likely to respond to treatment with an MDM2 inhibitor or a Bcl-2/Bcl-xL dual inhibitor or a Bcl-xL inhibitor or a Bcl-2 inhibitor further comprises administering an effective amount of the MDM2 inhibitor or Bcl-2/Bcl-xL dual inhibitor or Bcl-xL inhibitor or Bcl-2 inhibitor to the subject identified as likely to respond to the treatment with an MDM2 inhibitor or a Bcl-2/Bcl-xL dual inhibitor or a Bcl-xL inhibitor or a Bcl-2 inhibitor.

In certain embodiments, the cancer is a neuroendocrine cancer. In certain embodiments, the cancer is selected from large cell neuroendocrine carcinoma of lung (LCNEC), thyroid tumor, mid-gut cancer, gallbladder cancer, ovarian cancer, cervical cancer, pheochromocytoma, Merkel's cell tumor, gastric cancer, esophageal cancer, pancreatic cancer, gastro-intestinal cancer, breast cancer, liver cancer, head and neck cancer, cholangiocarcinoma, or small cell carcinoma (e.g. small cell lung cancer, extrapulmonary small-cell carcinoma (EPSCC), small-cell carcinoma of the prostate, or small-cell carcinoma of the bladder).

In one aspect, the present disclosure provides a method for treating cancer in a subject in need thereof. In one embodiment, the method comprises: measuring a level of at least one biomarker comprising both Noxa and ASCL1, in a test sample derived from the subject; comparing the level of the at least one biomarker with a corresponding reference level of the at least one biomarker to determine difference from the reference level; and administering an effective amount of an MDM2 inhibitor or a Bcl-2/Bcl-xL dual inhibitor or a Bcl-xL inhibitor or a Bcl-2 inhibitor to the subject when the difference reaches a predetermined threshold.

In another aspect, the present disclosure provides a method for identifying a subject having cancer as likely to respond to treatment with an MDM2 inhibitor or a Bcl-2/Bcl-xL dual inhibitor or a Bcl-xL inhibitor or a Bcl-2 inhibitor. In one embodiment, the method comprises: measuring a level of at least one biomarker comprising both Noxa and ASCL1, in a test sample derived from the subject; and comparing the level of the at least one biomarker with a corresponding reference level of the at least one biomarker to determine difference from the reference level; and identifying the subject as likely to respond to the treatment with the MDM2 inhibitor or Bcl-2/Bcl-xL dual inhibitor or Bcl-xL inhibitor or Bcl-2 inhibitor when the difference reaches a predetermined threshold.

In one embodiment, the method for identifying a subject having cancer as likely to respond to treatment with an MDM2 inhibitor or a Bcl-2/Bcl-xL dual inhibitor or a Bcl-xL inhibitor or a Bcl-2 inhibitor further comprises administering an effective amount of the MDM2 inhibitor or Bcl-2/Bcl-xL dual inhibitor or Bcl-xL inhibitor or Bcl-2 inhibitor to the subject identified as likely to respond to the treatment with an MDM2 inhibitor or a Bcl-2/Bcl-xL dual inhibitor or a Bcl-xL inhibitor or a Bcl-2 inhibitor.

In another aspect, the present disclosure provides a method for monitoring therapeutic efficacy in a subject having cancer and having been treated with an MDM2 inhibitor or a Bcl-2/Bcl-xL dual inhibitor or a Bcl-xL inhibitor or a Bcl-2 inhibitor for a therapeutic period. In one embodiment, the method comprises: obtaining a test sample from the subject after the therapeutic period; measuring a level of at least one biomarker comprising both Noxa and ASCL1, in the test sample to obtain a post-treatment level of the at least one biomarker; comparing the post-treatment level with a baseline level of the at least one biomarker in the sample derived from the subject before the therapeutic period, to determine post-treatment change in the level of the at least one biomarker; and continuing administering the MDM2 inhibitor or Bcl-2/Bcl-xL dual inhibitor or Bcl-xL inhibitor or Bcl-2 inhibitor to the subject when the post-treatment change reaches a predetermined threshold, or when the post-treatment change does not reach the predetermined threshold, increasing the dose of the MDM2 inhibitor or Bcl-2/Bcl-xL dual inhibitor or Bcl-xL inhibitor or Bcl-2 inhibitor to the subject, administering an effective amount of second anti-cancer therapeutic agent in combination to the MDM2 inhibitor or Bcl-2/Bcl-xL dual inhibitor or Bcl-xL inhibitor or Bcl-2 inhibitor to the subject, or discontinuing the administering the MDM2 inhibitor or Bcl-2/Bcl-xL dual inhibitor or Bcl-xL inhibitor or Bcl-2 inhibitor to the subject.

In certain embodiments, the cancer is a neuroendocrine cancer.

In certain embodiments, the at least one biomarker comprises Noxa and ASCL1, and the cancer is neuroendocrine cancer. In certain embodiments, the neuroendocrine cancer is large cell neuroendocrine carcinoma of lung (LCNEC), thyroid tumor, mid-gut cancer, gallbladder cancer, ovarian cancer, cervical cancer, pheochromocytoma, Merkel's cell tumor, gastric cancer, esophageal cancer, pancreatic cancer, gastro-intestinal cancer, breast cancer, liver cancer, head and neck cancer, cholangiocarcinoma, or small cell carcinoma (e.g. small cell lung cancer, extrapulmonary small-cell carcinoma (EPSCC), small-cell carcinoma of the prostate, or small-cell carcinoma of the bladder). In certain embodiments, the neuroendocrine cancer is small cell carcinoma. In certain embodiments, the at least one biomarker comprises Noxa and ASCL1, and the cancer is small cell lung cancer.

In any aspects described herein, the level of the at least one biomarker is measured by mRNA level, protein level or DNA level. In certain embodiments, the level of the at least one biomarker is measured by an amplification assay, a hybridization assay, a sequencing assay or an immunoassay.

In certain embodiments, the amplification assay is a polymerase-chain reaction (PCR) based method.

In certain embodiments, the predetermined threshold is set by a statistical method.

In certain embodiments, the predetermined threshold for Noxa is reached when the level of Noxa in the test sample is at least 15% (e.g. at least 25%, at least 35%, at least 45%, at least 50%) higher than the corresponding reference level of Noxa.

In certain embodiments, the reference level of Noxa is representative of an average level of Noxa in a general population of subjects having cancer. In certain embodiments, the reference level of Noxa is measured in a control sample. In certain embodiments, the control sample is a sample having a level of Noxa that is representative of the average level of Noxa in a general cancer population.

In certain embodiments, the predetermined threshold for ASCL1 is reached when the level of ASCL1 in the test sample is at least 15% (e.g. at least 25%, at least 50%, at least 100%, at least 150%) higher than the corresponding reference level of ASCL1.

In certain embodiments, the reference level of ASCL1 is representative of an average level of ASCL1 in a general population of subjects having cancer.

In certain embodiments, the reference level of ASCL1 is measured in a control sample. In certain embodiments, the control sample is a sample having a level of ASCL1 that is representative of the average level of ASCL1 in a general cancer population.

In certain embodiments, the sample is a bodily fluid sample or a tissue sample.

In certain embodiments, the at least one biomarker further comprises one or more additional biomarkers selected from the group consisting of: Bcl-xL, Bcl-2, Mcl-1, a protein complex comprising Bcl-xL protein, a protein complex comprising Bcl-2, or any combination thereof.

In certain embodiments, the step of comparing is performed with an algorithm.

In certain embodiments, the algorithm comprises a classification algorithm.

In certain embodiments, the difference comprises a difference in a test score for the level in the test sample and a reference score for the reference level, and wherein the test score and the reference score are calculated by the algorithm.

In certain embodiments, the Bcl-2/Bcl-xL dual inhibitor described herein is a compound having a structure of formula (I), (II) or (III):

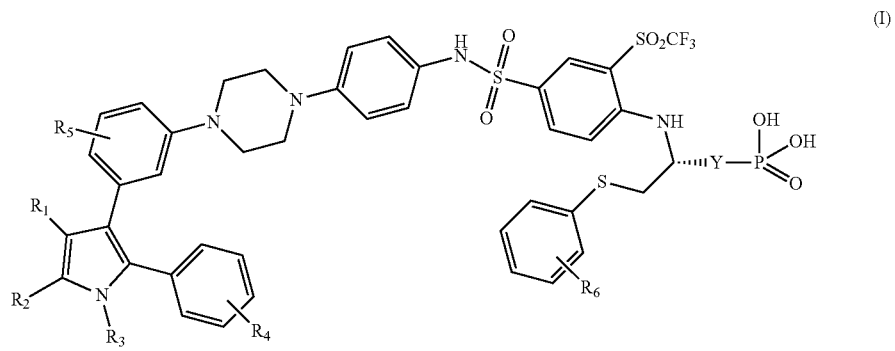

(I)

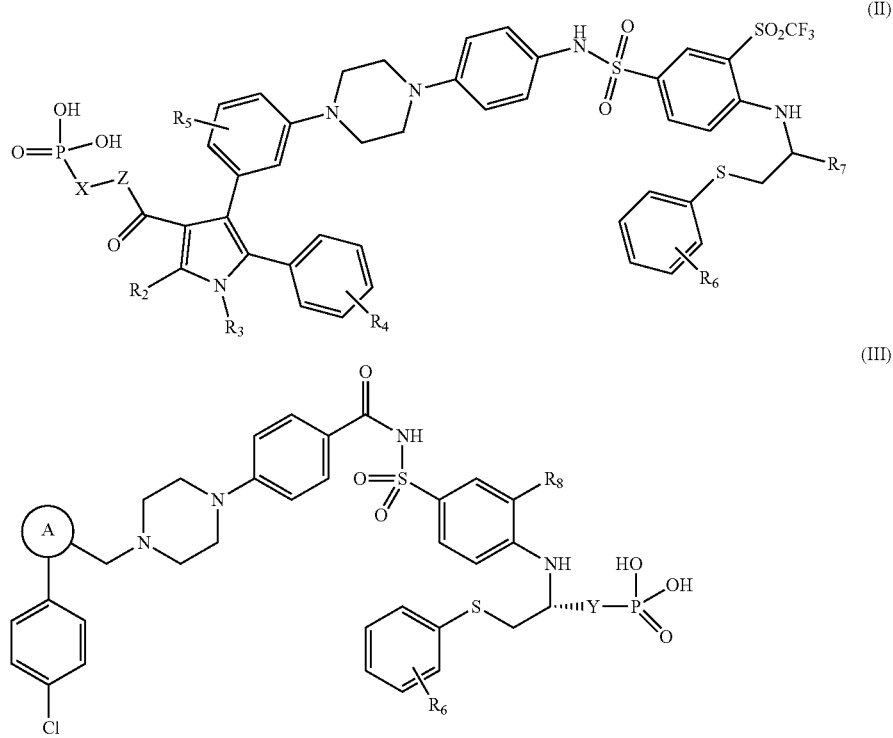

or a pharmaceutically acceptable salt thereof;
wherein the A ring is

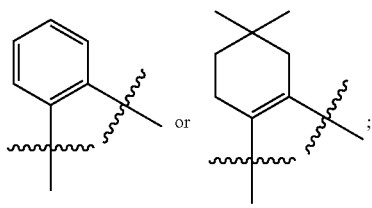

X, substituted or unsubstituted, is selected from the group consisting of alkylene, alkenylene, cycloalkylene, cycloalkenylene, and heterocycloalkylene;

Y is selected from the group consisting of $(CH_2)_n-N(R^a)_2$ and

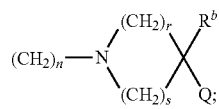

Q is selected from the group consisting of O, $O(CH_2)_{1-3}$, $NR^c$. $NR^c(C_{1-3}alkylene)$, $OC(=O)(C_{1-3}alkylene)$, $C(=O)O$, $C(=O)O(C_{1-3}alkylene)$, $NHC(=O)(C_{1-3}alkylene)$, $C(=O)NH$, and $C(=O)NH(C_{1-3}alkylene)$;

Z is O or $NR^c$;

$R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", COR', $CO_2R'$, OCOR', CONR'R", CONR'SO$_2$R", NR'COR", NR'CONR"R'", NR'C=SNR"R'", NR'SO$_2$R", SO$_2$R', and SO$_2$NR'R";

$R_3$ is selected from a group consisting of H, alkyl, cycloalkyl, alkenyl, cycloalkenyl, alkynyl, aryl, heteroaryl, heterocycloalkyl, OR', NR'R", OCOR', $CO_2R'$, COR', CONR'R", CONR'SO$_2$R", $C_{1-3}$alkyleneCH(OH)CH$_2$OH, SO$_2$R', and SO$_2$NR'R";

R', R", and R'", independently, are H, alkyl, cycloalkyl, alkenyl, cycloalkenyl, alkynyl, aryl, heteroaryl, $C_{1-3}$alkyleneheterocycloalkyl, or heterocycloalkyl;

R' and R", or R" and R'", can be taken together with the atom to which they are bound to form a 3 to 7 membered ring;

$R_4$ is hydrogen, halo, $C_{1-3}$alkyl, $CF_3$, or CN;

$R_5$ is hydrogen, halo, $C_{1-3}$alkyl, substituted $C_{1-3}$alkyl, hydroxyalkyl, alkoxy, or substituted alkoxy;

$R_6$ is selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", CONR'SO$_2$R", NR'COR", NR'CONR"R'", NR'C=SNR"R'", NR'SO$_2$R", SO$_2$R', and SO$_2$NR'R";

$R_7$, substituted or unsubstituted, is selected form the group consisting of hydrogen, alkyl, alkenyl, $(CH_2)_{0-3}$cycloalkyl, $(CH_2)_{0-3}$cycloalkenyl, $(CH_2)_{0-3}$heterocycloalkyl, $(CH_2)_{0-3}$aryl, and $(CH_2)_{0-3}$heteroaryl;

$R_a$ is selected form the group consisting of hydrogen, halo, $NO_2$, CN, $CF_3SO_2$, and $CF_3$;

$R_a$ is selected from the group consisting of hydrogen, alkyl, heteroalkyl, alkenyl, hydroxyalkyl, alkoxy, substituted alkoxy, cycloalkyl, cycloalkenyl, and heterocycloalkyl;

$R_b$ is hydrogen or alkyl;

$R_c$ is selected from the group consisting of hydrogen, alkyl, substituted alkyl, hydroxyalkyl, alkoxy, and substituted alkoxy; and n, r, and s, independently, are 1, 2, 3, 4, 5, or 6.

In certain embodiments, the Bcl-2/Bcl-xL dual inhibitor described herein is a compound having a structure of formula (IV):

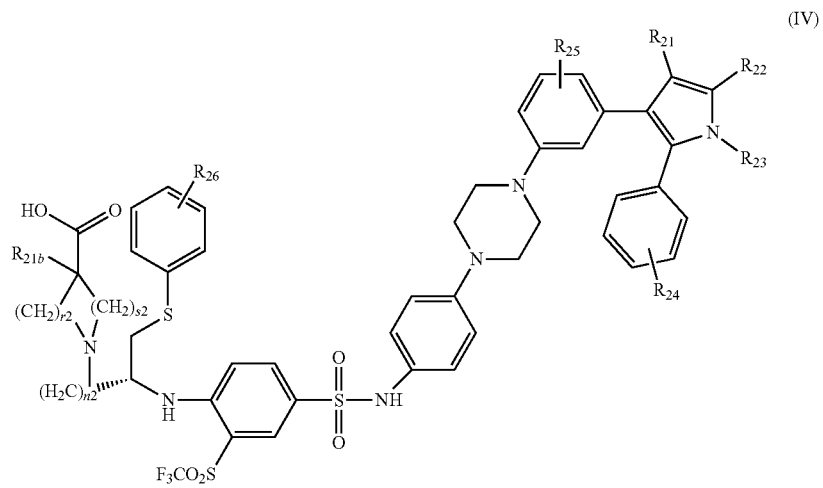

(IV)

or a pharmaceutically acceptable salt thereof;

$R_{21}$ is $SO_2R_2'$;

$R_{22}$ is alkyl, preferably $C_1$-$C_4$ alkyl, more preferably methyl, propyl, or isopropyl;

$R_{23}$ is alkyl, preferably $C_1$-$C_4$ alkyl, more preferably methyl, propyl, or isopropyl;

$R_{24}$ is halogen, preferably fluoride, chloride;

$R_{25}$ is halogen, preferably fluoride, chloride;

$R_{26}$ is selected from H, halogen, alkyl, preferably fluoride, chloride, $C_1$-$C_4$ alkyl, more preferably methyl, propyl, isopropyl;

$R_{21b}$ is H or alkyl, preferably $C_1$-$C_4$ alkyl, more preferably methyl, propyl, or isopropyl;

$n_2$, $r_2$ and $s_2$ are independently 1, 2, 3, 4, 5 or 6, more preferably, $r_2$ and $s_2$ are both 2 and $n_2$ is 3, 4 or 5, more preferably, all of $n_2$, $r_2$ and $s_2$ are 2; and $R_2'$ is alkyl, preferably $C_1$-$C_4$ alkyl, more preferably methyl, propyl, or isopropyl.

In certain embodiments, the Bcl-2 inhibitor described herein is a compound having a structure of formula (V):

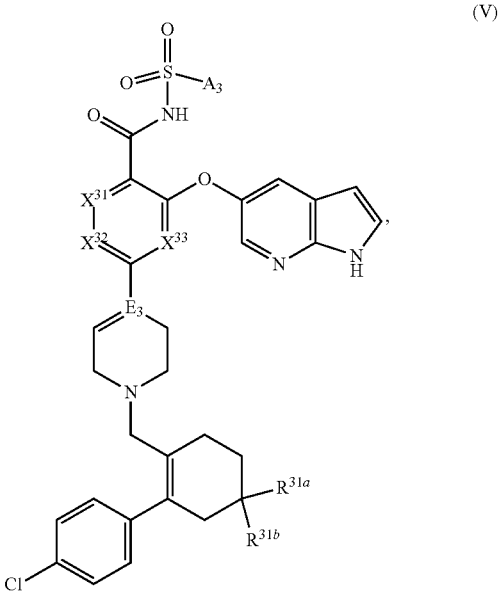

(V)

or a pharmaceutically acceptable salt thereof; $A_3$ is selected from the group consisting of:

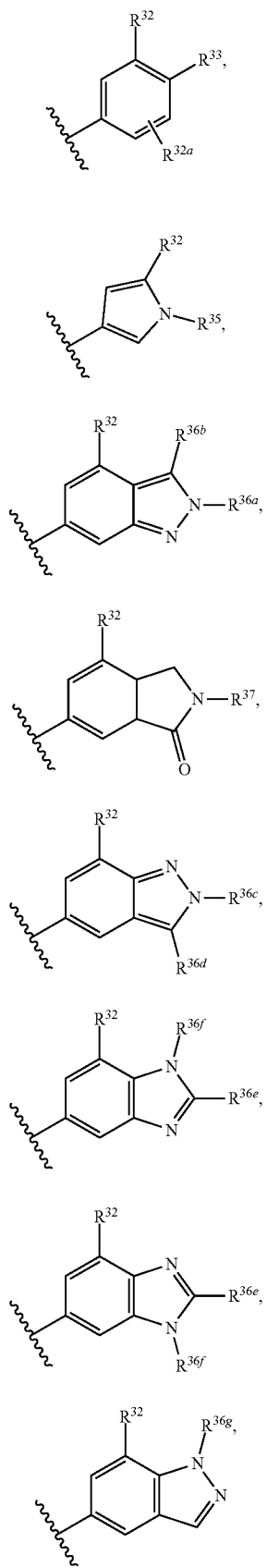

A-1
A-2
A-3
A-4
A-5
A-6
A-7
A-8

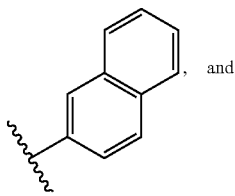

A-9

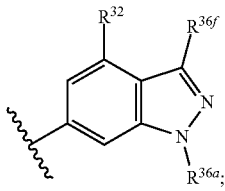

A-10

$E_3$ is a carbon atom and ═══ is a double bond; or
$E_3$ is a —C(H)— and ═══ is a single bond; or
$E_3$ is a nitrogen atom and ═══ is a single bond;
$X^{31}$, $X^{32}$, and $X^{33}$ are each independently selected from the group consisting of —CR$^{38}$═ and —N═;
$R^{31a}$ and $R^{31b}$ taken together with the carbon atom to which they are attached form a 3-, 4-, or 5-membered optionally substituted cycloalkyl; or
$R^{31a}$ and $R^{31b}$ taken together with the carbon atom to which they are attached form a 4- or 5-membered optionally substituted heterocyclo;
$R^{32}$ is selected from the group consisting of —NO$_2$, —SO$_2$CH$_3$, and —SO$_2$CF$_3$;
$R^{31}$ is selected from the group consisting of hydrogen and halogen;
$R^3$ is selected from the group consisting of hydrogen, —CN, —C≡CH, and —N(R$^{34a}$)(R$^{34b}$);
$R^{34a}$ is selected from the group consisting of optionally substituted C$_{1-6}$ alkyl, optionally substituted C$_{3-6}$ cycloalkyl, heterocyclo, heteroalkyl, (cycloalkyl)alkyl, and (heterocyclo)alkyl;
$R^{34b}$ is selected from the group consisting of hydrogen and C$_{1-6}$ alkyl;
$R^{35}$ is selected from the group consisting of optionally substituted C$_{1-6}$ alkyl, heterocyclo, heteroalkyl, (cycloalkyl)alkyl, and (heterocyclo)alkyl;
$R^{36a}$, $R^{36c}$, $R^{36e}$, $R^{36f}$, and $R^{36g}$ are each independently selected from the group consisting of hydrogen, optionally substituted C$_{1-6}$ alkyl, optionally substituted C$_{3-6}$ cycloalkyl, optionally substituted aryl, optionally substituted heteroaryl, heterocyclo, heteroalkyl, (cycloalkyl)alkyl, and (heterocyclo)alkyl;
$R^{36b}$ and $R^{36d}$ are each independently selected from the group consisting of hydrogen, C$_{1-4}$ alkyl, and halogen;
$R^{37}$ is selected from the group consisting of optionally substituted C$_{1-6}$ alkyl, heterocyclo, heteroalkyl, (cycloalkyl)alkyl, and (heterocyclo)alkyl; and
$R^{38}$ is selected from the group consisting of hydrogen and halogen.

In certain embodiments, the Bcl-2/Bcl-xL dual inhibitor or Bcl-xL inhibitor or Bcl-2 inhibitor is a compound selected from Table 1-A, Table 1-B and Table 1-C or a pharmaceutically acceptable salt thereof.

In certain embodiments, the Bcl-2/Bcl-xL dual inhibitor is (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4- carbonyloxy)ethylphosphonic acid (also referred to as "Compound A15" herein) having the following structure, or a pharmaceutically acceptable salt thereof:

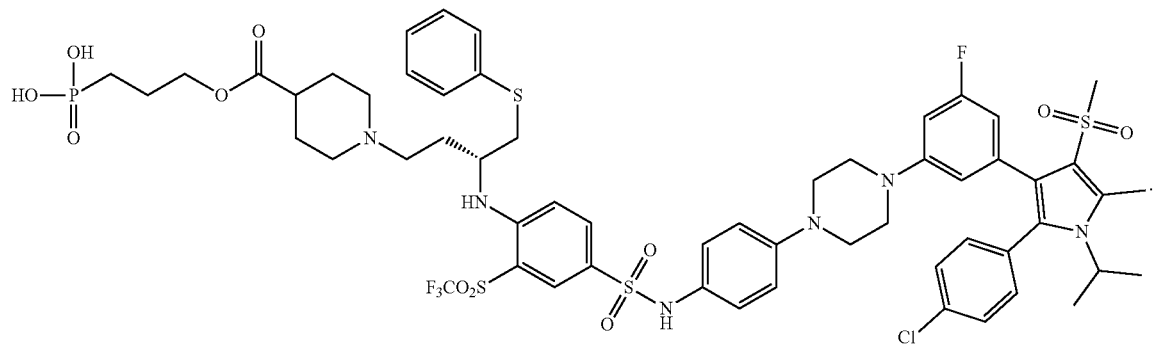

In certain embodiments, the Bcl-2/Bcl-xL dual inhibitor is (R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl) sulfamoyl)-2-(trifluoromethylsulfonyl)phenylamino)-4-(phenylthio)butyl)piperidine-4-carboxylic acid (also referred to as "Compound B4" herein) having the following structure, or a pharmaceutically acceptable salt thereof:

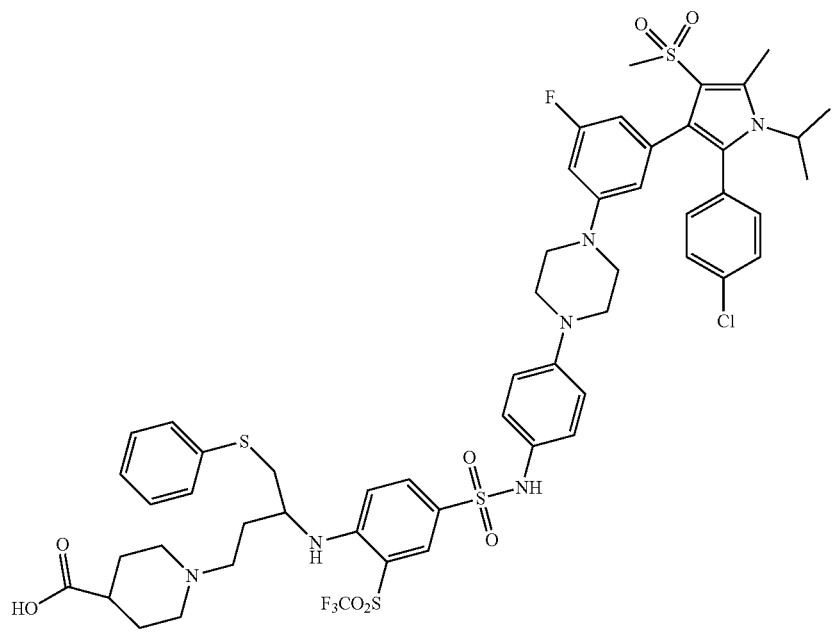

In certain embodiments, the Bcl-2 inhibitor is selected from the compounds having the following structures

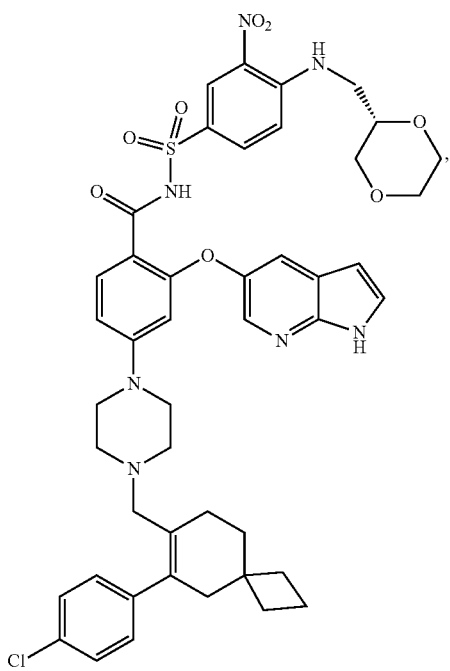
and
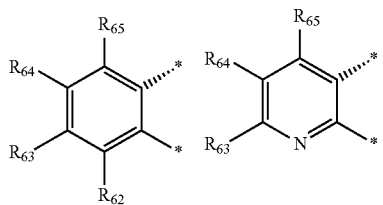
or a pharmaceutical acceptable salt thereof.
In certain embodiments, the MDM2 inhibitor comprises the chemical structure of the following formula (VI):
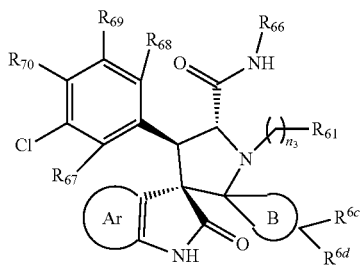
(VI)
or a pharmaceutically acceptable salt thereof, wherein
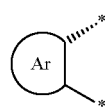
is selected from the group consisting of
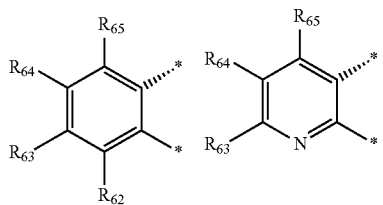

-continued

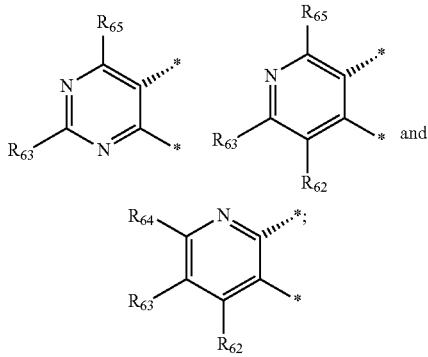

B is a $C_{4-7}$ carbocyclic ring;

$R_{61}$ is H, substituted or unsubstituted $C_{1-4}$ alkyl, substituted or unsubstituted cycloalkyl, substituted or unsubstituted heterocycloalkyl, $OR^{6a}$, or $NR^{6a}R^{6b}$;

$n_3$ is 0, 1, or 2;

$R_{62}$, $R_{63}$, $R_{64}$, $R_{65}$, $R_{67}$, $R_{68}$, $R_{69}$, and $R_{70}$, independently, are selected from the group consisting of H, F, Cl, $CH_3$, and $CF_3$;

$R_{66}$ is

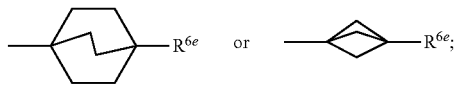

$R^{6a}$ is hydrogen or substituted or unsubstituted $C_{1-4}$ alkyl;
$R^{6b}$ is hydrogen or substituted or unsubstituted $C_{1-4}$ alkyl;
$R^{6c}$ and $R^{6d}$ are substituents on one carbon atom of ring B, wherein
$R^{6c}$ is H, $C_{1-3}$ alkyl, $C_{1-3}$ alkylene-$OR^{6a}$, $OR^{6a}$, or halo;
$R^{6d}$ is H, $C_{1-3}$ alkyl, $C_{1-3}$ alkylene-$OR^{6a}$, $OR^{6a}$, or halo; or
$R^{6c}$ and $R^{6d}$ are taken together with the carbon to which they are attached to form a 4 to 6-membered Spiro substituent, optionally containing an oxygen atom; and
$R^{6e}$ is $-C(=O)OR^{6a}$, $-C(=O)NR^{6a}R^{6b}$, or $-C(=O)NHSO_2CH_3$.

In certain embodiments,

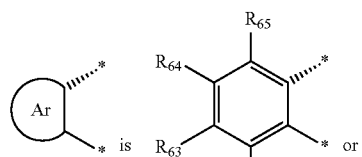

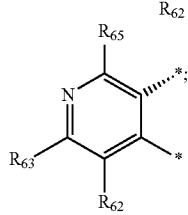

B is

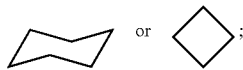

and
$R^{6c}$ and $R^{6d}$ are F and F, H and H, OH and $CH_3$, OH and H, $CH_3$ and $CH_3$, $CH_3$ and OH, H and OH, $CH_2CH_3$ and $CH_2CH_3$, or $CH_2OH$ and $CH_2OH$.

In certain embodiments,

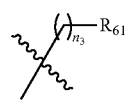

is H, $CH_3$, or $CH_2CH_3$.

In certain embodiments, $R_{62}$ is H; $R_{63}$ is halo; $R_{64}$ and $R_{65}$ are H.

In certain embodiments, $R_{67}$ is fluoro; each of $R_{68}$, $R_{69}$, and $R_{70}$ is H; and $R^{6e}$ is $-C(=O)OH$, $-C(=O)NH_2$, or $-C(=O)NHSO_2CH_3$.

In certain embodiments, the MDM2 inhibitor is a compound selected from:

Compound Q

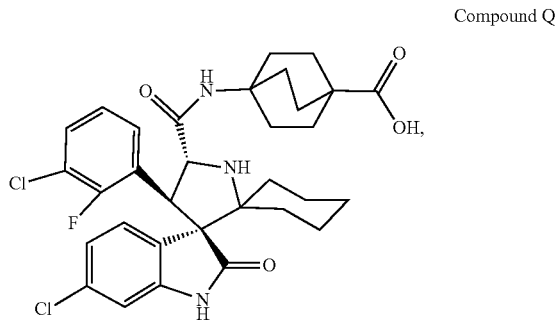

Compound M

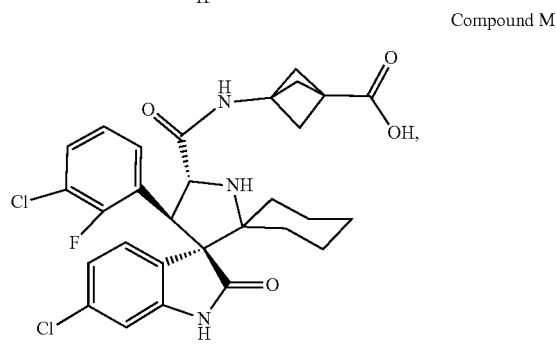

Compound N

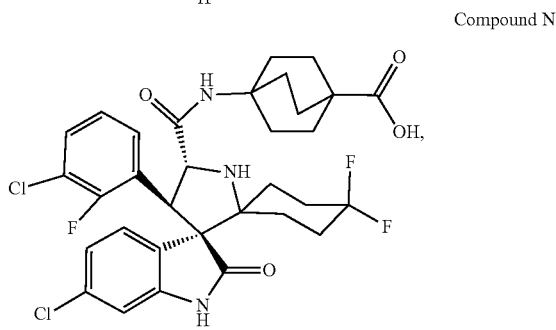

Compound H
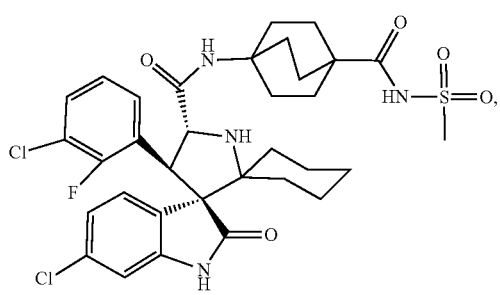
Compound J
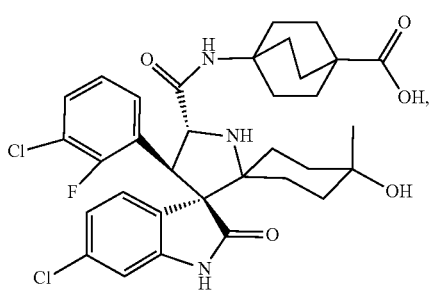
Compound G
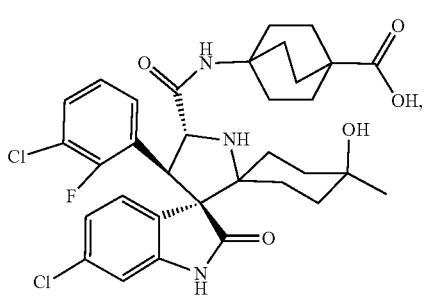
Compound E
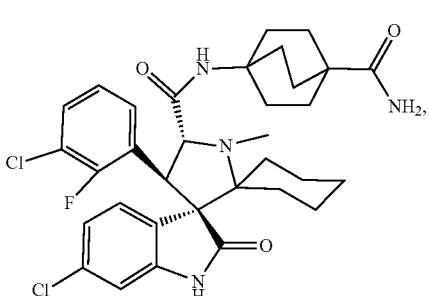
Compound C
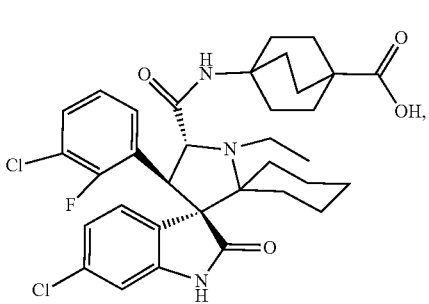
Compound F
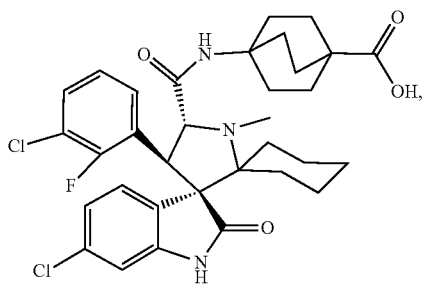
Compound Y
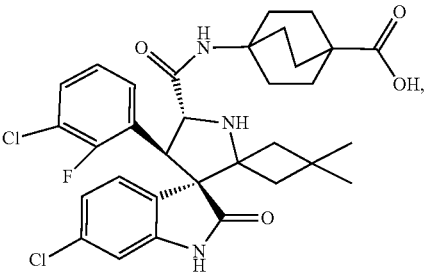
Compound K
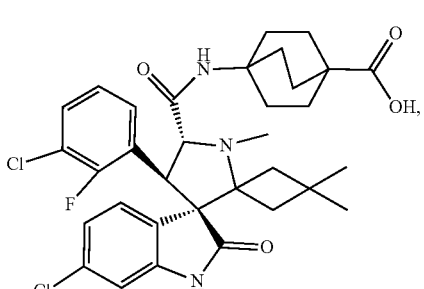
Compound P
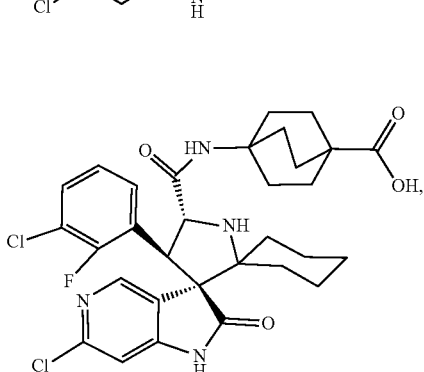
Compound T
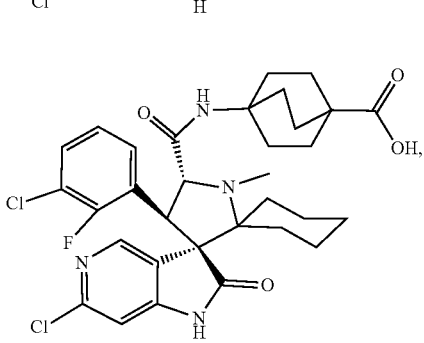

-continued

Compound S

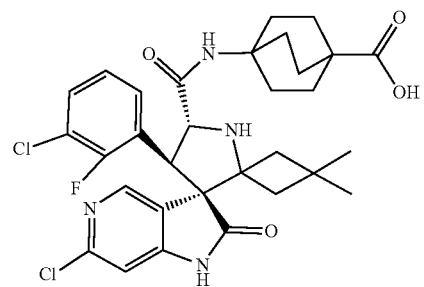

and

Compound W

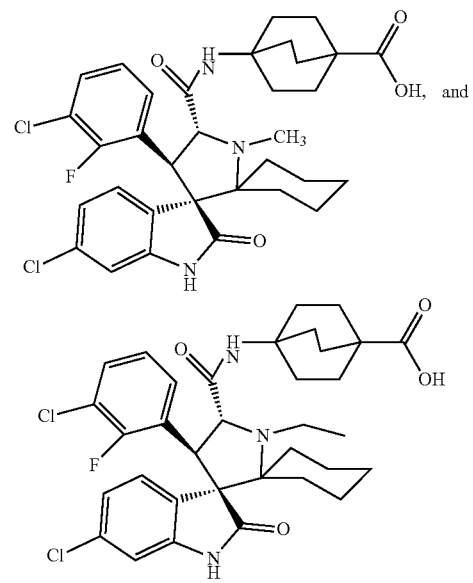

or a pharmaceutically acceptable salt thereof.

In certain embodiments, the MDM2 inhibitor is pharmaceutically acceptable salt.

In certain embodiments, the MDM2 inhibitor is Compound C, or a pharmaceutically acceptable salt.

In yet another aspect, the present disclosure provides a kit for use in the method described herein. In one embodiment, the kit comprises one or more reagents for measuring a level of at least one biomarker comprising Noxa. In one embodiment, the kit comprises one or more reagents for measuring a level of at least one biomarker comprising ASCL1. In one embodiment, the kit comprises one or more reagents for measuring a level of at least one biomarker comprising both Noxa and ASCL1.

In certain embodiments, the reagent for measuring the level of Noxa comprises a primer or a probe that can hybridize to the polynucleotide of Noxa, or an antibody that can specifically bind to the protein of Noxa. In certain embodiments, the reagent for measuring the level of ASCL1 comprises a primer or a probe that can hybridize to the polynucleotide of ASCL1, or an antibody that can specifically bind to the protein of ASCL1. In certain embodiments, the one or more reagents comprises a first primer or a first probe that can hybridize to the polynucleotide of Noxa, or a first antibody that can specifically bind to the protein of Noxa, and a second primer or a second probe that can hybridize to the polynucleotide of ASCL1, or a second antibody that can specifically bind to the protein of ASCL1.

In certain embodiments, one or more reagents is/are detectable labelled

In another aspect, the present disclosure provides use of one or more reagents for measuring level of at least one biomarker comprising Noxa, ASCL1 or both in the manufacture of a diagnostic kit for performing the method described herein. In one embodiment, the at least one biomarker comprises Noxa. In one embodiment, the at least one biomarker comprises ASCL1. In one embodiment, the at least one biomarker comprises both Noxa and ASCL1.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 6 shows exemplary sequences of the biomarkers as provided herein.

DETAILED DESCRIPTION OF THE INVENTION

Figure 1A:
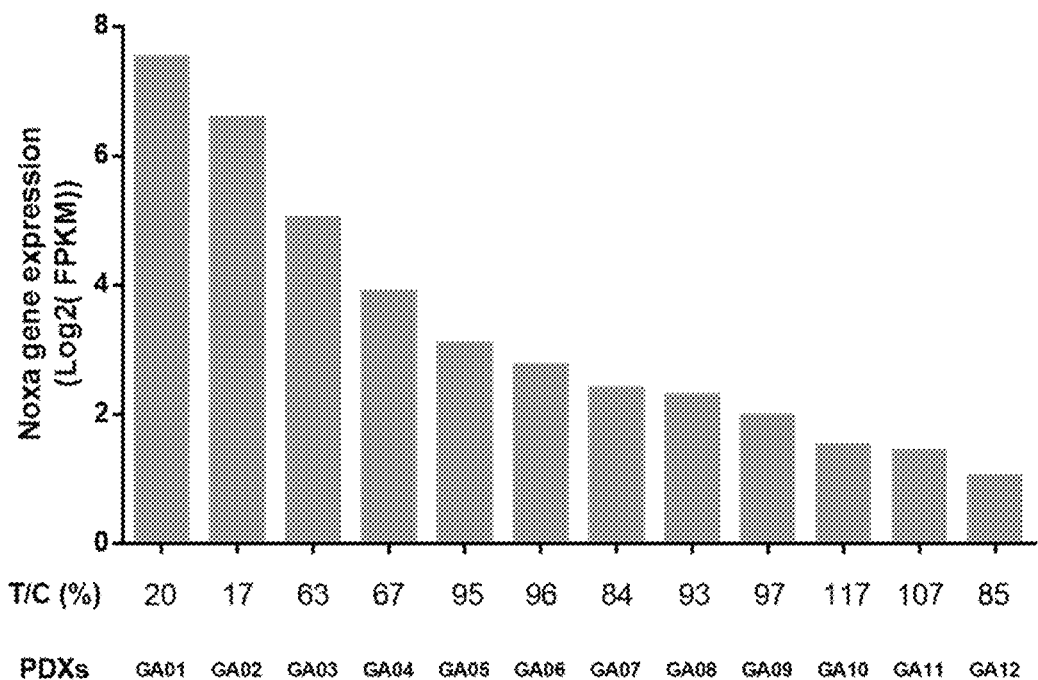
FIGS. 1A and 1B illustrate that Noxa expression level correlates with tumor regression in gastric cancer PDX (patients derived xenograft) models treated with Bcl-2/Bcl-xL dual inhibitor Compound A15.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definitions

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

The term "biomarker" as used here refers to a biological molecule that is a measurable indicator of some biological state or condition. The term "biomarker" used herein is intended to encompass both a polynucleotide of interest, a polypeptide for example encoded by the polynucleotide of interest. Example of biomarker provided herein can be a gene (e.g. genomic DNA, cDNA) or a product of the gene such as an mRNA transcribed from the gene, or a protein encoded by the gene. Examples of specific biomarkers provided herein include, for example, Noxa, and ASCL1.

The term "level" with respect to a biomarker, refers to the amount or quantity of the biomarker of interest present in a sample. Such amount or quantity may be expressed in the absolute terms, i.e., the total quantity of the biomarker in the sample, or in the relative terms, i.e., the concentration or percentage of the biomarker in the sample. Level of a biomarker can be measured at DNA level (for example, as represented by the amount or quantity or copy number of the gene in a chromosomal region), at RNA level (for example as mRNA amount or quantity), or at protein level (for example as protein amount or quantity or protein complex amount or quantity).

It is noted that in this disclosure, terms such as "comprises", "comprised", "comprising", "contains", "containing" and the like are intended to be inclusive or open-ended, and do not exclude additional, un-recited elements or method steps.

The terms "determining", "measuring" and "detecting" can be used interchangeably and refer to both quantitative and semi-quantitative determinations.

The term "hybridizing" refers to the binding, duplexing or pairing of at least partially complementary strands of nucleic acid molecules. A nucleic acid strand can specifically hybridize to a target nucleic acid strand when there is sufficient degree of complementarity to avoid non-specific binding to non-target nucleic acid sequences. An extensive guide to the hybridization of nucleic acids is found in, e.g., Tijssen *Laboratory Techniques in Biochemistry and Molecular Biology—Hybridization with Nucleic Acid Probes part I.* Ch. 2. "Overview of principles of hybridization and the strategy of nucleic acid probe assays." (1993) Elsevier, N.Y.

The term "nucleic acid" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "complementarity" refers to the ability of base-paring between a nucleic acid sequence and another nucleic acid sequence via either traditional Watson-Crick or other non-traditional types. Complementarity can be partial or total. Partial complementarity occurs when one or more nucleic acid bases is not matched according to the base pairing rules. A percent complementarity indicates the percentage of nucleic acid base in a nucleic acid molecule which can form basepairs (e.g., Watson-Crick base pairing) with a second nucleic acid sequence (e.g., 5, 6, 7, 8, 9, 10 base pairing out of 10 bases being 50%, 60%>, 70%>, 80%>, 90%, and 100% complementary).

In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

As used herein, "likelihood" and "likely" with respect to response of a subject to a treatment is a measurement of how probable the therapeutic response is to occur in the subject. It may be used interchangeably with "probability". Likelihood refers to a probability that is more than speculation, but less than certainty. Thus, a therapeutic response is likely if a reasonable person using common sense, training or experience concludes that, given the circumstances, a therapeutic response is probable. In one embodiment, the term "likelihood" and "likely" denotes a chance in percent of how probable a therapeutic response is to occur. In some embodiments, a subject with cancer identified as "likely to respond" refers to a subject with cancer who has more than 30% chance, more than 40% chance, more than 50% chance, more than 60% chance, more than 70% chance, more than 80% chance, more than 90% chance of responding to the treatment with an Bcl-2/Bcl-xL inhibitor and Bcl-2 inhibitor or Bcl-xL inhibitor.

The term "responsive" or "responsiveness" as used in the context of a subject's therapeutic response to a cancer therapy, are used interchangeably and refer to a beneficial response of a subject to a treatment as opposed to unfavorable responses, i.e. adverse events. In a subject, beneficial response can be expressed in terms of a number of clinical parameters, including loss of detectable tumor (complete response), decrease in tumor size and/or cancer cell number (partial response), tumor growth arrest (stable disease), tumor growth rate reduction which prolongs overall survival, enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/or cancer cell number (without any growth rate reduction that benefits overall survival), and/or tumor metastasis is indicative of lack of beneficial response to treatment, and therefore decreased responsiveness.

As described herein, the term "effective amount" refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce Bcl-2/Bcl-xL signaling in the target cells; and/or relieve, to some extent, one or more of the symptoms As used herein, "cancer" is a generic name for a wide range of cellular malignancies characterized by unregulated growth, lack of differentiation, and the potential or ability to invade local tissues and metastasize. These neoplastic malignancies affect, with various degrees of prevalence, every tissue and organ in the body. Cancer involves presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone or may circulate in the blood stream as independent cells, such as leukemic cells. The term cancer and tumor can be used interchangeably herein. The term includes all known cancers and neoplastic conditions, whether characterized as malignant, benign, hematologic or solid, and cancers of all stages and grades including pre- and post-metastatic cancers.

The term "solid tumor" as used herein refers to any cancer that does not contain cysts or liquid areas. Solid tumor generally does not include leukemias (i.e. blood cancer). Solid tumor can be benign or malignant. As used herein, types of solid tumor include, without limitation, adrenocortical carcinoma, anal cancer, astrocytoma, childhood cerebellar or cerebral, basal-cell carcinoma, bile duct cancer, bladder cancer (e.g. urinary bladder cancer), bone tumor, brain cancer, cerebellar astrocytoma, cerebral astrocytoma/malignant glioma, ependymoma, medulloblastoma, supratentorial primitive neuroectodermal tumors, visual pathway and hypothalamic glioma, breast cancer, Burkitt's lymphoma, cervical cancer, colon cancer, emphysema, endometrial cancer, esophageal cancer, Ewing's sarcoma, retinoblastoma, gastric (stomach) cancer, glioma, head and neck cancer, heart cancer, Hodgkin lymphoma, islet cell carcinoma (endocrine pancreas), Kaposi sarcoma, kidney cancer (renal cell cancer), laryngeal cancer, liver cancer (e.g. hepatocellular carcinoma), lung cancer (such as small cell lung cancer, non-small cell lung cancer, lung adenocarcinoma, lung squamous cell carcinoma), neuroblastoma, non-Hodgkin lymphoma, ovarian cancer, pancreatic cancer, gastro-intestinal cancer, pharyngeal cancer, prostate cancer, rectal cancer, renal cell carcinoma (kidney cancer), retinoblastoma, Ewing family of tumors, skin cancer, stomach cancer, testicular cancer, throat cancer, thyroid cancer, cholangiocarcinoma, vaginal cancer and small cell carcinoma (e.g. small cell lung cancer (SCLC), extrapulmonary small-cell carcinoma (EPSCC), small-cell carcinoma of the prostate, or small-cell carcinoma of the bladder), melanoma, cutaneous squamous cell carcinoma, glioblastoma, hysterocarcinoma, osteosarcoma, uterine cancer, uterine CS, colorectal cancer, cervical cancer, sarcoma, chromophobe, renal cell carcinoma (RCC), clear cell RCC, papillary RCC, uveal melanoma, testicular germ cell, low grade glioma (LGG), mesothelioma, PCPG, or thymoma.

As used herein, a "neuroendocrine cancer" is either one which arises from the neuroendocrine system, a diffuse system in which the nervous system and the hormones of the endocrine glands interact, or from non-endocrine cells by acquiring some of the properties of neuroendocrine cells through an oncogenic process such as Selective Tumor gene Expression of Peptides essential for Survival (STEPS) (see, North (2000) *Exper. Physiol.* 85S:27S-40S). Most of the well-described adult neuroendocrine tumors are distinctive and arise from a known primary site, including the carcinoid, pheochromocytoma, and Merkel's cell tumors. Carcinoid cancers include stomach, pancreas, colon, liver, lung, ovarian, breast, testicular, and cervical cancer. Pheochromocytoma is a cancer of the adrenal medulla, which often causes the adrenal glands to make too much catecholamine. Merkel's cell tumors are cancers that form on or just beneath the skin, but sometimes are also thought to arise from underlying soft tissue. They are also known as neuroendocrine cancer of the skin.

Examples of neuroendocrine cancer include, without limitation, small cell carcinoma, breast cancer, small cell lung cancer (SCLC), large cell neuroendocrine carcinoma of lung (LCNEC), thyroid tumor, gastric cancer, pancreatic cancer, mid-gut cancer, liver cancer, gallbladder cancer, ovarian cancer, cervical cancer, esophageal cancer, gastro-intestinal cancer, head and neck cancer, cholangiocarcinoma, pheophromocytoma, and Merkel's cell tumor.

As used herein, "small-cell carcinoma" refers to a type of highly malignant cancer characterized in a short doubling time, high growth fraction and early development of metastases. Small-cell carcinoma most commonly arises within the lung, and occasionally arise in other body sites, such as the cervix, prostate and gastrointestinal tract. Exemplary small cell carcinoma includes small-cell lung cancer, extrapulmonary small-cell carcinoma (EPSCC), small-cell carcinoma of the prostate, small-cell carcinoma of the bladder.

The term "hematological cancer" refers to any cancer that begins in blood-forming tissue such as the bone marrow, or in the cells of the immune system. In certain embodiments, the hematological cancer is chronic lymphocytic leukemia (CLL), acute myeloid leukemia (AML), T-cell prolymphocytic leukemia, multiple myeloma (MM), Waldenstrom macroglobulinemia (WM), acute lymphoblastic leukemia (ALL) or lymphoma (e.g., mantel cell lymphoma, diffuse large B cell lymphoma).

The term "sample" as used herein refers to a biological sample that is derived from a subject and contains one or more biomarker(s) of interest. Examples of sample include, without limitation, bodily fluid, such as blood, plasma, serum, urine, vaginal fluid, uterine or vaginal flushing fluids, pleural fluid, ascetic fluid, cerebrospinal fluid, saliva, sweat, tears, sputum, bronchioalveolar lavage fluid, etc., and tissues, such as biopsy tissue (e.g. biopsied bone tissue, bone marrow, breast tissue, gastroinstetinal tract tissue, lung tissue, liver tissue, prostate tissue, brain tissue, nerve tissue, meningeal tissue, renal tissue, endometrial tissue, cervical tissue, lymph node tissue, muscle tissue, or skin tissue), a paraffin embedded tissue. In certain embodiments, the sample can be a biological sample comprising cancer cells (including circulating cancer cells), or cells from the tissue surrounding or adjacent to a tumor. In some embodiments, the biological sample is a fresh or archived sample obtained from a tumor tissue or from a tissue surrounding or adjacent to a tumor, e.g., by a tumor biopsy or fine needle aspirate. In some embodiments, the sample can be any biological fluid containing cancer cells or suspected of containing cancer cells (e.g. in peripheral blood mononuclear cells (PBMC)). The collection of a sample from a subject is performed in accordance with the standard protocol generally followed by hospital or clinics, such as during a biopsy.

The term "test sample" as used herein refers to a sample derived from a subject in need of cancer treatment and is representative of the cancer condition of the subject. For example, the test sample can contain a cancer cell.

The term "control sample" as used herein refers to a sample that is otherwise comparable to the test sample except that it expresses the biomarker of interest at a reference level. Examples of a control sample include, without limitation, a reference cancer cell or tissue sample, or a healthy, non-cancer tissue sample, or a diploid, non-transformed, non-cancerous, genomically stable healthy human cell line, as long as they express the biomarker of interest at a reference level.

As used herein, the term "subject" refers to a human or any non-human animal (e.g., mouse, rat, rabbit, dog, cat, cattle, swine, sheep, horse or primate). In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "treating" or "treatment" of cancer as used herein, unless otherwise indicated, means reversing, alleviating, inhibiting the progress of, or preventing, either partially or completely, the growth of tumors, tumor metastases, or other cancer-causing or neoplastic cells in a subject.

The term "prognose" or "prognosing" as used herein refers to the prediction or forecast of the future course or outcome of a disease or condition.

As used herein, "co-administration" or "combination therapy" is understood as administration of two or more active agents using separate formulations or a single pharmaceutical formulation, or consecutive administration in any order such that, there is a time period while both (or all) active agents simultaneously exert their biological activities. It is contemplated herein that one active agent (e.g., a Bcl-2/Bcl-xL dual inhibitor or a Bcl-2 inhibitor or a Bcl-xL inhibitor) can improve the activity of a second agent, for example, can sensitize target cells, e.g., cancer cells, to the activities of the second agent. Co-administration does not require that the agents are administered at the same time, at the same frequency, or by the same route of administration.

As used herein, the term "alkyl" refers to straight chained and branched saturated $C_{1-10}$ hydrocarbon groups, including but not limited to methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethylbutyl.

The term $C_{m-n}$ means the alkyl group has "m" to "n" carbon atoms.

The term "alkylene" refers to an alkyl group having a substituent. An alkyl, e.g., methyl, or alkylene, e.g., —CH$_2$—, group can be substituted with one or more, and typically one to three, of independently selected halo, trifluoromethyl, trifluoromethoxy, hydroxy, alkoxy, nitro, cyano, alkylamino, or amino groups, for example.

The term "alkenyl" is defined identically as "alkyl," except for containing a carbon-carbon double bond, e.g., ethenyl, propenyl, and butenyl. The term "alkenylene" is defined identically to "alkylene" except for containing a carbon-carbon double bond. The term "alkynyl" and "alkynylene" are defined identically as "alkyl" and "alkylene" except the group contains a carbon-carbon triple bond.

As used herein, the term "halo" or "halogen" is defined as fluoro, chloro, bromo, or iodo.

The term "hydroxy" is defined as —OH.

The term "alkoxy" is defined as —O-alkyl.

The term "amino" is defined as —NH$_2$, and the term "alkylamino" refers to substituent groups wherein nitrogen is bound to at least one alkyl group. Examples include, NH-alkyl, N(alkyl)$_2$, or nitrogen bound to one alkyl group and one substituent group such as benzyl, phenethyl, among others.

The term "carbamoyl" refers to H2NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.

The term "carboxy" is defined as —C(=O)OH or a salt thereof.

The term "nitro" is defined as —NO$_2$.

The term "cyano" is defined as —CN.

The term "trifluoromethyl" is defined as —CF$_3$.

The term "trifluoromethoxy" is defined as —OCF$_3$.

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "heterocyclic" refers to a heteroaryl and heterocycloalkyl ring systems.

As used herein, the term "heteroaryl" refers to a monocyclic or bicyclic ring system containing one or two aromatic rings and containing at least one nitrogen, oxygen, or sulfur atom in an aromatic ring. Each ring of a heteroaryl group can contain one or two 0 atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "cycloalkyl" means a monocyclic or bicyclic, saturated or partially unsaturated, ring system containing three to eight carbon atoms, including cyclopropyl, cyclobutyl, cyclopentyl, cyclohexyl, cycloheptyl, and cyclooctyl, optionally substituted with one or more, and typically one to three, of independently selected halo, trifluoromethyl, trifluoromethoxy, hydroxy, alkoxy, nitro, cyano, alkylamino, or amino groups, for example.

As used herein, the term "heterocycloalkyl" means a monocyclic or a bicyclic, saturated or partially unsaturated, ring system containing 4 to 12 total atoms, of which one to five of the atoms are independently selected from nitrogen, oxygen, and sulfur and the remaining atoms are carbon. Non-limiting examples of heterocycloalkyl groups are azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, diazacycloheptyl, each optionally substituted with one or more, and typically one to three, of independently selected halo, $C_{1-6}$ alkyl, $C_{1-6}$ alkoxy, cyano, amino, carbamoyl, nitro, carboxy, $C_{2-7}$ alkenyl, $C_{2-7}$ alkynyl, or the like on an atom of the ring.

Biomarkers for Predicting Efficacy of MDM2 Inhibitor or Bcl-2/Bcl-xL Dual Inhibitor or Bcl-2 Inhibitor or Bcl-xL Inhibitor The methods and compositions described herein are based, in part, on the discovery of biomarkers whose level is predictive of the likelihood of a subject having cancer to respond to the treatment of compounds targeting apoptosis pathway, including MDM2 inhibitor or Bcl-2/Bcl-xL dual inhibitors or Bcl-2 inhibitors or Bcl-xL inhibitors. The biomarkers are also useful in predicting the therapeutic efficacy of compounds targeting apoptosis pathway, including MDM2 inhibitor or Bcl-2/Bcl-xL dual inhibitors or Bcl-2 inhibitors or Bcl-xL inhibitors in a subject having cancer.

i. Apoptosis Pathway and Compounds Targeting the Pathway

Apoptosis pathway includes multiple players in a complex network that orchestra together to regulate fate of the cells. Bcl-2 (B cell lymphoma protein 2) family proteins are the key regulators of apoptosis in the mitochondria-mediated (also called "intrinsic") pathway. Their activity is linked to the onset of lymphoid and several solid tumor cancers and is believed in many cancers to be the key mediator of resistance to chemotherapy. The Bcl-2 family of proteins are characterized in the structural homology domains BH1, BH2, BH3 and BH4, and can be further classified into three subfamilies depending on how many of the homology domains each protein contains or on its biological activity, i.e., whether it has anti-apoptotic (pro-survival) or pro-apoptotic (pro-death) function.

The first subgroup of Bcl-2 proteins contains proteins having all four homology domains, i.e., BH1, BH2, BH3 and BH4. Their general effect is anti-apoptotic, that is, to preserve a cell from starting a cell death process. Proteins such as Bcl-2, Bcl-w, Bcl-xL, Mcl-1, and Bfl-1/A1 are members of this first subgroup.

Proteins belonging to the second subgroup of Bcl-2 proteins contain the three homology domains BH1, BH2, and BH3, and have a pro-apoptotic effect. The two main representative proteins of this second subgroup are Bax and Bak.

The third subgroup of Bcl-2 proteins is composed of proteins containing only the BH3 domain and members of this subgroup are usually referred to as "BH3-only proteins." Their biological effect on the cell is pro-apoptotic. Bim, Bid, Bad, Bik, Noxa, Hrk, Bmf, and Puma are examples of this third subfamily of proteins.

The exact mechanism by which the Bcl-2 family proteins regulate cell death is not entirely known. In one hypothesis of regulation of cell death by Bcl-2 family proteins, the BH3-only proteins are further categorized as either "activator," e.g., Bim and Bid, or "sensitizer," e.g., Bad, Bik, Noxa, Hrk, Bmf, and Puma, depending on their regulatory function.

The activator BH3-only proteins bind to, and directly activate, pro-apoptotic proteins. These activators can also bind to and inhibit the anti-apoptotic Bcl-2 family proteins. This binding sequesters the activator proteins and prevents them from exerting their apoptotic activity.

Displacement of the activators by sensitizer peptides results in Bax/Bak-mediated apoptotic commitment. The sensitizer BH3-only proteins bind only to the anti-apoptotic Bcl-2 family proteins and block their anti-apoptotic functions. Each sensitizer protein can have a different specificity profile. For example, Noxa binds with high affinity to Mcl-1, BAD binds to Bcl-xL and Bcl-2 but only weakly to Mcl-1, and PUMA binds well to all three targets. These interactions can have various outcomes, including homeostasis, cell death, sensitization to apoptosis, and blockade of apoptosis.

The balance between anti-apoptotic (pro-survival) and pro-apoptotic (pro-death) proteins dictates the fate of the cell to live or die. Overexpression of pro-survival proteins, such as Bcl-2 and Bcl-xL, has been correlated with tumorigenesis and is a frequent cause of resistance to anticancer therapies (Vaux D L et al, Nature (1988) 335:440-42; Delbridge A R et al, Cell Death Differ (2015) 22:1071-80). Thus, agents designed to target the anti-apoptotic Bcl-2 family proteins, such as small-molecule BH3 mimetics, may provide new strategies for the treatment of cancer patients. Clinical available-inhibitors of anti-apoptotic Bcl-2 family proteins or BH3 mimetics including those undergoing clinical evaluation however showed limited efficacy in hematological cancer as well as solid tumor, possibly due to the complicated signaling pathways and tumor microenvironment.

Bcl-2/Bcl-xL dual inhibitors or Bcl-2 inhibitors or Bcl-xL inhibitors have been described previously as an anti-cancer therapeutic agent (See, e.g, PCT application WO2014113413A1, PCT/CN2019/098576, PCT/CN2019/086673, PCTUS2014011571 the entire contents of each of which are incorporated herein by reference), and are being evaluated in humans as mono-therapy or in combination with standard of care chemotherapy agents for treatment of diseases and conditions wherein inhibition of Bcl-2 family proteins activity provides a benefit.

As there are too many Bcl-2 family proteins involved in the apoptotic pathway, and the natural levels of these proteins can vary in different cell types, there is few biomarker that is generally applicable for predicting anti-cancer efficacy of a particular Bcl-2 inhibitor, a Bcl-xL inhibitor or a Bcl-2/Bcl-xL dual inhibitors.

Upstream the apoptosis pathway regulated by the Bcl-2 family proteins, the tumor suppressor p53 orchestras the cellular signals leading to apoptosis. p53 apparently promotes apoptosis through both transcription-dependent and -independent mechanisms that act in concert. For instance, the activation of p53 induces expression of specific apoptosis target genes that shifts the balance in the Bcl-2 family toward the pro-apoptosis members. The activation of p53 also allows its rapid translocation to the mitochondria that promotes the release of pro-apoptotic members from their sequestered states (McBride A. et al., Frontiers in Oncology, (2019) 9:192, Haupt S. et al., Journal of Cell Science, (2003) 116:4077). In addition to its regulation of apoptosis, activation of p53 also triggers cell cycle arrest or cellular senescence (Green D R, Nature, 2009; 458(7242):1127). Emerging evidence further suggests that p53 dysfunction fuels inflammation and supports tumor immune evasion and, thus, p53 dysfunction serves as an immunological driver of tumorigenesis (Guo G, Cancer Research, 2017; 77(9):2292). Thus, manipulation of p53 activity constitutes an attractive target for cancer therapy.

MDM2 (Murine Double Minute 2) is transcriptionally activated by p53, and MDM2, in turn, inhibits p53 activity by at least three mechanisms (Wu et al., Genes Dev. 7:1126 (1993)). First, MDM2 protein directly binds to the p53 transactivation domain, and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation. MDM2 and p53 are part of an auto-regulatory feed-back loop (Wu et al., Genes Dev. 7:1126 (1993)). "MDM2" as used herein is intended to encompass the MDM2 gene, as well as the MDM2 gene product (e.g. mRNA, protein). Exemplary sequence of human MDM2 is available under the NCBI accession number of ABT17086, ABT17084.1, ABT17085.1, or ABT17083.1.

MDM2 inhibitors interfere with the binding of MDM2 oncoprotein to the tumor suppressor p53 protein, and serves as a pharmacological p53 activator. MDM2 inhibitors have been described previously as an anti-cancer therapeutic agent (See, e.g, U.S. Pat. No. 9,745,314, the entire contents of which are incorporated herein by reference), and are being evaluated in humans as mono-therapy or in combination with standard of care chemotherapy agents for treatment of diseases and conditions wherein inhibition of MDM2 and MDM2-related proteins activity provides a benefit.

The MDM2 inhibitors disclosed in the present invention inhibit the interaction between p53 or p53-related proteins and MDM2 or MDM2-related proteins. By inhibiting the negative effect of MDM2 or MDM2-related proteins on p53 or p53-related proteins, the MDM2 inhibitors of the present invention sensitize cells to inducers of apoptosis and/or cell cycle arrest. In one embodiment, the MDM2 inhibitors of the present invention induce apoptosis and/or cell cycle arrest.

ii. Biomarkers

Biomarker have been identified herein to be capable of predicting likelihood of responsiveness, or therapeutics efficacy of compounds targeting the apoptosis pathway. Biomarkers provided herein include, Noxa, and ASCL1.

The term "Noxa" as used herein refers to Noxa gene and Noxa gene products such as mRNA of Noxa gene and protein encoded by Noxa gene. Noxa gene, also known as phorbol-12-myristate-13-acetate-induced protein 1 (PMA-induced protein 1, or PMAIP1) gene, immediate-early-response protein APR gene, adult T cell leukemia-derived PMA-responsive gene or APR gene, encodes a protein that promotes activation of caspases and apoptosis, at least partly by promoting mitochondrial membrane changes and efflux of apoptogenic protein from the mitochondria. Human Noxa gene has a Gene ID of 5366 in NCBI database. The mRNA transcript of the human Noxa gene has an NCBI reference sequence of NM_021127.2. The protein encoded by the human Noxa gene has an NCBI reference sequence of NP_066950.1. Exemplary sequences of Noxa are provided herein as SEQ ID NO: 8 (DNA sequence) and SEQ ID NO: 7 (protein sequence).

The term "ASCL1" as used herein refers to ASCL1 gene and ASCL1 gene products such as mRNA of ASCL1 gene and protein encoded by ASCL1 gene. ASCL1 gene, also known as Achaete-Scute Homolog 1 gene, Achaete-Scute Family BHLH Transcription Factor 1 gene, Class A Basic Helix-Loop-Helix Protein 46 gene, HASH1 gene, ASH1 gene, MASH1 gene, encodes a transcription factor that plays a key role in neuronal differentiation. Direct transcriptional targets of ASCL1 include Bcl2. Human ASCL1 gene has a Gene ID of 429 in NCBI database. The mRNA transcript of the human ASCL1 gene has an NCBI reference sequence of NM_004316.4. The protein encoded by the human ASCL1 gene has an NCBI reference sequence of NP_004307.2. Exemplary sequences of ASCL1 are provided herein as SEQ ID NO: 22 (DNA sequence) and SEQ ID NO: 21 (protein sequence).

ASCL1 is essential to neuronal differentiation, e.g. the proper development of neuroendocrine cells. Additionally, ASCL1 expression has been implicated in the growth and survival of neuroendocrine lung cancers (Augustyn, A., et al PNAS, 111: 14788-14793 (2014)). A recent study on small cell lung cancer (SCLC) proposed to define SCLC into four subtypes by different expression of four key transcription regulators, ASCL1, neurogenic differentiation factor (NeuroD1), yes-associated protein 1 (YAP1) and POU class 2 homeobox (POU2F3), wherein the expression of the four transcription regulators are essentially mutually exclusive and SCLC expressing ASCL1 makes up the greatest proportion (i.e. about 70%) of SCLC (Rudin, C M, et al, 19:289-297, (2019)).

The inventors of the present disclosure surprisingly found that the level of at least one biomarker comprising Noxa, or ASCL1, or both, is correlated to the therapeutic efficacy of MDM2 inhibitors or Bcl-2/Bcl-xL dual inhibitors or Bcl-2 inhibitor or Bcl-xL inhibitor.

In certain embodiments, the biomarker comprises Noxa gene comprising a gene sequence of SEQ ID NO: 8, or an mRNA encoded therefrom. In certain embodiments, the biomarker comprises Noxa protein comprising an amino acid sequence of SEQ ID NO: 7.

In certain embodiments, the biomarker comprises ASCL1 gene comprise a gene sequence of SEQ ID NO: 22, or an mRNA encoded therefrom. In certain embodiments, the biomarker comprises ASCL1 protein comprising an amino acid sequence of SEQ ID NO: 21.

Therefore, the present disclosure provides detection reagents for measuring the level of the at least one biomarker comprising Noxa, ASCL1 or both, and methods for identifying a subject with cancer as likely to respond to treatment with an MDM2 inhibitor or a Bcl-2/Bcl-xL dual inhibitor or Bcl-2 inhibitor or Bcl-xL inhibitor, methods for treating cancer in a subject in need thereof, and methods for monitoring therapeutic efficacy in a subject having cancer and having been treated with an MDM2 inhibitor or a Bcl-2/Bcl-xL dual inhibitor or a Bcl-2 inhibitor or a Bcl-xL inhibitor for a therapeutic period, based on the measured level of the at least one biomarker comprising Noxa, ASCL1 or both.

In some embodiments, the at least one biomarker further comprises one or more additional biomarkers selected from the group consisting of: Bcl-xL, Bcl-2, PUMA, Mcl-1, a protein complex comprising Bcl-xL, a protein complex comprising Bcl-2, and any combination thereof.

Exemplary sequences of Bcl-xL are provided herein as SEQ ID NO: 4 (DNA sequence) and SEQ ID NO: 3 (protein sequence). Exemplary sequences of Bcl-2 are provided herein as SEQ ID NOs: 2 and 14 (DNA sequence) and SEQ ID NOs: 1 and 13 (protein sequence). Exemplary sequences of PUMA are provided herein as SEQ ID NO: 10 (DNA sequence) and SEQ ID NO: 9 (protein sequence). Exemplary sequences of Mcl-1 are provided herein as SEQ ID NOs: 12, 18 and 20 (DNA sequence) and SEQ ID NOs: 11, 17 and 19 (protein sequence).

In some embodiments, the protein complex comprises Bcl-xL protein complexed with a BH3-only protein or with a BH3-domain containing protein. In some embodiments, the protein complex further comprises Bcl-2 protein complexed with a BH3-only protein, or with a BH3-domain containing protein.

In certain embodiments, the BH3-only protein is selected from the group consisting of: BIM, BID, BAD, BIK, HRK, BMF, and PUMA. In certain embodiments, BH3-only proteins can be selected from BIM and PUMA.

Exemplary sequences of BIM are provided herein as SEQ ID NOs: 6 and 16 (DNA sequence) and SEQ ID NOs: 5 and 15 (protein sequence).

In some embodiments, the protein complex comprises complexes selected from the group consisting of: Bcl-xL: BIM, Bcl-xL:PUMA, Bcl-2:BIM, Bcl-2:PUMA, and any combination thereof.

iii. Detection Reagents for the Biomarkers

In one aspect, the present disclosure provides detection reagents for detecting or measuring the level of the at least one biomarker comprising Noxa, ASCL1 or both. The measurement can be at RNA level, DNA level and/or protein level. Suitable reagents for detecting target RNA, target DNA or target proteins can be used.

In certain embodiments, the detection reagents comprise one or more primers or probes that can hybridize to the polynucleotide of Noxa, and/or one or more primers or probes that can hybridize to the polynucleotide of ASCL1. The term "primer" as used herein refers to oligonucleotides that can specifically hybridize to a target polynucleotide sequence, due to the sequence complementarity of at least part of the primer within a sequence of the target polynucleotide sequence. A primer can have a length of at least 8 nucleotides, typically 8 to 70 nucleotides, usually of 18 to 26 nucleotides. For proper hybridization to the target sequence, a primer can have at least 75%, at least 80%, at least 85%, at least 90%, or at least 95% sequence complementarity to the hybridized portion of the target polynucleotide sequence. Oligonucleotides useful as primers may be chemically synthesized according to the solid phase phosphoramidite triester method first described by Beaucage and Caruthers, *Tetrahedron Letts.* (1981) 22: 1859-1862, using an automated synthesizer, as described in Needham-Van Devanter et al, Nucleic Acids Res. (1984) 12:6159-6168.

Primers are useful in nucleic acid amplification reactions in which the primer is extended to produce a new strand of the polynucleotide. Primers can be readily designed by a skilled artisan using common knowledge known in the art, such that they can specifically anneal to the nucleotide sequence of the target nucleotide sequence of the at least one biomarker provided herein. Usually, the 3' nucleotide of the primer is designed to be complementary to the target sequence at the corresponding nucleotide position, to provide optimal primer extension by a polymerase.

The term "probe" as used herein refers to oligonucleotides or analogs thereof that can specifically hybridize to a target polynucleotide sequence, due to the sequence complementarity of at least part of the probe within a sequence of the target polynucleotide sequence. Exemplary probes can be, for example DNA probes, RNA probes, or protein nucleic acid (PNA) probes. A probe can have a length of at least 8 nucleotides, typically 8 to 70 nucleotides, usually of 18 to 26 nucleotides. For proper hybridization to the target sequence, a probe can have at least 75%, at least 80%, at least 85%, at least 90%, or at least 95% sequence complementarity to hybridized portion of the target polynucleotide sequence. Probes and also be chemically synthesized according to the solid phase phosphoramidite triester method as described above. Methods for preparation of DNA and RNA probes, and the conditions for hybridization thereof to target nucleotide sequences, are described in Molecular Cloning: A Laboratory Manual, J. Sambrook et al., eds., 2nd edition. Cold Spring Harbor Laboratory Press, 1989, Chapters 10 and 11.

In certain embodiments, the primes or probes provided herein comprise a polynucleotide sequence hybridizable to a portion within the sequence of SEQ ID NO: 8 or 22. In certain embodiments, the primes or probes provided herein comprise a polynucleotide sequence hybridizable to a portion within the sequence of SEQ ID NO: 2, 4, 6, 10, 12, 14, 16, 18 or 20. In certain embodiments, the primes or probes provided herein comprise a polynucleotide sequence having at least 60%, 65%, 70%, 75%, 80%, 85%, 90%, 95%, 97%, 98%, 99% or 100% complementarity to a portion within the sequence of SEQ ID NO: 8 or 22. In certain embodiments, the primes or probes provided herein comprise a polynucleotide sequence having at least 60%, 65%, 70%, 75%, 80%, 85%, 90%, 95%, 97%, 98%, 99% or 100% complementarity to a portion within the sequence of SEQ ID NO: 2, 4, 6, 10, 12, 14, 16, 18 or 20.

In certain embodiments, the detection reagents comprise one or more antibodies that can specifically bind to the protein of Noxa, and/or one or more antibodies that can specifically bind to the protein of ASCL1.

The term "antibody" as used herein refers to an immunoglobulin or an antigen-binding fragment thereof, which can specifically bind to a target protein antigen. Antibodies can be identified and prepared by selection of antibodies from libraries of recombinant antibodies in phage or similar vectors, as well as preparation of polyclonal and monoclonal antibodies by immunizing animals such as rabbits or mice (see, e.g., Huse et al., *Science* (1989) 246:1275-1281; Ward et al, *Nature* (1989) 341:544-546).

In certain embodiments, the antibodies provided herein comprise an antigen-binding region capable of specifically binding to an epitope within the protein or polypeptide having the sequence of SEQ ID NO: 7 or 21. In certain embodiments, the antibodies provided herein comprise an antigen-binding region capable of specifically binding to an epitope within the protein or polypeptide having the sequence of SEQ ID NO: 1, 3, 5, 9, 11, 13, 15, 17 or 19.

In certain embodiments, the primers, the probes and the antibodies provided herein are detectably labeled. Examples of the detectable label suitable for labeling primers, probes and antibodies include, for example, chromophores, radioisotopes, fluorophores, chemiluminescent moieties, particles (visible or fluorescent), nucleic acids, ligand, or catalysts such as enzymes.

Examples of radioisotopes include, without limitation, $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}M$, $^{212}Bi$, and $^{32}P$.

Examples of fluorophores include, without limitation, Acridine, 7-amino-4-methylcoumarin-3-acetic acid (AMCA), BODIPY, Cascade Blue, Cy2, Cy3, Cy5, Cy7, Edans, Eosin, Erythrosin, Fluorescein, 6-FAM, TET, JOC, HEX, Oregon Green, Rhodamine, Rhodol Green, Tamra. Rox, and Texas Red™ (Molecular Probes, Inc., Eugene, Oreg.).

Examples of enzymes include, without limitation, alkaline phosphatase, acid phosphatase, horseradish peroxidase, beta-galactosidase, and ribonuclease.

Examples of ligands include, without limitation, biotin, avidin, an antibody or an antigen.

It should be understood that it is not necessary for a detectable label to produce a detectable signal, for example, in some embodiments, it may can react with a detectable partner or react with one or more additional compounds to generate a detectable signal. For example, the detectable label can be a ligand capable of functioning as a specific binding pair member for a labeled ligand (e.g. a secondary labeled antibody). For another example, enzymes are useful a detectable labels due to their catalytic activity to catalyze chromo-, fluoro-, or lumo-genic substrate which results in generation of a detectable signal.

In certain embodiments, the detectably labeled primers, probes or antibodies as provided herein can further comprise a quencher substance. A quencher substance refers to a substance which, when present in sufficiently close proximity to a fluorescent substance, can quench the fluorescence emitted by the fluorescent substance as a result of, for example, fluorescence resonance energy transfer (FRET).

Examples of a quencher substance include, without limitation, Tamra, Dabcyl, or Black Hole Quencher (BHQ, Biosearch Technologies), DDQ (Eurogentec), Iowa Black FQ (Integrated DNA Technologies), QSY-7 (Molecular Probes), and Eclipse quenchers (Epoch Biosciences).

Primer and probes can be labeled to high specific activity by either the nick translation method or by the random priming method. Useful probe labeling techniques are described in the literature (Fan, Y-S, Molecular cytogenetics: protocols and applications, Humana Press, Totowa, N.J. xiv, 411 (2002)).

In certain embodiments, the one or more reagents comprises a primer or a probe that can hybridize to the polynucleotide of Noxa, or an antibody that can specifically bind to the protein of Noxa. In certain embodiments, the antibody provided herein comprise an antigen-binding region capable of specifically binding to an epitope within the protein or polypeptide having a sequence of SEQ ID NOs: 7.

In certain embodiments, the one or more reagents comprises a primer or a probe that can hybridize to the polynucleotide of ASCL1, or an antibody that can specifically bind to the protein of ASCL1. In certain embodiments, the antibody provided herein comprise an antigen-binding region capable of specifically binding to an epitope within the protein or polypeptide having a sequence of SEQ ID NOs: 21.

In certain embodiments, the one or more reagents comprises a first primer or a first probe that can hybridize to the polynucleotide of Noxa, or an antibody that can specifically bind to the protein of Noxa, and a second primer or a second probe that can hybridize to the polynucleotide of Noxa, or an second antibody that can specifically bind to the protein of Noxa. In certain embodiments, the first antibody provided herein comprise an antigen-binding region capable of specifically binding to an epitope within the protein or polypeptide having a sequence of SEQ ID NOs: 7, and the second antibody provided herein comprise an antigen-binding region capable of specifically binding to an epitope within the protein or polypeptide having a sequence of SEQ ID NOs: 21.

It can be understood that in certain embodiments, the antibodies are modified or labeled to be properly used in various detection assays. In certain embodiments, the antibody is detectably labeled. In certain embodiments, the antibody may comprise a capture moiety, or may be immobilized.

Examples of capture moiety can include for example binding partner or solid substrate, such as porous and non-porous materials, latex particles, magnetic particles, microparticles, strips, beads, membranes, microtiter wells and plastic tubes. The choice of solid phase material and method of detectably labeling the antigen or antibody reagent are determined based upon desired assay format performance characteristics. In certain embodiments, the antibody may be immobilized on a solid substrate. The immobilization can be via covalent linking or non-covalent attachment (e.g. coating).

Methods for Patient Identification, Treatment Guidance and Prognosis

In another aspect, the present disclosure provides a method for identifying a subject having cancer as likely to respond to treatment with an MDM2 inhibitor or a Bcl-2/Bcl-xL dual inhibitor or a Bcl-2 inhibitor or a Bcl-xL inhibitor. In certain embodiments, the method comprises: measuring level of at least one biomarker comprising Noxa, or ASCL1, or both in a test sample derived from the subject; comparing the level of the at least one biomarker with a corresponding reference level of the at least one biomarker to determine difference from the reference level; and determining that the subject is likely to respond to the treatment with the MDM2 inhibitor or Bcl-2/Bcl-xL dual inhibitor or Bcl-2 inhibitor or Bcl-xL inhibitor when the difference reaches a predetermined threshold.

In another aspect, the present disclosure provides a method for treating cancer in a subject in need thereof. In certain embodiments, the method comprises: measuring level of at least one biomarker comprising Noxa, or ASCL1, or both, in a sample derived from the subject; comparing the level of the at least one biomarker with a corresponding reference level of the at least one biomarker to determine difference from the reference level; and administering an effective amount of MDM2 inhibitor or Bcl-2/Bcl-xL dual inhibitor or Bcl-2 inhibitor or Bcl-xL inhibitor to the subject when the difference reaches a predetermined threshold.

In another aspect, the present disclosure provides a method for monitoring therapeutic efficacy or prognosing in a subject having cancer and having been treated with an MDM2 inhibitor or a Bcl-2/Bcl-xL dual inhibitor or a Bcl-2 inhibitor or Bcl-xL inhibitor for a therapeutic period. In certain embodiments, the method comprises: obtaining a test sample from the subject after the therapeutic period; measuring a level of at least one biomarker comprising Noxa, in the test sample to obtain a post-treatment level of the at least one biomarker; comparing the post-treatment level with a baseline level of the at least one biomarker in the test sample derived from the subject before the therapeutic period, to determine post-treatment change in the level of the at least one biomarker. In certain embodiments, the method further comprises continuing administering the MDM2 inhibitor or Bcl-2/Bcl-xL dual inhibitor or Bcl-2 inhibitor or Bcl-xL inhibitor to the subject when the post-treatment change reaches a predetermined threshold. In certain embodiments, when the post-treatment change does not reach the predetermined threshold, increasing the dose of the MDM2 inhibitor or Bcl-2/Bcl-xL dual inhibitor or Bcl-2 inhibitor or Bcl-xL inhibitor to the subject, administering an effective amount of second anti-cancer therapeutic agent in combination to the MDM2 inhibitor or Bcl-2/Bcl-xL dual inhibitor or Bcl-2 inhibitor or Bcl-xL inhibitor to the subject, or discontinuing the administering the MDM2 inhibitor or Bcl-2/Bcl-xL dual inhibitor or Bcl-2 inhibitor or Bcl-xL inhibitor to the subject.

i. Sample Preparation

Any biological sample suitable for conducting the methods provided herein can be derived from the subject. In certain embodiments, the sample can be further processed by a desirable method for performing the measurement of the level of the at least one biomarker.

In certain embodiments, the method further comprises isolating or extracting cancer cell (such as circulating tumor cell) from the biological fluid sample (such as peripheral blood sample) or the tissue sample derived from the subject. The cancer cells can be separated by immunomagnetic separation technology such as that available from Immunicon (Huntingdon Valley, Pa.).

In certain embodiments, a tissue sample can be processed to perform in situ hybridization. For example, the tissue sample can be paraffin-embedded before fixing on a glass microscope slide, and then deparaffinized with a solvent, typically xylene.

In certain embodiments, the method further comprises isolating the nucleic acid from the sample, if RNA or DNA level of the biomarker is to be measured. Various methods of extraction are suitable for isolating the DNA or RNA from cells or tissues, such as phenol and chloroform extraction, and various other methods as described in, for example, Ausubel et al., *Current Protocols of Molecular Biology* (1997) John Wiley & Sons, and Sambrook and Russell, *Molecular Cloning: A Laboratory Manual* $3^{rd}$ ed. (2001).

Commercially available kits can also be used to isolate RNA, including for example, the NucliSens extraction kit (Biomerieux, Marcy l'Etoile, France), QIAamp mini blood kit, Agencourt Genfind™, Rneasy® mini columns (Qiagen), PureLink® RNA mini kit (Thermo Fisher Scientific), and Eppendorf Phase Lock Gels™. A skilled person can readily extract or isolate RNA or DNA following the manufacturer's protocol.

ii. Methods of Measuring Levels of the Biomarker

The methods of the present disclosure include measuring the level of at least one biomarker described herein in a sample derived from a subject having cancer or suspected of having cancer.

The biomarkers Noxa and/or ACSL1 (and optionally additional biomarkers including Bcl-xL, Bcl-2, PUMA, Mcl-1, a protein complex comprising Bcl-xL, a protein complex comprising Bcl-2) provided herein are intended to encompass different forms including mRNA, protein and also DNA (e.g. genomic DNA). Therefore, the level of the at least one biomarker can be measured by, RNA level (e.g. mRNA level), protein level or DNA level. The mRNA level and/or the protein level can also be referred to as expression level of the at least one biomarker. In certain embodiments, the protein complex is measured at protein level.

The RNA (e.g. mRNA) level or the DNA level of the at least one biomarker comprising Noxa, or ASCL1, or both, can be measured by any suitable nucleic acid assays known in the art, for example, a nucleic acid amplification assay, a nucleic acid hybridization assay, a nucleic acid sequencing assay, and other methods such as high performance liquid chromatography (HPLC) fragment analysis, capillary electrophoresis, and the like. Protein level of a biomarker can be measured by any methods known in the art, for example, without limitation, immunoassays. These methods are well-known in the art, and are described in detail below as exemplary illustration.

a) Amplification Assay

A nucleic acid amplification assay involves copying a target nucleic acid (e.g. DNA or RNA), thereby increasing the number of copies of the amplified nucleic acid sequence. Amplification may be exponential or linear. Exemplary nucleic acid amplification methods include, but are not limited to, amplification using the polymerase chain reaction ("PCR", see U.S. Pat. Nos. 4,683,195 and 4,683,202; PCR Protocols: A Guide To Methods And Applications (Innis et al., eds, 1990)), reverse transcriptase polymerase chain reaction (RT-PCR), quantitative real-time PCR (qRT-PCR); quantitative PCR, such as TaqMan®, nested PCR, ligase chain reaction (See Abravaya, K., et al., Nucleic Acids Research, 23:675-682, (1995), branched DNA signal amplification (see, Urdea, M. S., et al., AIDS, 7 (suppl 2):S11-S14, (1993), amplifiable RNA reporters, Q-beta replication (see Lizardi et al., *Biotechnology* (1988) 6: 1197), transcription-based amplification (see, Kwoh et al., *Proc. Natl. Acad. Sci. USA* (1989) 86: 1173-1177), boomerang DNA amplification, strand displacement activation, cycling probe technology, self-sustained sequence replication (Guatelli et al., *Proc. Natl. Acad. Sci. USA* (1990) 87:1874-1878), rolling circle replication (U.S. Pat. No. 5,854,033), isothermal nucleic acid sequence based amplification (NASBA), and serial analysis of gene expression (SAGE).

In some embodiments, to measure the mRNA level of the biomarker, the target RNA of the biomarker is reverse transcribed to cDNA before the amplification. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus thermophilus*. For example, one method which may be used to convert RNA to cDNA is the protocol adapted from the Superscript II Preamplification system (Life Technologies, GIBCO BRL, Gaithersburg, Md.; catalog no. 18089-011), as described by Rashtchian, A., PCR Methods Applic., 4:S83-S91, (1994).

In certain embodiments, the level of the at least one biomarker provided herein is quantified after the nucleic acid amplification assay. For example, the amplified products can be separated on an agarose gel and stained with ethidium bromide followed by detection and quantification using standard gel electrophoresis methods. Alternatively, the amplified products can be integrally labeled with a suitable detectable label (e.g. a radio- or fluorescence nucleotide) and then visualized using x-ray film or under the appropriate stimulating spectra.

In certain embodiments, the expression level of RNA (e.g. mRNA) or the copy number variation of DNA of the biomarkers is quantified during the nucleic acid amplification assay, which is also known as real-time amplification or quantitative amplification. Methods of quantitative amplification are disclosed in, e.g., U.S. Pat. Nos. 6,180,349; 6,033,854; and 5,972,602, as well as in, e.g., Gibson et al., *Genome Research* (1996) 6:995-1001; DeGraves, et al., *Biotechniques* (2003) 34(1): 106-10, 112-5; Deiman B, et al., *Mol Biotechnol*. (2002) 20(2): 163-79. Quantification is usually based on the monitoring of the detectable signal representing copies of the template in cycles of an amplification (e.g., PCR) reaction. Detectable signals can be generated by intercalating agents (e.g. SYBR GREEN™ and SYBR GOLD™) or labeled primer or labeled probes used during the amplification.

In certain embodiments, the labeled primer or labeled probe comprise a detectable label comprising a fluorophore. In certain embodiments, the labeled primer or labeled probe may further comprise a quencher substance. Presence of both a fluorophore and a quencher substance ("dual labeled") in one primer or probe could be helpful to provide for a self-quenching probe such as a TaqMan (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, PCR Method Appl., 4:357-362; Tyagi et al, 1996, Nature Biotechnology, 14:303-308; Nazarenko et al., 1997, Nucl. Acids Res., 25:2516-2521; U.S. Pat. Nos. 5,866,336 and 6,117,635). In an intact primer or probe, the quencher substance and the fluorophore are in close proximity, such that when the fluorophore is excited by irradiation, it transfers energy to the quencher substance in the same probe via fluorescence resonance energy transfer (FRET), thereby does not emit a signal.

In a quantitative amplification assay (such as real-time PCR), levels of the detected biomarker can be quantified using methods known in the art. For example, during the amplification, the fluorescence signal can be monitored and calculated during each PCR cycle. The threshold cycle, or Ct value can be further calculated. Ct value is the cycle at which fluorescence intersects a predetermined value. The Ct can be correlated to the initial amount of nucleic acids or number of starting cells using a standard curve. A standard curve is constructed to correlate the differences between the Ct values and the logarithmic level of the measured biomarker.

As a quality control measure, level of an internal control biomarker may be measured. The skilled artisan will understand that an internal control biomarker can be inherently present in the sample and its level can be used to normalize the measured level of the at least one biomarker comprising Noxa, ASCL1, or both, to offset any difference in the absolute amount of the sample.

b) Hybridization Assay

Nucleic acid hybridization assays use probes to hybridize to the target nucleic acid, thereby allowing detection of the target nucleic acid. Non-limiting examples of hybridization assay include Northern blotting, Southern blotting, in situ hybridization, microarray analysis, and multiplexed hybridization-based assays.

In certain embodiments, the probes for hybridization assay are detectably labeled. In certain embodiments, the nucleic acid-based probes for hybridization assay are unlabeled. Such unlabeled probes can be immobilized on a solid support such as a microarray, and can hybridize to the target nucleic acid molecules which are detectably labeled.

In certain embodiments, hybridization assays can be performed by isolating the nucleic acids (e.g. RNA or DNA), separating the nucleic acids (e.g. by gel electrophoresis) followed by transfer of the separated nucleic acid on suitable membrane filters (e.g. nitrocellulose filters), where the probes hybridize to the target nucleic acids and allows detection. See, for example, Molecular Cloning: A Laboratory Manual, J. Sambrook et al., eds., 2nd edition, Cold Spring Harbor Laboratory Press, 1989, Chapter 7. The hybridization of the probe and the target nucleic acid can be detected or measured by methods known in the art. For example, autoradiographic detection of hybridization can be performed by exposing hybridized filters to photographic film. Densitometric scanning of the photographic films exposed by the hybridized filters provides an accurate measurement of the target nucleic acid levels. Computer imaging systems can also be used to quantify the level of the biomarker.

In some embodiments, hybridization assays can be performed on microarrays. Microarrays provide a method for the simultaneous measurement of the levels of large numbers of target nucleic acid molecules. The target nucleic acids can be RNA, DNA, cDNA reverse transcribed from mRNA, or chromosomal DNA. The target nucleic acids can be allowed to hybridize to a microarray comprising a substrate having multiple immobilized nucleic acid probes arrayed at a density of up to several million probes per square centimeter of the substrate surface. The RNA or DNA in the sample is hybridized to complementary probes on the array and then detected by laser scanning. Hybridization intensities for each probe on the array are determined and converted to a quantitative value representing relative levels of the RNA or DNA. See, U.S. Pat. Nos. 6,040,138, 5,800, 992 and 6,020,135, 6,033,860, and 6,344,316.

Techniques for the synthesis of these arrays using mechanical synthesis methods are described in, e.g., U.S. Pat. No. 5,384,261. Although a planar array surface is often employed the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789, 162, 5,708,153, 6,040,193 and 5,800,992. Arrays may be packaged in such a manner as to allow for diagnostics or other manipulation of an all-inclusive device. Useful microarrays are also commercially available, for example, microarrays from Affymetrix, from Nano String Technologies, QuantiGene 2.0 Multiplex Assay from Panomics.

In certain embodiments, hybridization assays can be in situ hybridization assay. In situ hybridization assay is useful to detect the presence of copy number variation (e.g. increase or amplification) at the locus of the biomarker of interest (e.g. Noxa, or ASCL1, or both). Probes useful for in situ hybridization assay can be locus specific probes, which hybridize to a specific locus on a chromosome to detect the presence or absence of a specific locus of interest (e.g. Noxa, or ASCL1, or both). Other types of probes may also be useful, for example, chromosome enumeration probes (e.g. hybridizable to a repeat sequence region in a chromosomal of interest to indicate presence or absence of the entire chromosome), and chromosome arm probes (e.g. hybridizable to a chromosomal region and indicate the presence or absence of an arm of a specific chromosome). Methods for use of unique sequence probes for in situ hybridization are described in U.S. Pat. No. 5,447,841, incorporated herein by reference. Probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems. Alternatively, techniques such as flow cytometry can be used to examine the hybridization pattern of the probes.

c) Sequencing Methods

Sequencing methods useful in the measurement of the level of biomarker of interest involves sequencing of the target nucleic acid and enumeration of the sequenced target nucleic acid. Examples of sequence methods include, without limitation, RNA sequencing, pyrosequencing, and high throughput sequencing.

High throughput sequencing involves sequencing-by-synthesis, sequencing-by-ligation, and ultra-deep sequencing (such as described in Marguiles et al., Nature 437 (7057): 376-80 (2005)). Sequence-by-synthesis involves synthesizing a complementary strand of the target nucleic acid by incorporating labeled nucleotide or nucleotide analog in a polymerase amplification. Immediately after or upon successful incorporation of a label nucleotide, a signal of the label is measured and the identity of the nucleotide is recorded. The detectable label on the incorporated nucleotide is removed before the incorporation, detection and identification steps are repeated. Examples of sequence-by-synthesis methods are known in the art, and are described for example in U.S. Pat. Nos. 7,056,676, 8,802,368 and 7,169,560, the contents of which are incorporated herein by reference. Sequencing-by-synthesis may be performed on a solid surface (or a microarray or a chip) using fold-back PCR and anchored primers. Target nucleic acid fragments can be attached to the solid surface by hybridizing to the anchored primers, and bridge amplified. This technology is used, for example, in the Illumina® sequencing platform.

Pyrosequencing involves hybridizing the target nucleic acid regions to a primer and extending the new strand by sequentially incorporating deoxynucleotide triphosphates corresponding to the bases A, C, G, and T (U) in the presence of a polymerase. Each base incorporation is accompanied by release of pyrophosphate, converted to ATP by sulfurylase, which drives synthesis of oxyluciferin and the release of visible light. Since pyrophosphate release is equimolar with the number of incorporated bases, the light given off is proportional to the number of nucleotides adding in any one step. The process is repeated until the entire sequence is determined.

In certain embodiments, the level of the biomarkers described herein is measured by whole transcriptome sequencing, or RNA sequencing (e.g. RNA-Seq). The method of RNA sequencing has been described (see Wang Z, Gerstein M and Snyder M, Nature Review Genetics (2009) 10:57-63; Maher C A et al., Nature (2009) 458:97-101; Kukurba K & Montgomery S B, Cold Spring Harbor Protocols (2015) 2015(11): 951-969). In brief, mRNA extracted from a sample is reverse transcribed into cDNA and sheared into fragments. Fragments within proper length ranges are selected and ligated with sequencing adaptors, followed by amplification, sequencing, and mapping reads to a reference genome.

The protein level of the at least one biomarker comprising Noxa, or ASCL1, or both, can be measured by any suitable protein assays known in the art, for example immunoassays, mass spectrometry, 2-D gel electrophoresis, protein array, and the like. The level of protein complex comprising Bcl-xL and/or a protein complex comprising Bcl-2 can be measured by any suitable assays known in the art for measuring protein-protein interaction, see, in general, Protein-Protein Interactions: A Molecular Cloning Manual, 2nd ed., Golemis and Adams, ed., Cold Spring Harbor Laboratory Press (2005)). In certain embodiments, the protein-protein interaction assay is based on immunoassay or proximity assays. Suitable methods generally for example, meso scale discovery (MSD) advanced enzyme-linked immunosorbent assay (MSD-ELISA), standard complex ELSIA, proximity ligation assay (PLA), co-immunoprecipitation, immunoblotting assay, or cross-linking assay, etc.

d) Immunoassays

Immunoassays typically involves using antibodies that specifically bind to the target polypeptide or protein (e.g. the Noxa, or ASCL1) to detect or measure the presence or level of the target polypeptide or protein. Such antibodies can be obtained using methods known in the art (see, e.g., Huse et al., *Science* (1989) 246:1275-1281; Ward et al, *Nature* (1989) 341:544-546), or can be obtained from commercial sources. Examples of immunoassays include, without limitation, Western blotting, enzyme-linked immunosorbent assay (ELISA), enzyme immunoassay (EIA), radioimmunoassay (RIA), sandwich assays, competitive assays, immunofluorescent staining and imaging, immunohistochemistry (IHC), and fluorescent activating cell sorting (FACS). For a review of immunological and immunoassay procedures, see Basic and Clinical Immunology (Stites & Terr eds., $7^{th}$ ed. 1991). Moreover, the immunoassays can be performed in any of several configurations, which are reviewed extensively in Enzyme Immunoassay (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Terr, eds., $7^{th}$ ed. 1991).

Immunohistochemistry (IHC) demonstrates a cell or tissue constituent in situ by detecting specific antibody/aptamer-antigen interactions where the antibody/aptamer has been tagged with a detectable label. The detectable label may be a fluorescent dye, colloidal metal, hapten, radioactive marker, or more commonly an enzyme. Experimental samples include formalin-fixed, paraffin-embedded (FFPE) samples. Ideally, maximal signal strength along with minimal background or non-specific staining are required to give optimal antigen demonstration. IHC protocols are well known in the art; see, e.g., Immunocytochemical Methods and Protocols (second edition), edited by Lorette C. Javois, from Methods in Molecular Medicine, volume 115, Humana Press, 1999 (ISBN 0-89603-570-0).

In certain embodiments, the antibodies are detectably labeled, or are not labeled but can react with a second molecule which is detectably labeled (e.g. a detectably labeled secondary antibody). Other detection systems such as time-resolved fluorescence, internal-reflection fluorescence, amplification (e.g., polymerase chain reaction) and Raman spectroscopy are also useful.

In certain embodiments, the antibodies may be immobilized on a solid substrate. The immobilization can be via covalent linking or non-covalent attachment (e.g. coating). Examples of solid substrate include porous and non-porous materials, latex particles, magnetic particles, microparticles, strips, beads, membranes, microtiter wells and plastic tubes. The choice of solid phase material and method of detectably labeling the antigen or antibody reagent are determined based upon desired assay format performance characteristics.

The level of the target polypeptides or proteins can be determined, for example, by normalizing to an internal control value or to a standard curve.

The level of each of the biomarkers described herein can be normalized to a standard level for a standard marker. The standard level of the standard marker can be predetermined, determined concurrently, or determined after a sample is derived from the subject. The standard marker can be run in the same assay or can be a known standard marker from a previous assay. In the cases when the level of the biomarker is determined by sequencing assay (such as RNA sequencing), the level of the biomarkers can be normalized to the total reads of the sequencing.

Any of the assays and methods provided herein for the measurement of the level of the biomarker can be adapted or optimized for use in automated and semi-automated systems, or point of care assay systems. Examples of automated and semi-automated systems are described, e.g., in Hu et. al, Lab On a Chip 2017, 17(13): 2225, Song et. al., Anal Chem, 2019, 91(1); 388, and Rusling, et. al., Analyst 2010, 135 (10):2496.

iii. Comparing with a Corresponding Reference Level

The levels of a biomarker (e.g. optionally normalized) may then be compared with a corresponding reference level of the corresponding biomarker to determine difference from the reference level. The term "reference level" of the at least one biomarker (e.g. Noxa, or ASCL1, or both) as used herein refers to a level of the biomarker that is representative of a control level from normal subjects, or is representative of an average level of the biomarker in a general population of subjects having cancer. In certain embodiments, the reference level of the at least one biomarker (e.g. Noxa, or ASCL1, or both) is representative of an average level of the biomarker in a general population of subjects having cancer.

In certain embodiments, the reference level can be a typical level, a measured level, or a range of the level of the corresponding biomarker that would normally be observed in one or more healthy cell or tissue samples, or in one or more control (e.g. cancer) cell or tissue samples. In certain embodiments, the reference level can be an average level of the corresponding biomarker in a healthy subject population, or in a general population of subjects having cancer (e.g. in a general cancer patient population). A "general population of subjects having cancer" or a "general cancer patient population" as used herein, refers to a population of cancer subjects or patients having different kinds of cancers. For example, a general cancer patient population may be a group of at least three (four, five, six, seven, eight, nine, ten, or more) types of cancer patients, with some patients having the first type of cancer, some having the second type of cancer, some having the third type of cancer, and so on. For example, a general cancer patient population can be a population having all kinds of cancers or a variety of cancer types. In certain embodiments, the reference level can also be an empirical level considered representative of a general population of subjects having cancer. In certain embodiments, the reference level of the biomarkers described herein is obtained using the same or comparable measurement method or assay as used in the measurement of the level of the biomarker provided herein.

In certain embodiments, the reference level can be predetermined. For example, the reference level can be calculated or generalized based on measurements of the biomarker level in a collection of normal tissues or samples. For another example, the reference level can be based on statistics of the level of the biomarkers generally observed in comparable samples from a normal population.

In certain embodiments, the reference level can be tested in parallel with the level of the biomarker in the test sample. In certain embodiments, the reference level is measured in a control sample. In certain embodiments, the control sample is a normal tissue sample derived from the same subject or from a healthy subject. In certain embodiments, the control sample is derived from a control cancer patient. In certain embodiments, the control sample is a comparable sample from one or more healthy subjects, or from one or more cancer patients.

The level of the at least one biomarker in the test sample may exhibit a difference from the reference level in terms of elevation or reduction. Depending on the specific biomarker, one may seek elevation in one biomarker but reduction in another biomarker, in order to predict likelihood of responsiveness to the MDM2 inhibitor or Bcl-2/Bcl-xL inhibitor dual inhibitors or Bcl-2 inhibitors or Bcl-xL inhibitor according to the methods provided herein. The term "elevation" as used herein refers to levels of a biomarker as measured in the test sample is higher than the corresponding reference level of that biomarker. Similarly, "reduction" as used herein refer to levels of a biomarker as measured in the sample is lower than the corresponding reference level of that biomarker. The term "maintenance" as used herein refers to no significant change.

In certain embodiments, an elevation in level of Noxa is relevant to likelihood of responsiveness to the MDM2 inhibitor or Bcl-2/Bcl-xL dual inhibitors or Bcl-2 inhibitors or Bcl-xL inhibitors provided herein. In certain embodiments, an elevation in level of ASCL1 is relevant to likelihood of responsiveness to the MDM2 inhibitor or Bcl-2/Bcl-xL dual inhibitors or Bcl-2 inhibitors or Bcl-xL inhibitors provided herein. In certain embodiments, an elevation in level of Noxa and an elevation in level of ASCL1 is relevant to likelihood of responsiveness to the MDM2 inhibitor or Bcl-2/Bcl-X1 dual inhibitors or Bcl-2 inhibitors or Bcl-xL inhibitors provided herein.

In certain embodiments, levels of the at least one biomarkers (such as Bcl-xL, Bcl-2, Mcl-1, and/or a protein complex comprising Bcl-xL protein and/or a protein complex comprising Bcl-2) can be further considered, for example, to improve diagnostic sensitivity and specificity. For example, an elevation in level of Bcl-xL, an elevation in level of Bcl-2, maintenance to reduction in level of Mcl-1, and/or an elevation in level of a protein complex comprising Bcl-xL protein or Bcl-2 protein, is/are also relevant to the likelihood of responsiveness to the Bcl-2/Bcl-xL dual inhibitors provided herein. In certain embodiments, an elevation in level of Noxa, and/or an elevation in level of ASCL1, accompanied by either an elevation in level of Bcl-xL, an elevation in level of Bcl-2, maintenance to reduction in level of Mcl-1, or an elevation in level of a protein complex comprising Bcl-xL protein or Bcl-2 protein, is relevant to the likelihood of responsiveness to the MDM2 inhibitor or Bcl-2/Bcl-xL dual inhibitors or Bcl-2 inhibitors or Bcl-xL inhibitors provided herein.

In certain embodiments, the difference from the reference level is further compared with a predetermined threshold. In certain embodiments, a predetermined threshold can be set by statistical methods, such that if the difference from the reference level reaches the predetermined threshold, such difference can be considered statistically significant. Useful statistical analysis methods are described in L. D. Fisher & G. vanBelle, Biostatistics: A Methodology for the Health Sciences (Wiley-Interscience, N Y, 1993). Statistically significance can be determined based on confidence ("p") values, which can be calculated using an unpaired 2-tailed t test. A p value less than or equal to, for example, 0.1, 0.05, 0.025, or 0.01 usually can be used to indicated statistical significance. Confidence intervals and p-values can be determined by methods well-known in the art. See, e.g., Dowdy and Wearden, Statistics for Research, John Wiley & Sons, New York, 1983.

In certain embodiments, the predetermined threshold for the level of Noxa is at least 15%, at least 25%, at least 35%, at least 45%, or at least 50% elevation. "Percentage elevation" or "percentage higher" as used herein means that the percentage of the increment. For example, 100% elevations means that 100% increase from the reference level, which amounts to a total of 200% of that of the reference level. In other words, when the level of Noxa as measured in the test sample is at least 15%, at least 25%, at least 35%, at least 45%, or at least 50% higher than the corresponding reference level of Noxa, such measured level of Noxa in the test sample is considered significantly different from the reference level.

In certain embodiments, the predetermined threshold for the level of ASCL1 is at least 15%, at least 25%, at least 35%, at least 45%, or at least 50%, or at least 100% elevation. In other words, when the level of ASCL1 as measured in the test sample is at least 50%, at least 75%, at least 100%, at least 125%, or at least 150% higher than the corresponding reference level of ASCL1, such measured level of ASCL1 in the test sample is considered significantly different from the reference level.

Methods for Patient Identification and Treatment Guidance

In another aspect, the present disclosure provides a method for identifying a subject having cancer as likely to respond to treatment with an MDM2 inhibitor or a Bcl-2/Bcl-xL dual inhibitor or a Bcl-xL inhibitor or a Bcl-2 inhibitor. In one embodiment, the method comprises: measuring a level of at least one biomarker comprising Noxa, ASCL1, or Noxa and ASCL1, in a test sample derived from the subject; and comparing the level of the at least one biomarker with a corresponding reference level of the at least one biomarker to determine difference from the reference level; and identifying the subject as likely to respond to the treatment with the MDM2 inhibitor or Bcl-2/Bcl-xL dual inhibitor or Bcl-xL inhibitor or Bcl-2 inhibitor when the difference reaches a predetermined threshold.

In certain embodiments, if the difference does not reach a predetermined threshold, then the subject is identified as less likely to respond to the treatment with the MDM2 inhibitor or Bcl-2/Bcl-xL dual inhibitor or Bcl-2 inhibitor or Bcl-xL inhibitor. These identified subjects may be recommended to take additional tests to confirm the conclusion, or alternatively may be recommended not to be treated with the MDM2 inhibitor or Bcl-2/Bcl-xL dual inhibitor or Bcl-2 inhibitor or Bcl-xL inhibitor provided herein.

In certain embodiments, the methods provided herein further comprises administering an effective amount of the MDM2 inhibitor or Bcl-2/Bcl-xL dual inhibitor or Bcl-2 inhibitor or Bcl-xL inhibitor to the subject identified as likely to respond to the treatment with an MDM2 inhibitor or a Bcl-2/Bcl-xL dual inhibitor or a Bcl-2 inhibitor or a Bcl-xL inhibitor.

In certain embodiments, the methods provided herein further comprises administering an effective amount of second anti-cancer therapeutic agent in combination with the MDM2 inhibitor or Bcl-2/Bcl-xL dual inhibitor or Bcl-2 inhibitor or Bcl-xL inhibitor to the subject identified as likely to respond to the treatment with an MDM2 inhibitor or a Bcl-2/Bcl-xL dual inhibitor or a Bcl-2 inhibitor or a Bcl-xL inhibitor.

In another aspect, the present disclosure provides a method for treating cancer in a subject in need thereof. In certain embodiments, the method comprises: measuring level of at least one biomarker comprising Noxa, or ASCL1, or both, in a test sample derived from the subject; comparing the level of the at least one biomarker with a corresponding reference level of the at least one biomarker to determine difference from the reference level; and administering an effective amount of MDM2 inhibitor or Bcl-2/Bcl-xL dual inhibitor or a Bcl-2 inhibitor or a Bcl-xL inhibitor to the subject when the difference reaches a predetermined threshold.

In another aspect, the present disclosure provides a method for monitoring therapeutic efficacy in a subject having cancer and having been treated with an MDM2 inhibitor or a Bcl-2/Bcl-xL dual inhibitor or a Bcl-2 inhibitor or a Bcl-xL inhibitor for a therapeutic period. In certain embodiments, the method comprises: obtaining a test sample from the subject after the therapeutic period; measuring level of at least one biomarker comprising Noxa or ASCL1, or both, in the test sample to obtain a post-treatment level of the at least one biomarker; comparing the post-treatment level with a baseline level of the at least one biomarker in the test sample derived from the subject before the therapeutic period, to determine post-treatment change in the level of the at least one biomarker. If the post-treatment difference still reaches the predetermined threshold, then the subject is identified as still responsive to the treatment with the MDM2 inhibitor or Bcl-2/Bcl-xL dual inhibitor or Bcl-2 inhibitor or Bcl-xL inhibitor. Alternatively, if the post-treatment difference does not reach the predetermined threshold, then the subject is identified as having reduced responsiveness or no longer responsive to the MDM2 inhibitor or Bcl-2/Bcl-xL dual inhibitor or Bcl-2 inhibitor or Bcl-xL inhibitor provided herein.

In certain embodiments, the method further comprises continuing administering the MDM2 inhibitor or Bcl-2/Bcl-xL dual inhibitor or Bcl-2 inhibitor or Bcl-xL inhibitor to the subject when the difference reaches a predetermined threshold. In certain embodiments, when the difference does not reach the predetermined threshold, the method further comprises: administering an effective amount of second anti-cancer therapeutic agent in combination to the MDM2 inhibitor or Bcl-2/Bcl-xL dual inhibitor or Bcl-2 inhibitor or Bcl-xL inhibitor to the subject, or discontinuing the administering the MDM2 inhibitor or Bcl-2/Bcl-xL dual inhibitor or Bcl-2 inhibitor or Bcl-xL inhibitor to the subject.

In certain embodiments, the at least one biomarker further comprises Bcl-xL, Bcl-2, PUMA, Mcl-1, a protein complex comprising Bcl-xL, or any combination thereof. A reduction in the post-treatment level of Noxa (and optionally Bcl-2, Bcl-xL) in the sample indicates likelihood of decreased responsiveness to the treatment with the MDM2 inhibitor or Bcl-2/Bcl-xL dual inhibitor or Bcl-2 inhibitor or Bcl-xL inhibitor. In certain embodiments, an elevation in the post-treatment level of Mcl1 in the sample indicates likelihood of decreased responsiveness to the treatment with the MDM2 inhibitor or Bcl-2/Bcl-xL dual inhibitor or Bcl-2 inhibitor or Bcl-xL inhibitor.

Bcl-2/Bcl-xL Dual Inhibitors or Bcl-2 Inhibitors or Bcl-xL Inhibitors

In certain embodiments, the Bcl-2/Bcl-xL dual inhibitor described herein is a compound having a structural formula (I), (II) or (III):

or a pharmaceutically acceptable salt of (I), (II) or (III); wherein the A ring is

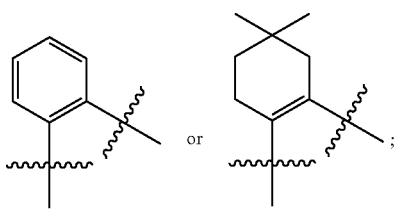

X, substituted or unsubstituted, is selected from the group consisting of alkylene, alkenylene, cycloalkylene, cycloalkenylene, and heterocycloalkylene;

(I)

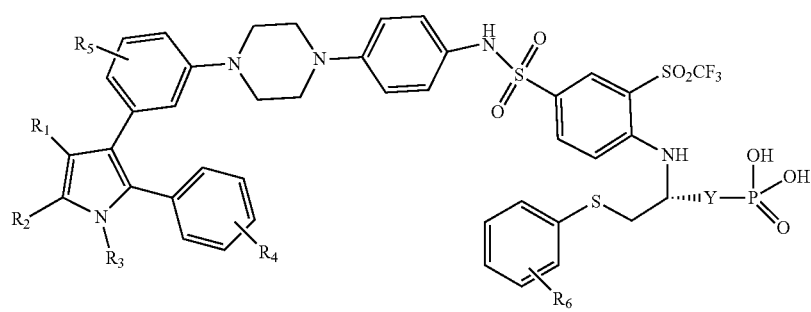

(II)

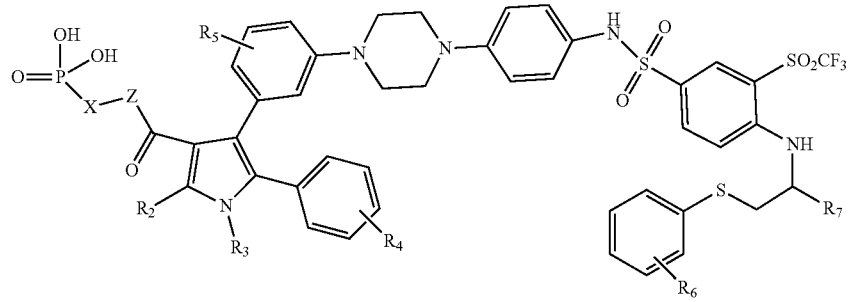

(III)

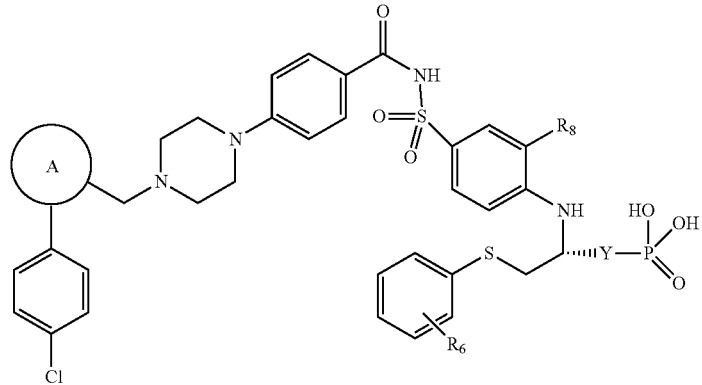

Y is selected from the group consisting of $(CH_2)_n$—$N(R^a)_2$ and

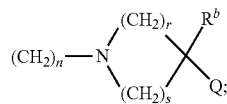

Q is selected from the group consisting of O, $O(CH_2)_{1-3}$, $NR^c$, $NR^c(C_{1-3}alkylene)$, $OC(=O)(C_{1-3}alkylene)$, $C(=O)O$, $C(=O)O(C_{1-3}alkylene)$, $NHC(=O)(C_{1-3}alkylene)$, $C(=O)NH$, and $C(=O)NH(C_{1-3}alkylene)$;

Z is O or $NR^c$;

$R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", COR', $CO_2R'$, OCOR', CONR'R", CONR'$SO_2R$", NR'COR", NR'CONR"R'", NR'C=SNR"R'", NR'$SO_2R$", $SO_2R'$, and $SO_2NR'R"$;

$R_3$ is selected from a group consisting of H, alkyl, cycloalkyl, alkenyl, cycloalkenyl, alkynyl, aryl, heteroaryl, heterocycloalkyl, OR', NR'R", OCOR', $CO_2R'$, COR', CONR'R", CONR'$SO_2R$", $C_{1-3}$alkyleneCH(OH)CH$_2$OH, $SO_2R'$, and $SO_2NR'R"$;

R', R", and R'", independently, are H, alkyl, cycloalkyl, alkenyl, cycloalkenyl, alkynyl, aryl, heteroaryl, $C_{1-3}$alkyleneheterocycloalkyl, or heterocycloalkyl;

R' and R", or R" and R'", can be taken together with the atom to which they are bound to form a 3 to 7 membered ring;

$R_4$ is hydrogen, halo, $C_{1-3}$alkyl, $CF_3$, or CN;

$R_5$ is hydrogen, halo, $C_{1-3}$alkyl, substituted $C_{1-3}$alkyl, hydroxyalkyl, alkoxy, or substituted alkoxy;

$R_6$ is selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", CONR'$SO_2R$", NR'COR", NR'CONR"R'", NR'C=SNR"R'", NR'$SO_2R$", $SO_2R'$, and $SO_2NR'R"$;

$R_7$, substituted or unsubstituted, is selected form the group consisting of hydrogen, alkyl, alkenyl, $(CH_2)_{0-3}$cycloalkyl, $(CH_2)_{0-3}$cycloalkenyl, $(CH_2)_{0-3}$heterocycloalkyl, $(CH_2)_{0-3}$aryl, and $(CH_2)_{0-3}$heteroaryl;

$R_a$ is selected form the group consisting of hydrogen, halo, $NO_2$, CN, $CF_3SO_2$, and $CF_3$;

$R_a$ is selected from the group consisting of hydrogen, alkyl, heteroalkyl, alkenyl, hydroxyalkyl, alkoxy, substituted alkoxy, cycloalkyl, cycloalkenyl, and heterocycloalkyl;

$R_b$ is hydrogen or alkyl;

$R_c$ is selected from the group consisting of hydrogen, alkyl, substituted alkyl, hydroxyalkyl, alkoxy, and substituted alkoxy; and n, r, and s, independently, are 1, 2, 3, 4, 5, or 6.

In certain embodiments, the Bcl-2/Bcl-xL dual inhibitor described herein is a compound having a structure of formula (IV):

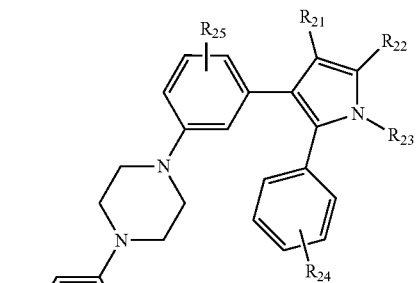
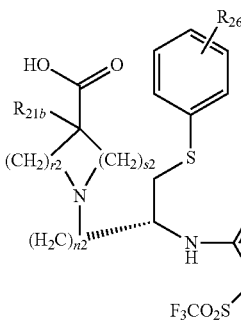

(IV)

or a pharmaceutically acceptable salt of (IV);

$R_{21}$ is $SO_2R_2'$;

$R_{22}$ is alkyl, preferably $C_1$-$C_4$ alkyl, more preferably methyl, propyl, or isopropyl;

$R_{23}$ is alkyl, preferably $C_1$-$C_4$ alkyl, more preferably methyl, propyl, or isopropyl;

$R_{24}$ is halogen, preferably fluoride, chloride;

$R_{25}$ is halogen, preferably fluoride, chloride;

$R_{26}$ is selected from H, halogen, alkyl, preferably fluoride, chloride, $C_1$-$C_4$ alkyl, more preferably methyl, propyl, isopropyl;

$R_{21b}$ is H or alkyl, preferably $C_1$-$C_4$ alkyl, more preferably methyl, propyl, or isopropyl;

$n_2$, $r_2$ and $s_2$ are independently 1, 2, 3, 4, 5 or 6, more preferably, $r_2$ and $s_2$ are both 2 and $n_2$ is 3, 4 or 5, more preferably, all of $n_2$, $r_2$ and $s_2$ are 2; and $R_2'$ is alkyl, preferably $C_1$-$C_4$ alkyl, more preferably methyl, propyl, or isopropyl.

In certain embodiments, the Bcl-2 inhibitor described herein is a compound having a structure of formula (V):

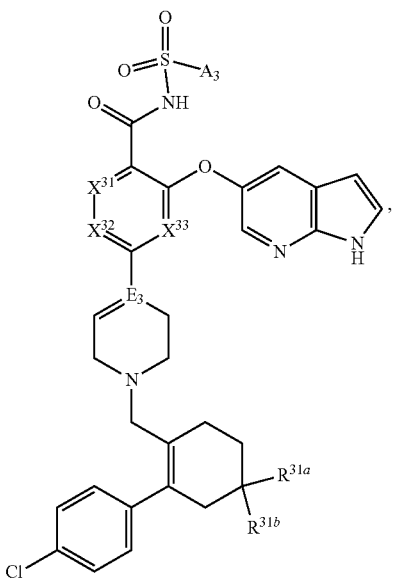

(V)

or a pharmaceutically acceptable salt of (V);
A₃ is selected from the group consisting of:

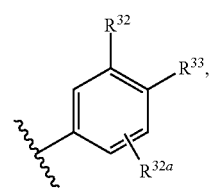

A-1

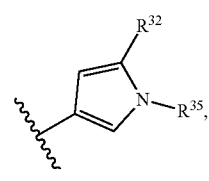

A-2

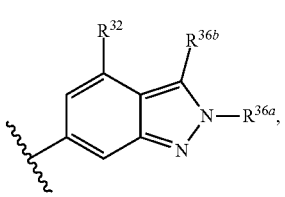

A-3

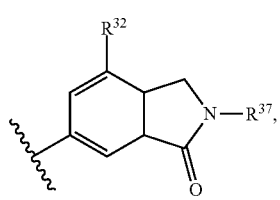

A-4

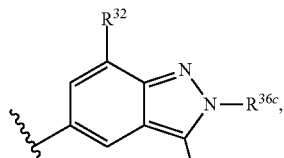

A-5

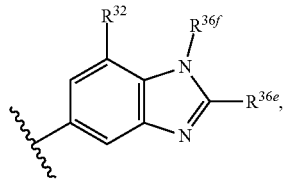

A-6

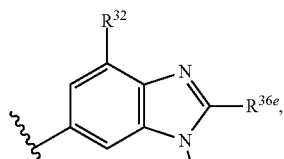

A-7

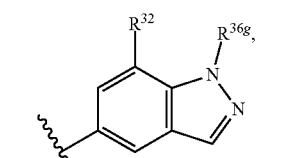

A-8

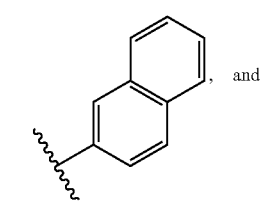

A-9

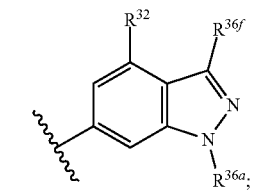

A-10

$E_3$ is a carbon atom and === is a double bond; or
$E_3$ is a —C(H)— and === is a single bond; or
$E_3$ is a nitrogen atom and === is a single bond;
$X^{31}$, $X^{32}$, and $X^{33}$ are each independently selected from the group consisting of —CR³⁸= and —N=;
$R^{31a}$ and $R^{31b}$ taken together with the carbon atom to which they are attached form a 3-, 4-, or 5-membered optionally substituted cycloalkyl; or
$R^{31a}$ and $R^{31b}$ taken together with the carbon atom to which they are attached form a 4- or 5-membered optionally substituted heterocyclo;
$R^{32}$ is selected from the group consisting of —NO₂, —SO₂CH₃, and —SO₂CF₃;
$R^{32a}$ is selected from the group consisting of hydrogen and halogen;
$R^{33}$ is selected from the group consisting of hydrogen, —CN, —C≡CH, and —N(R³⁴ᵃ)(R³⁴ᵇ);

$R^{34a}$ is selected from the group consisting of optionally substituted $C_{1-6}$ alkyl, optionally substituted $C_{3-6}$ cycloalkyl, heterocyclo, heteroalkyl, (cycloalkyl)alkyl, and (heterocyclo)alkyl;

$R^{34}$ is selected from the group consisting of hydrogen and $C_{1-6}$ alkyl;

$R^{35}$ is selected from the group consisting of is selected from the group consisting of optionally substituted $C_{1-6}$ alkyl, heterocyclo, heteroalkyl, (cycloalkyl)alkyl, and (heterocyclo)alkyl;

$R^{36a}$, $R^{36c}$, $R^{36e}$, $R^{36f}$, and $R^{36g}$ are each independently selected from the group consisting of hydrogen, optionally substituted $C_{1-6}$ alkyl, optionally substituted $C_{3-6}$ cycloalkyl, optionally substituted aryl, optionally substituted heteroaryl, heterocyclo, heteroalkyl, (cycloalkyl)alkyl, and (heterocyclo)alkyl;

$R^{36b}$ and $R^{36d}$ are each independently selected from the group consisting of hydrogen, $C_{1-4}$ alkyl, and halogen;

$R^{37}$ is selected from the group consisting of optionally substituted $C_{1-6}$ alkyl, heterocyclo, heteroalkyl, (cycloalkyl)alkyl, and (heterocyclo)alkyl; and $R^{38}$ is selected from the group consisting of hydrogen and halogen.

In certain embodiments, the Bcl-2/Bcl-xL dual inhibitor described herein having a structural formula (I-III) is a compound selected from Table 1-A or a pharmaceutically acceptable salt of the compound.

TABLE 1-A

| Compound | Structure |
|---|---|
| A1 | 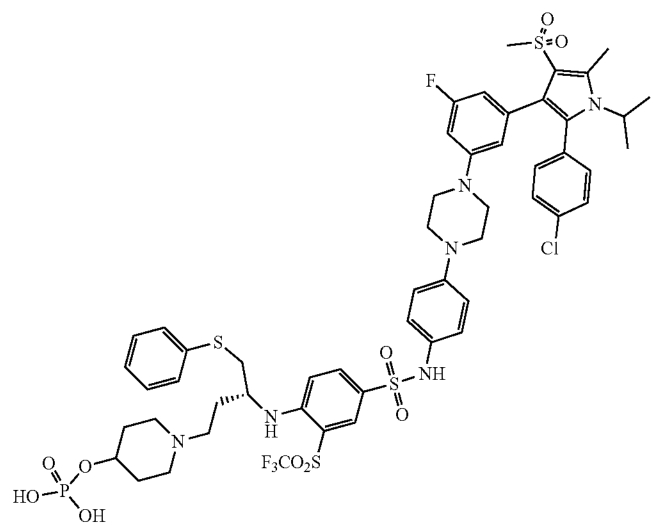 |
| A2 | 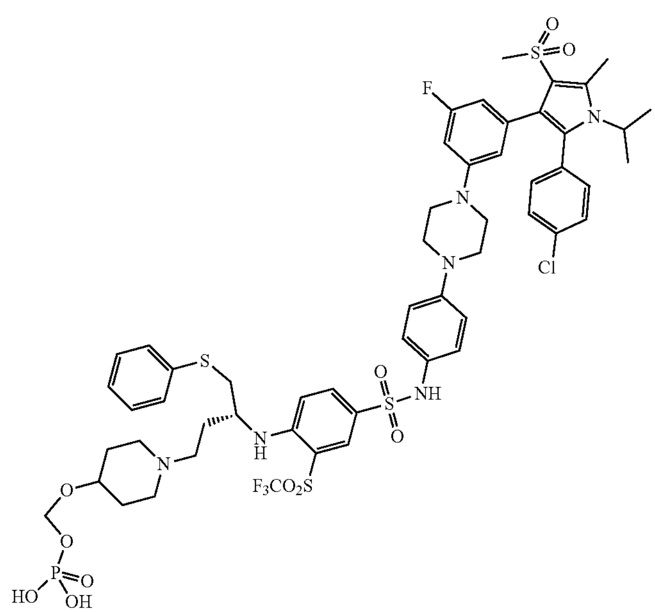 |

TABLE 1-A-continued

| Compound | Structure |
|---|---|
| A3 | 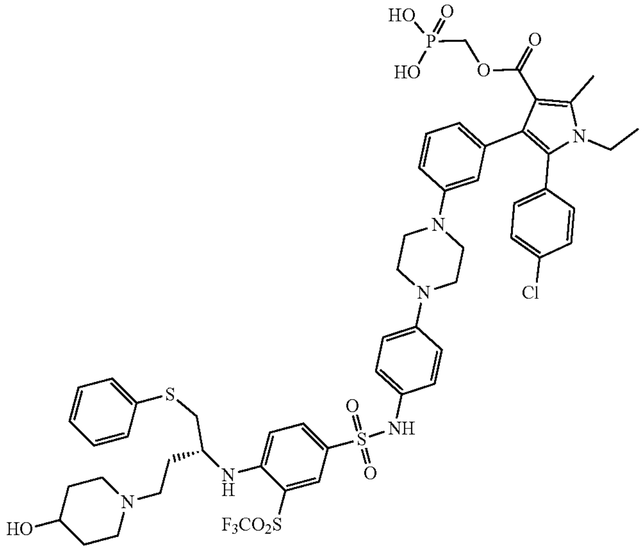 |
| A4 | 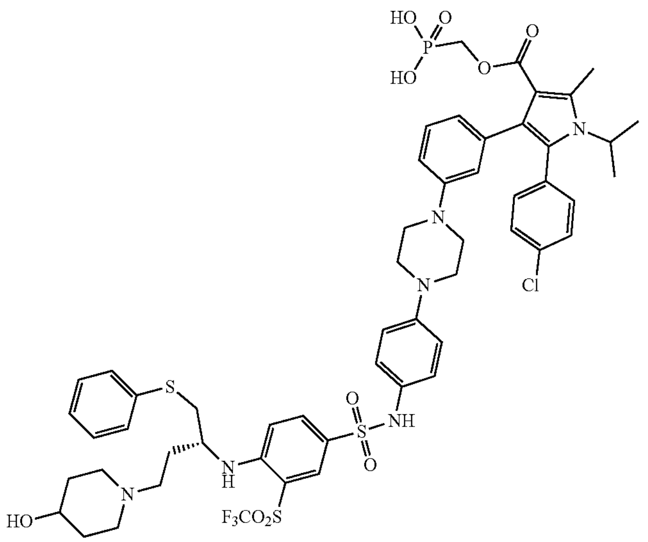 |
| A5 | 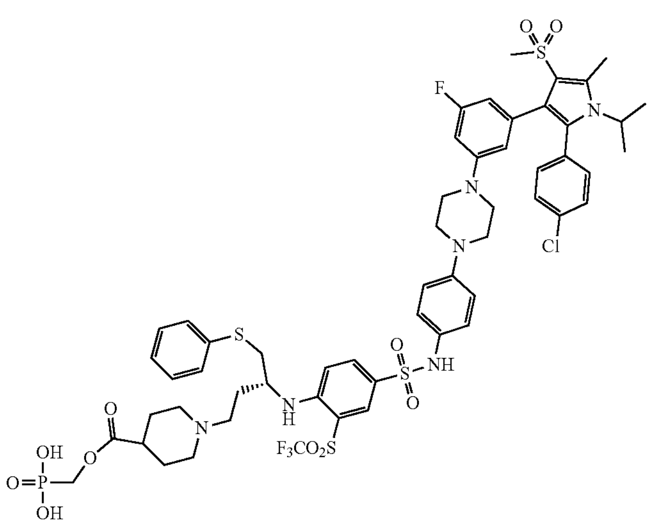 |

TABLE 1-A-continued
| Compound | Structure |
|---|---|
| A6 | 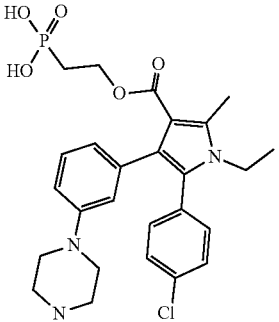 |
| A7 | 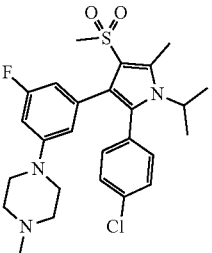 |
| A8 | 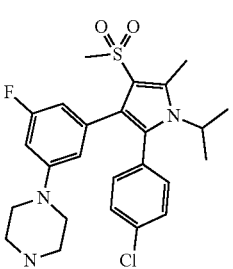 |

TABLE 1-A-continued

| Compound | Structure |
|---|---|
| A9 | 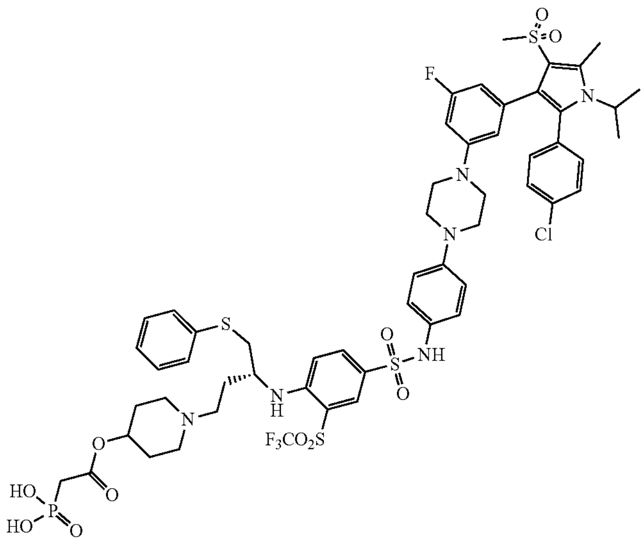 |
| A10 | 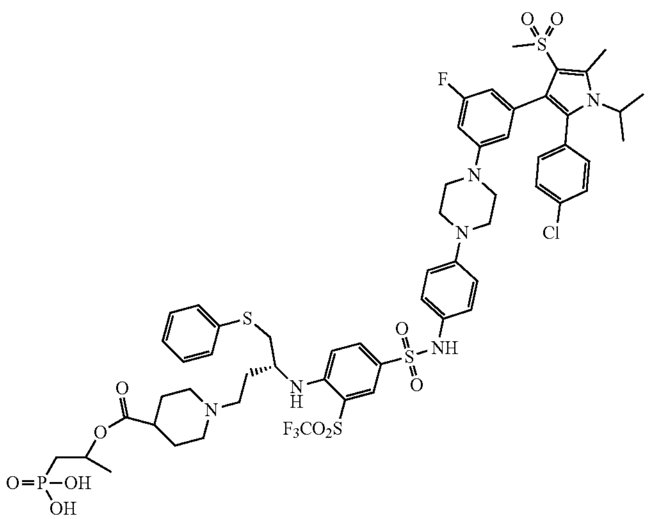 |
| A11 | 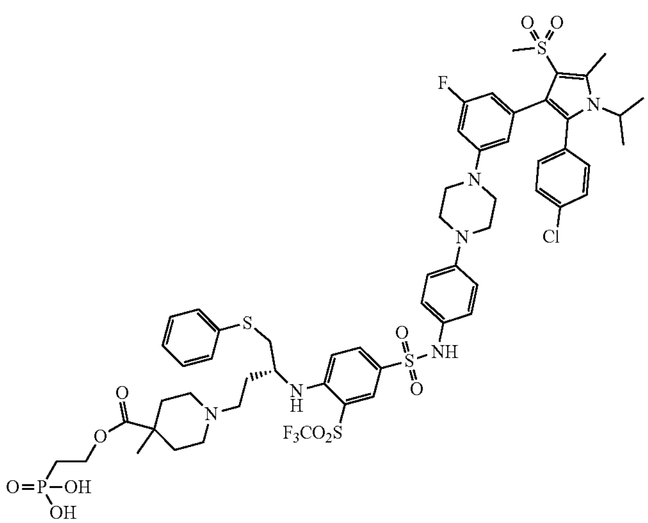 |

TABLE 1-A-continued
| Compound | Structure |
|---|---|
| A12 | 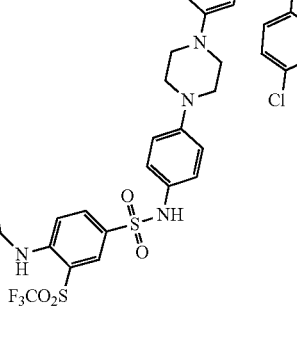 |
| A13 | 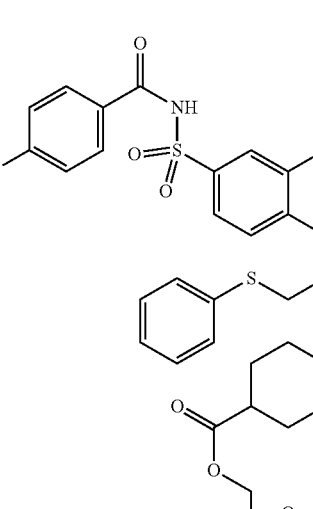 |
| A14 | 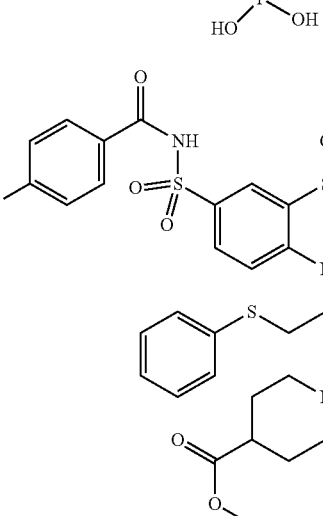 |

TABLE 1-A-continued

| Compound | Structure |
| --- | --- |
| A15 | 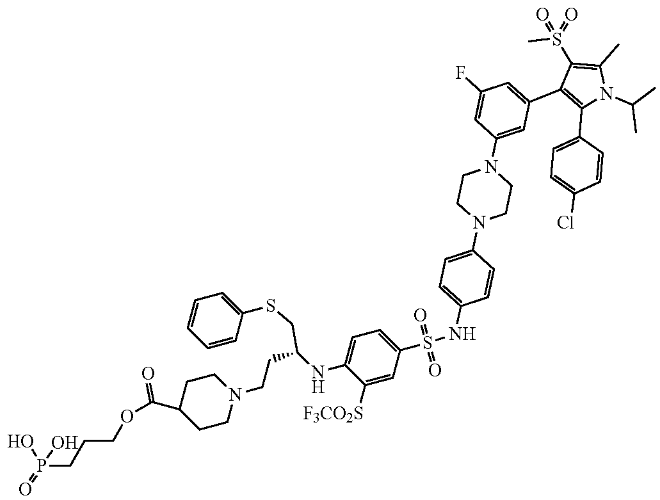 |
| A16 | 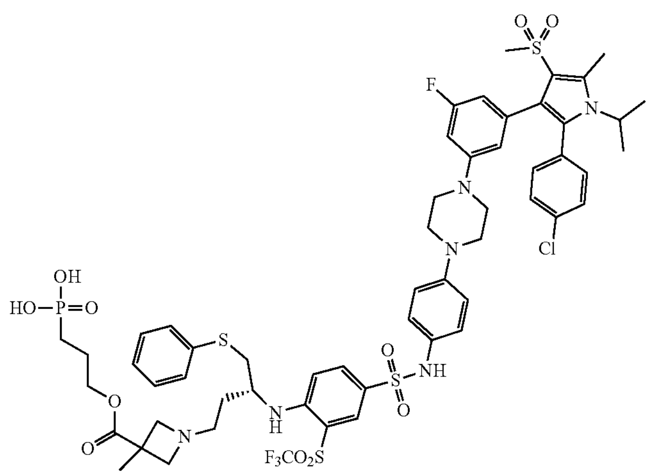 |
| A17 | 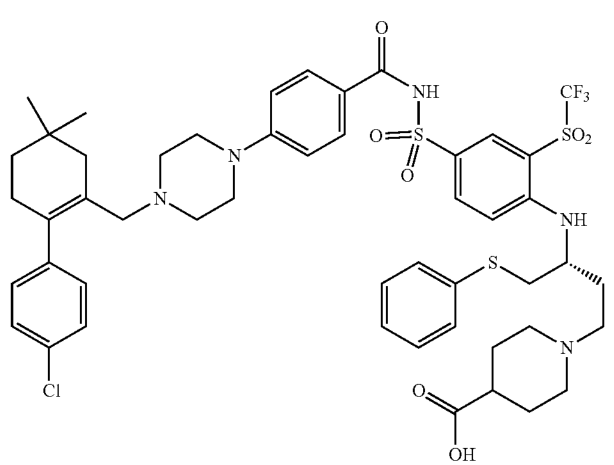 [SMILES: CC1(C)CCC(c2ccc(Cl)cc2)=C(CN2CCN(c3ccc(C(=O)NS(=O)(=O)c4ccc(N[C@H](CCN5CCC(C(=O)O)CC5)CSc5ccccc5)c(S(=O)(=O)C(F)(F)F)c4)cc3)CC2)C1] |

TABLE 1-A-continued
| Compound | Structure |
|---|---|
| A18 | 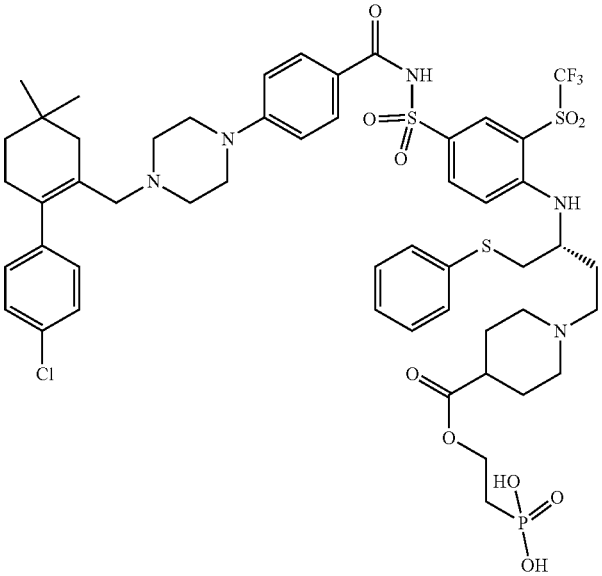 [SMILES: CC1(C)CCC(c2ccc(Cl)cc2)=C(CN2CCN(c3ccc(C(=O)NS(=O)(=O)c4ccc(N[C@H](CCN5CCC(C(=O)OCCP(=O)(O)O)CC5)CSc5ccccc5)c(S(=O)(=O)C(F)(F)F)c4)cc3)CC2)C1] |
| A19 | 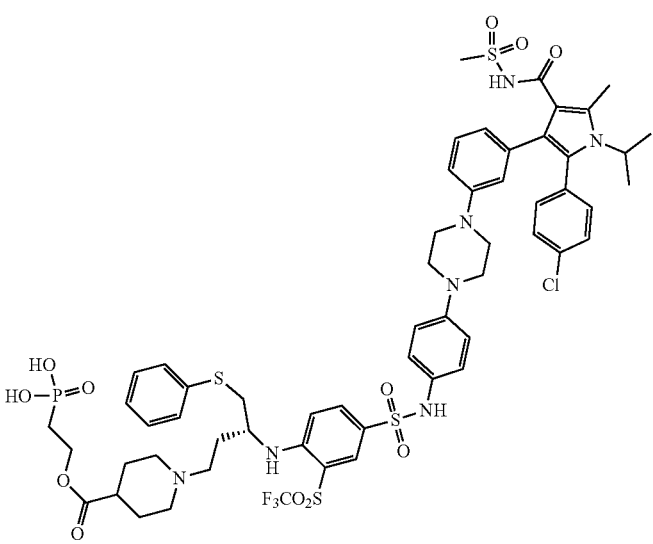 |
In certain embodiments, the Bcl-2/Bcl-xL dual inhibitors described herein having a structural formula (IV) is a compound selected from Table 1-B.

TABLE 1-B
| Compound | Structure |
|---|---|
| B1 | 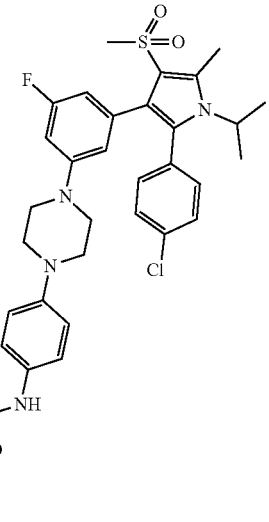 |
| B2 | 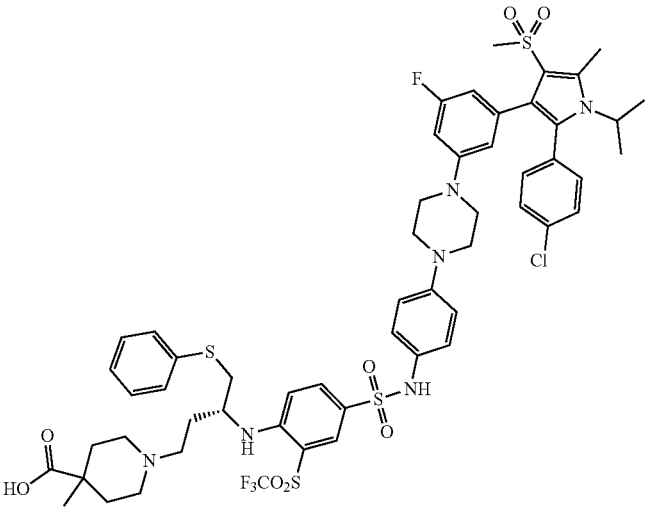 |
| B3 | 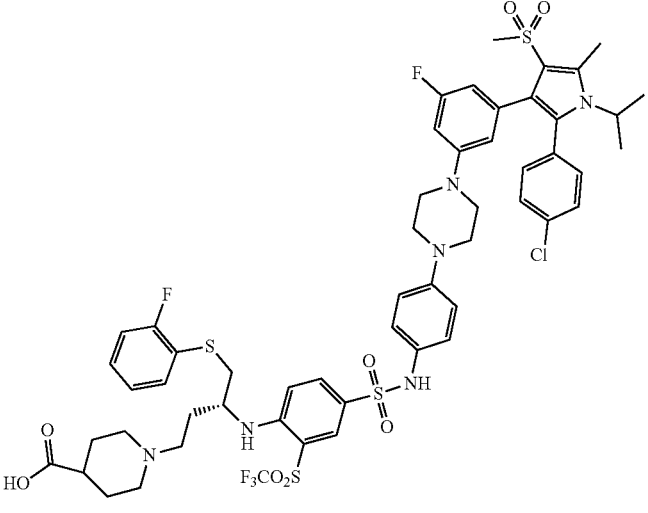 |

TABLE 1-B-continued
| Compound | Structure |
|---|---|
| B4 | 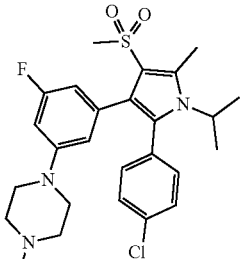 |
| B5 | 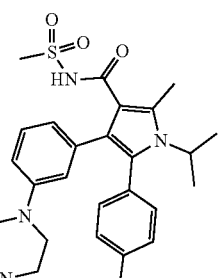 |
| B6 | 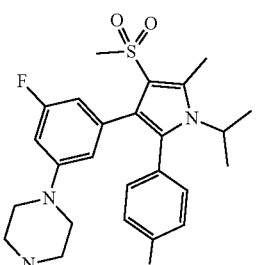 |

TABLE 1-B-continued

| Compound | Structure |
|---|---|
| B7 | 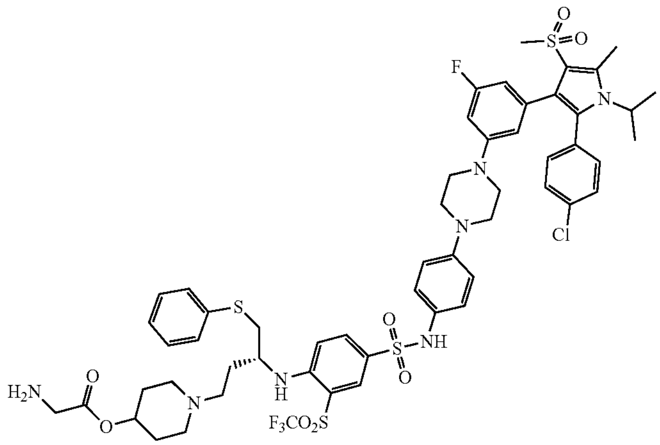 |
| B8 | 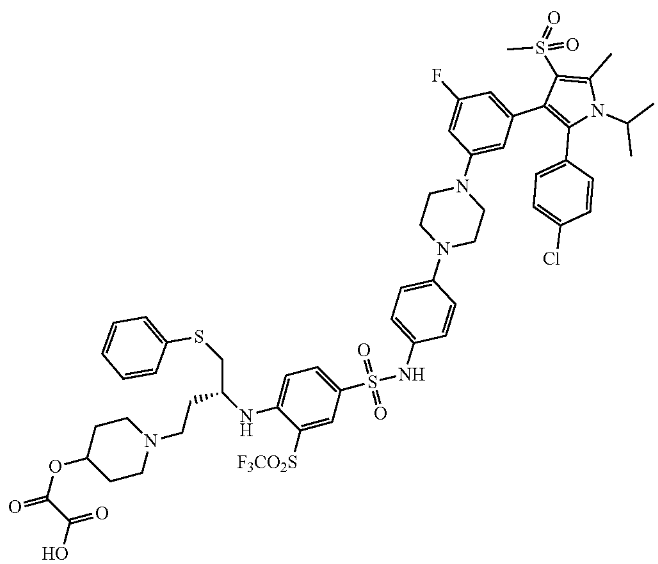 |
| B9 | 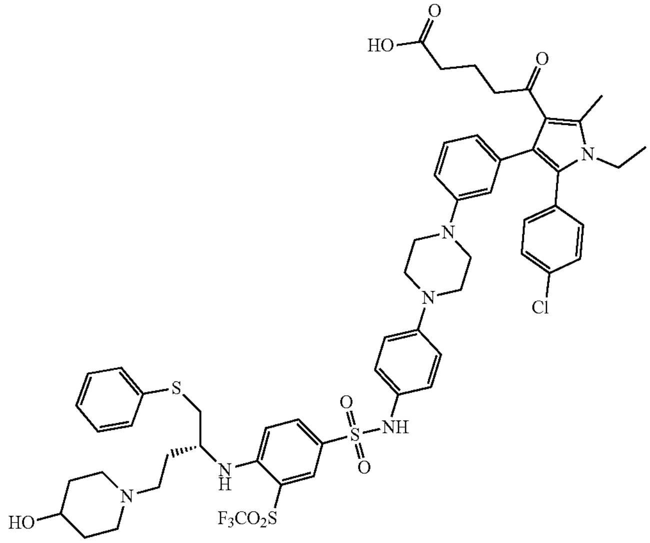 |

TABLE 1-B-continued

| Compound | Structure |
|---|---|
| B10 | (structure) |
| B11 | (structure) |
| B12 | (structure) |

In certain embodiments, the Bcl-2 inhibitors described herein having a structural formula (V) is a compound selected from Table 1-C or a pharmaceutically acceptable salt of the compound.
TABLE 1-C
| Compound | Structure |
|---|---|
| C1 | 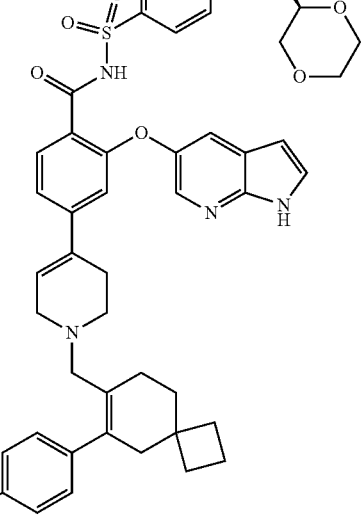 |
| C2 | 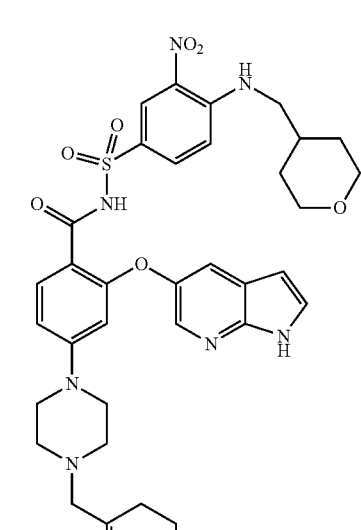 |

TABLE 1-C-continued
| Compound | Structure |
|---|---|
| C3 | 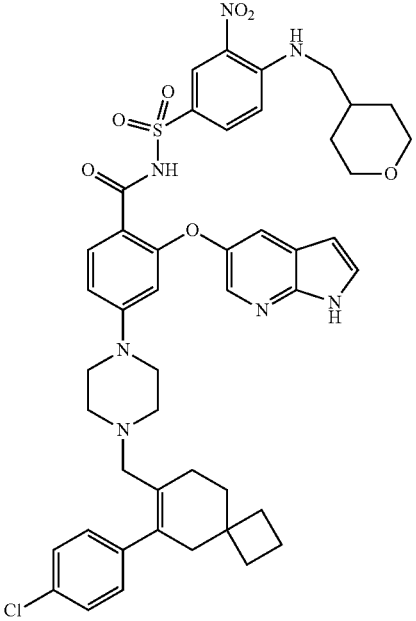 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] |
| C4 | 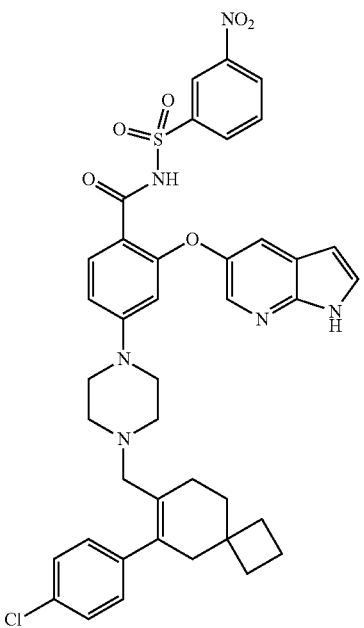 [SMILES: O=C(NS(=O)(=O)c1cccc([N+](=O)[O-])c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C5 | 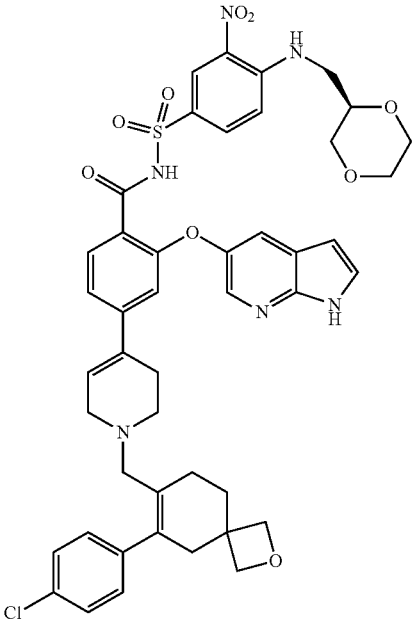 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1] |
| C6 | 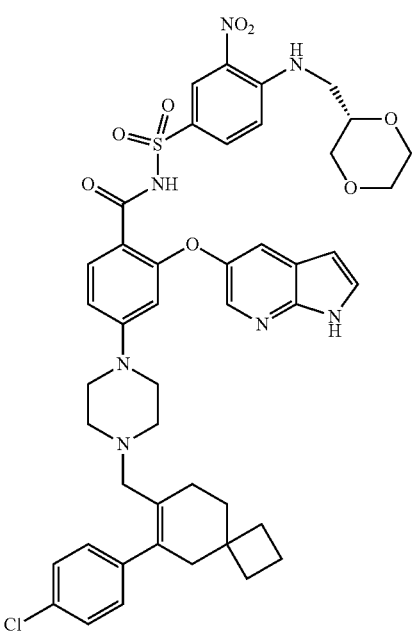 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C7 | 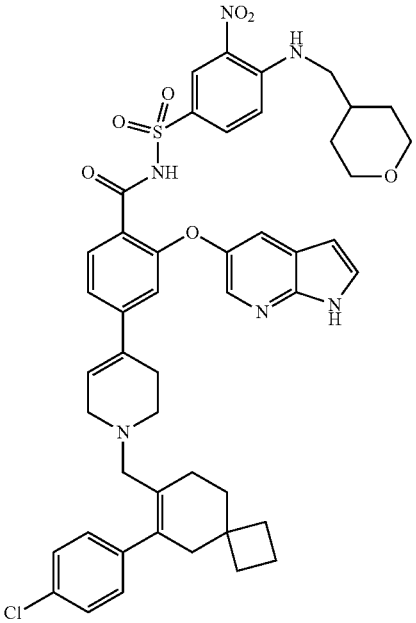 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CCC4)CC3)CC2)cc1Oc1cnc2[nH]ccc2c1] |
| C8 | 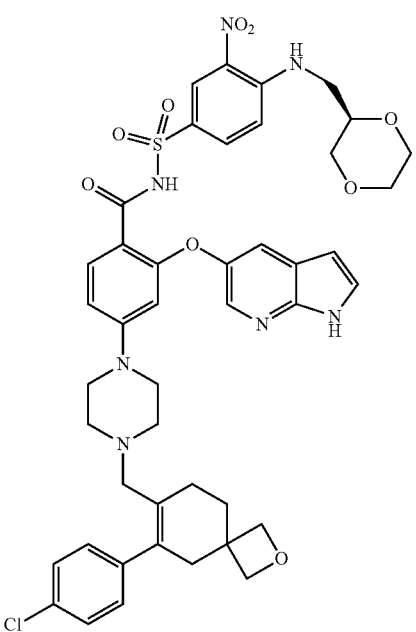 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CC3)COC4)CC2)cc1Oc1cnc2[nH]ccc2c1] |

TABLE 1-C-continued
| Compound | Structure |
|---|---|
| C9 | 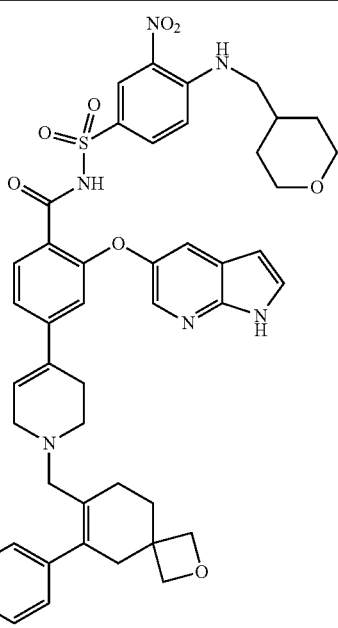 |
| C10 | 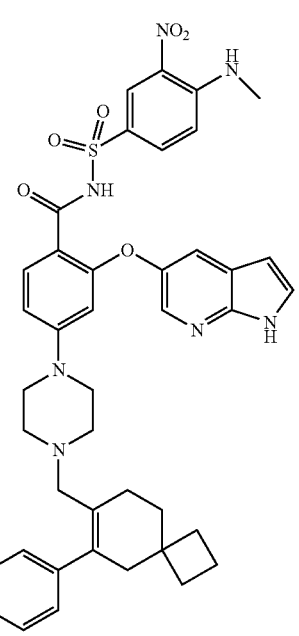 |

TABLE 1-C-continued
| Compound | Structure |
|---|---|
| C11 | 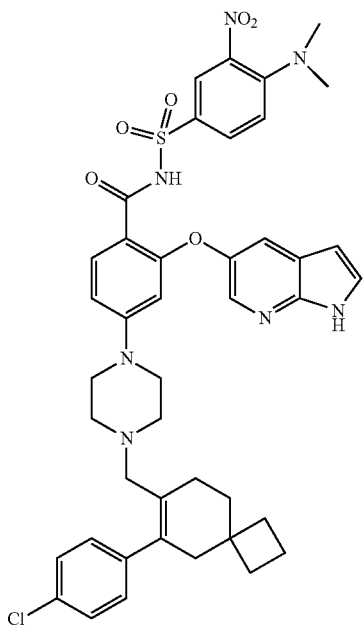 [SMILES: CN(C)c1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] |
| C12 | 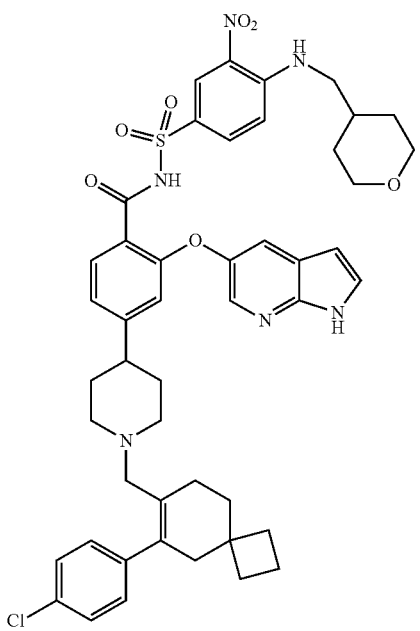 [SMILES: O=C(NS(=O)(=O)c1ccc(NCC2CCOCC2)c([N+](=O)[O-])c1)c1ccc(C2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C13 | 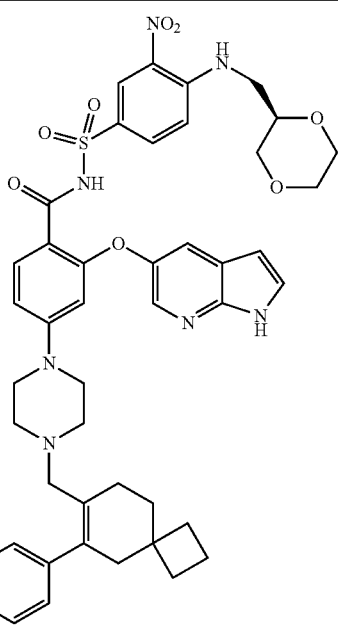 |
| C14 | 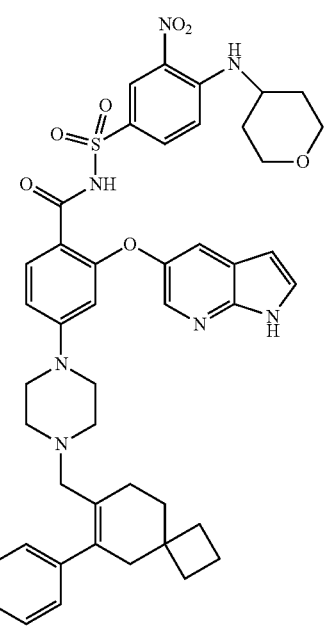 |

TABLE 1-C-continued
| Compound | Structure |
|---|---|
| C15 | 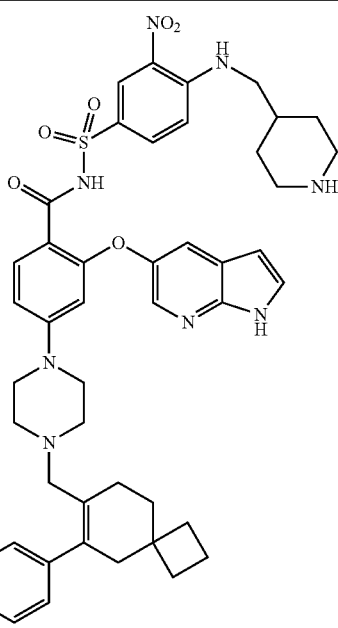 |
| C16 | 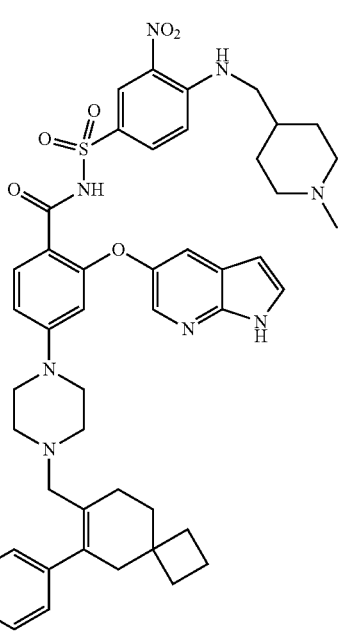 |

TABLE 1-C-continued
| Compound | Structure |
|---|---|
| C17 | 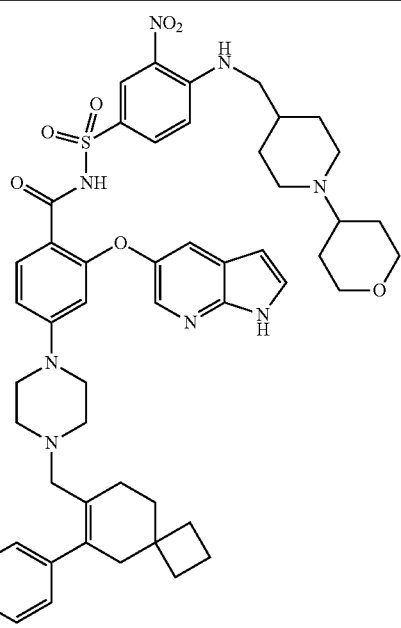 |
| C18 | 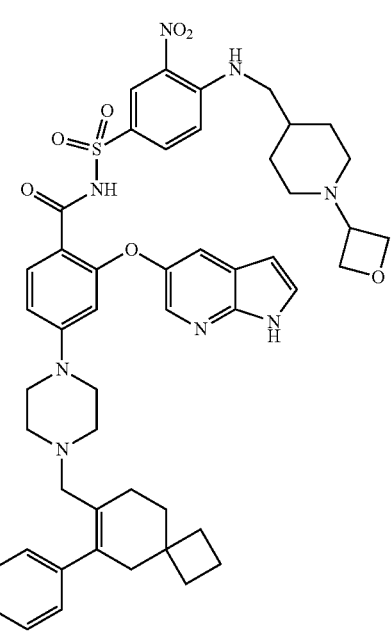 |

TABLE 1-C-continued
| Compound | Structure |
|---|---|
| C19 | 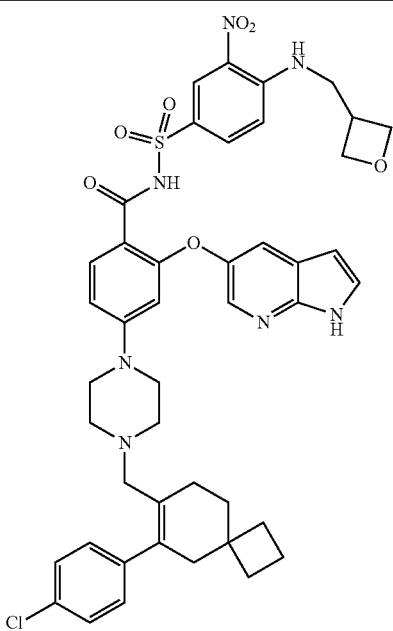 |
| C20 | 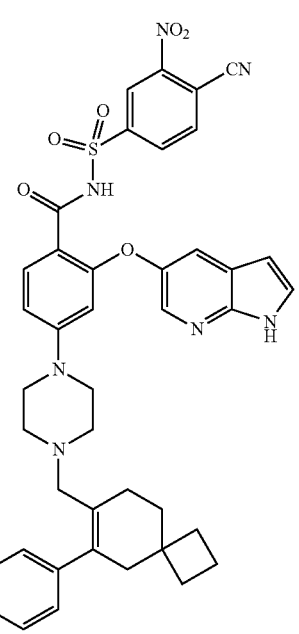 |

TABLE 1-C-continued
| Compound | Structure |
|---|---|
| C21 | 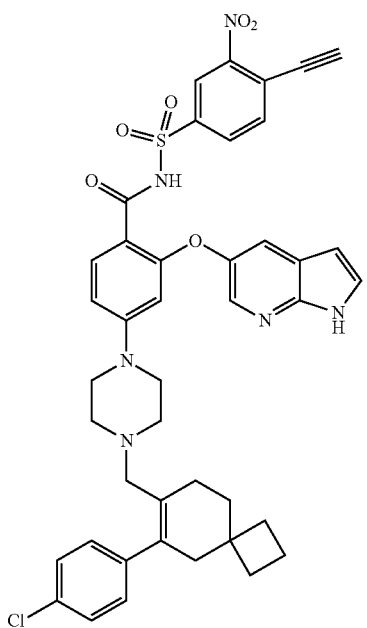 [SMILES: C#Cc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] |
| C22 | 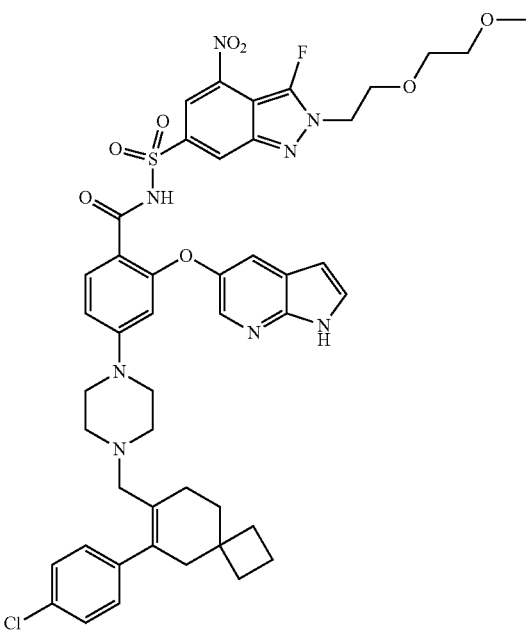 [SMILES: COCCOCCn1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2c1F] |

TABLE 1-C-continued
| Compound | Structure |
|---|---|
| C23 | 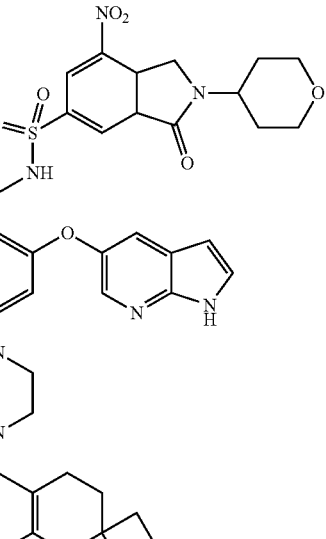 |
| C24 | 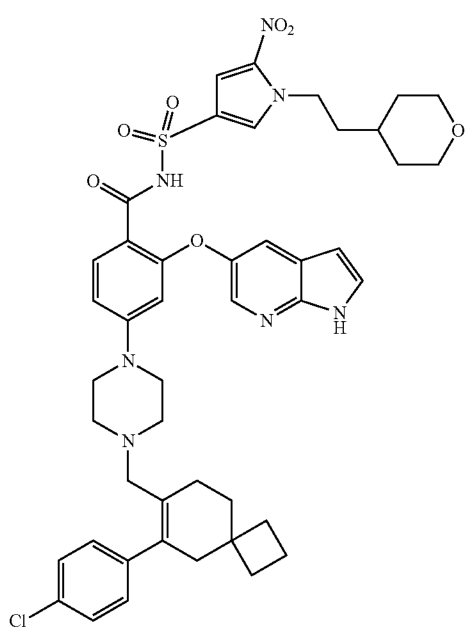 [SMILES: O=C(NS(=O)(=O)c1cc([N+](=O)[O-])n(CCC2CCOCC2)c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C25 | 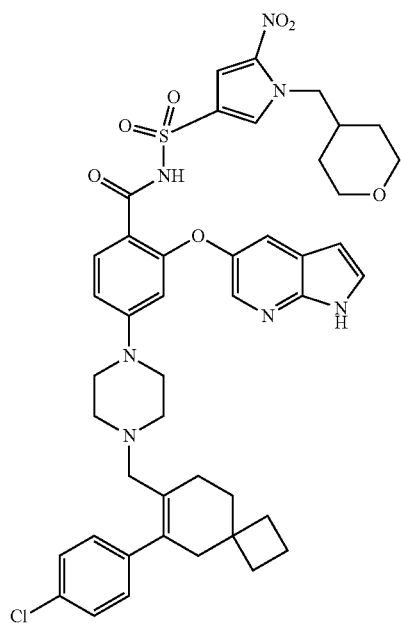 [SMILES: O=C(NS(=O)(=O)c1cc([N+](=O)[O-])n(CC2CCOCC2)c1)c1ccc(N2CCN(CC3=C(c4ccc(Cl)cc4)CC4(CCC4)CC3)CC2)cc1Oc1cnc2[nH]ccc2c1] |
| C26 | 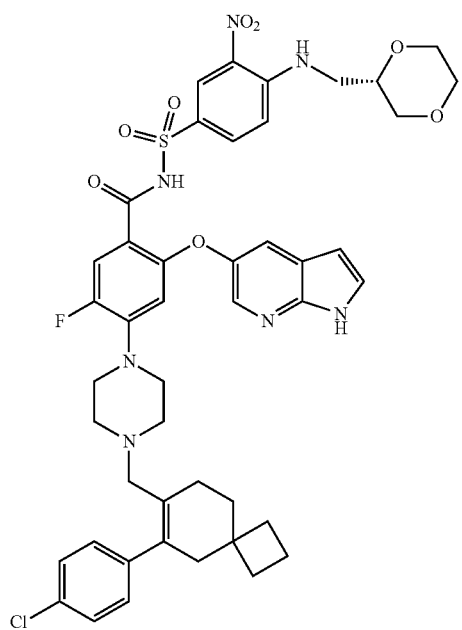 [SMILES: O=C(NS(=O)(=O)c1ccc(NC[C@H]2COCCO2)c([N+](=O)[O-])c1)c1cc(F)c(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C27 | 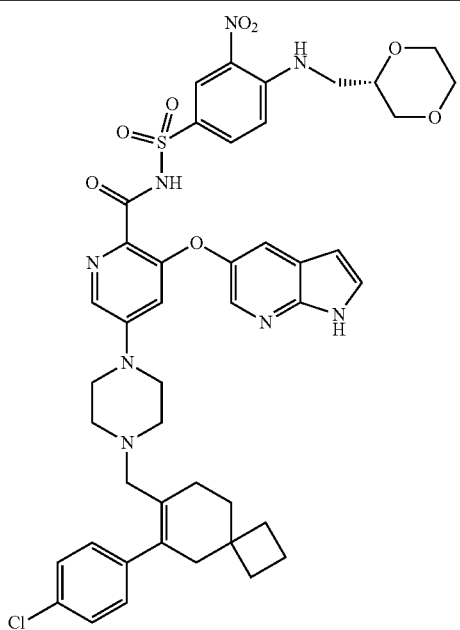 |
| C28 | 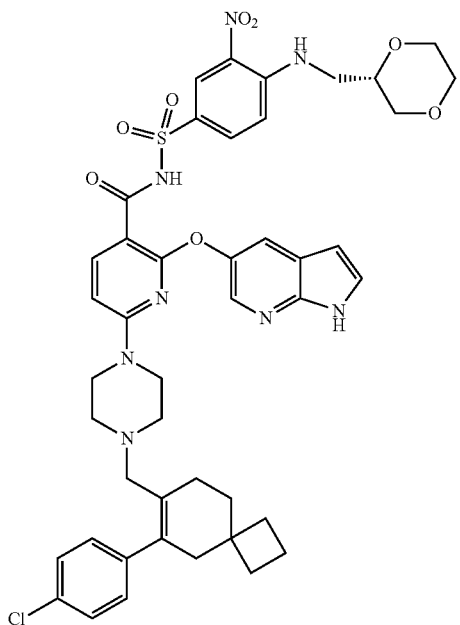 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)nc1Oc1cnc2[nH]ccc2c1] |

TABLE 1-C-continued
| Compound | Structure |
|---|---|
| C29 | 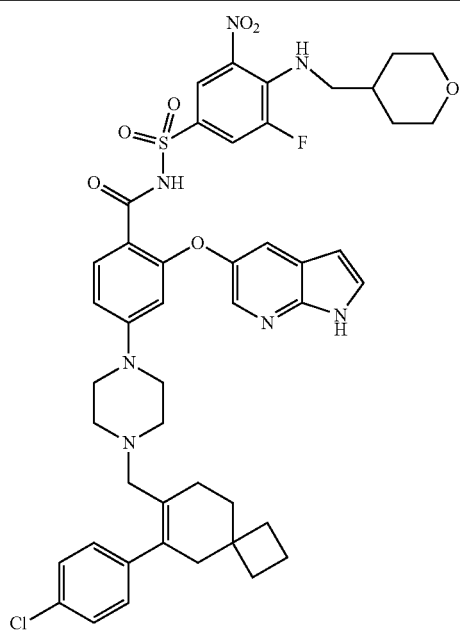 |
| C30 | 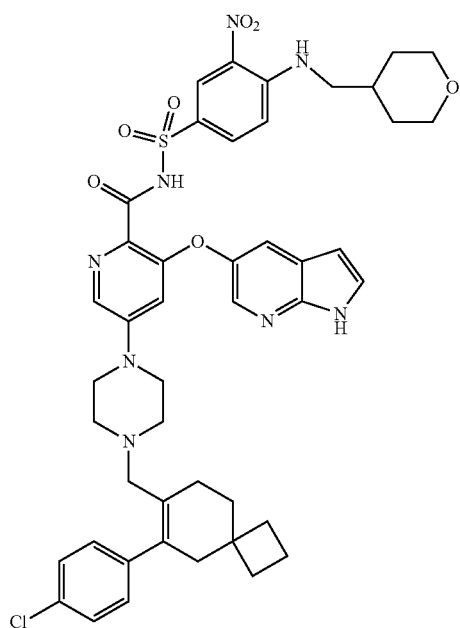 [SMILES: O=C(NS(=O)(=O)c1ccc(NCC2CCOCC2)c([N+](=O)[O-])c1)c1ncc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C31 | 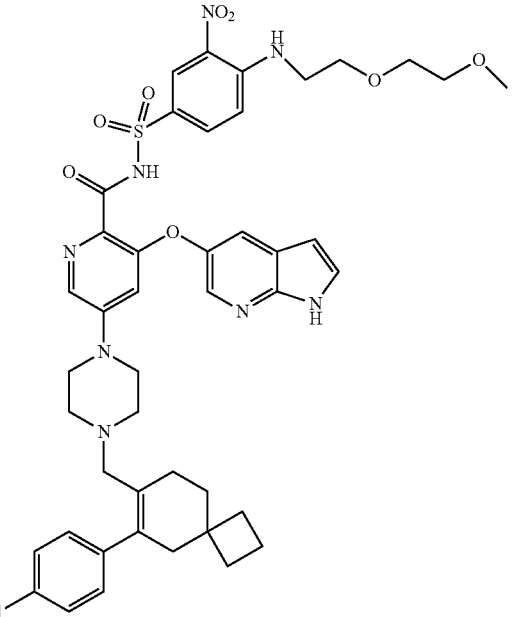 |
| C32 | 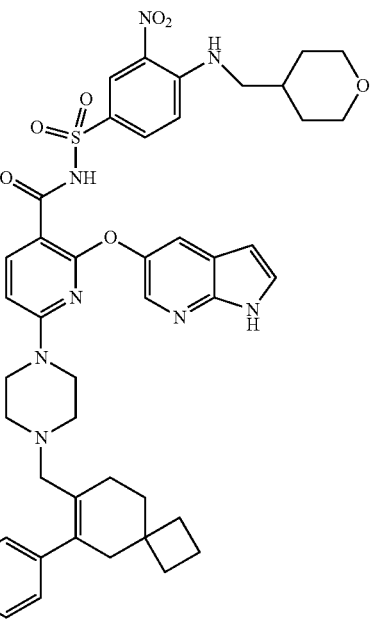 |

TABLE 1-C-continued
| Compound | Structure |
|---|---|
| C33 | 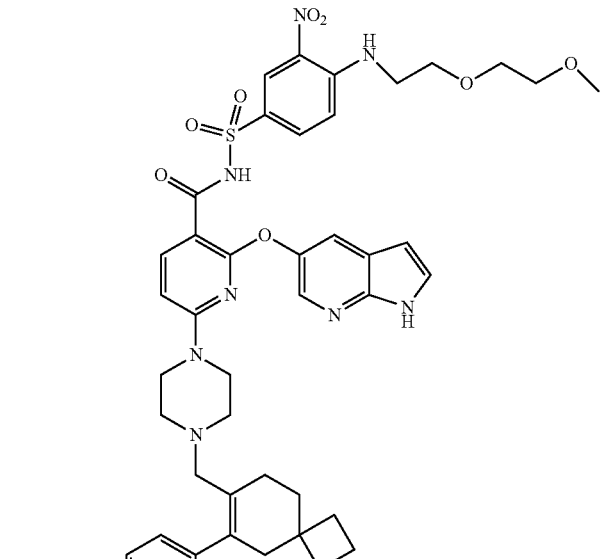 |
| C34 | 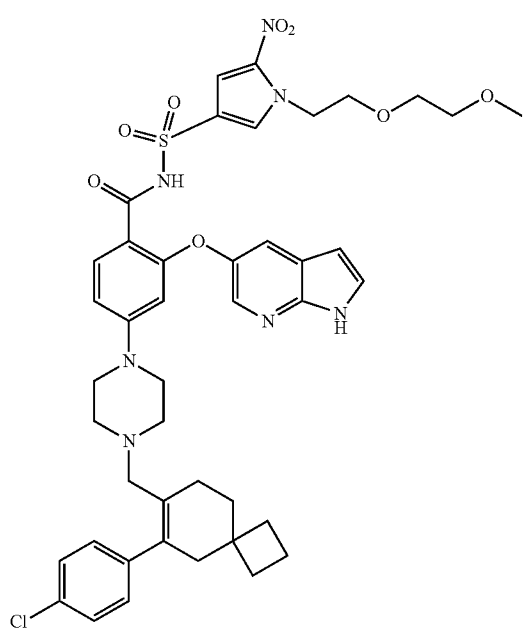 [SMILES: COCCOCCn1cc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] |

TABLE 1-C-continued

| Compound | Structure |
|---|---|
| C35 | 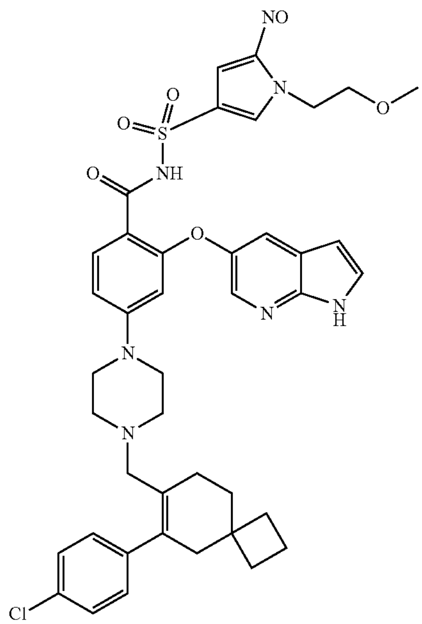 |
| C36 | 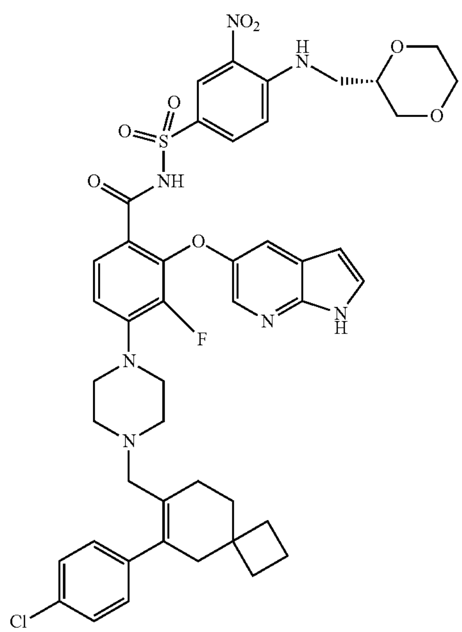 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)c(F)c1Oc1cnc2[nH]ccc2c1] |

TABLE 1-C-continued
| Compound | Structure |
|---|---|
| C37 | 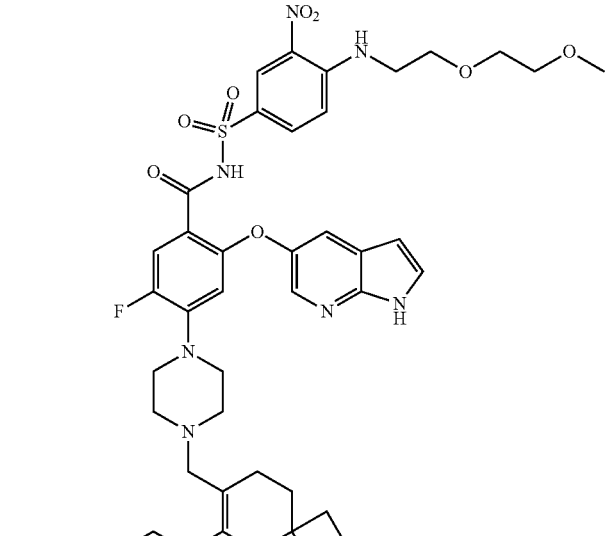 |
| C38 | 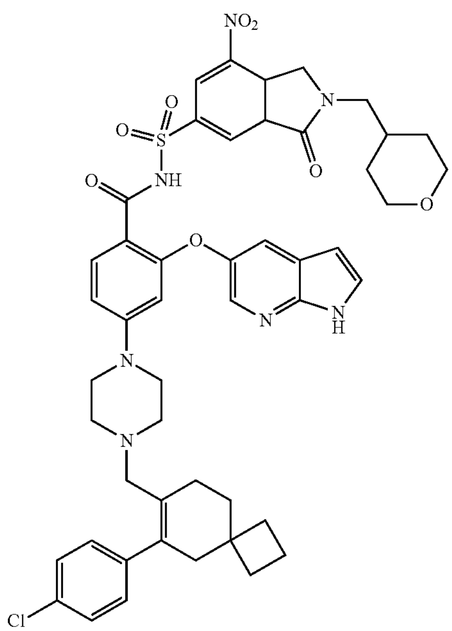 [SMILES: O=C(NS(=O)(=O)C1=CC2C(=O)N(CC3CCOCC3)CC2C([N+](=O)[O-])=C1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C39 | 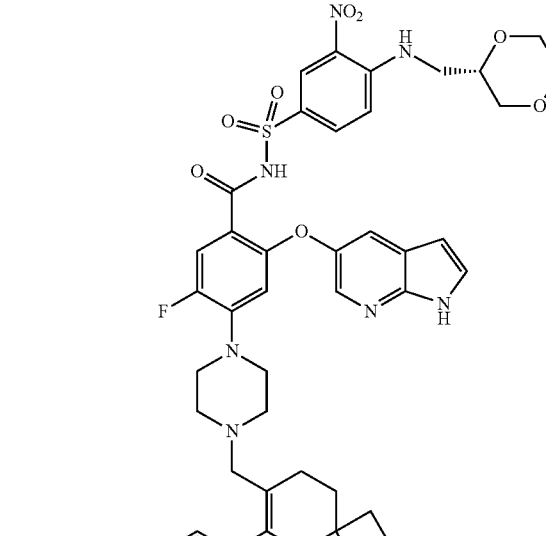 |
| C40 | 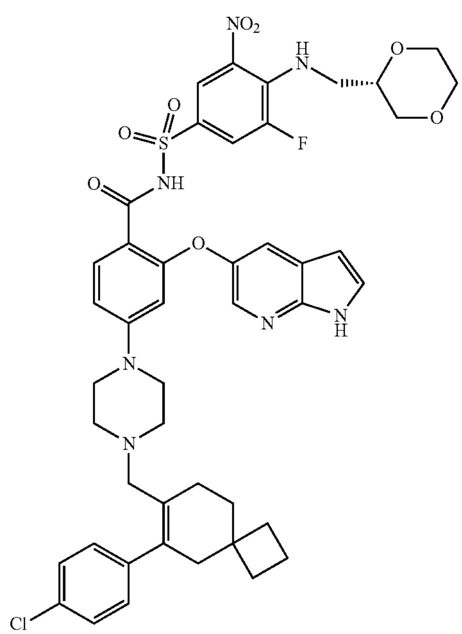 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C41 | 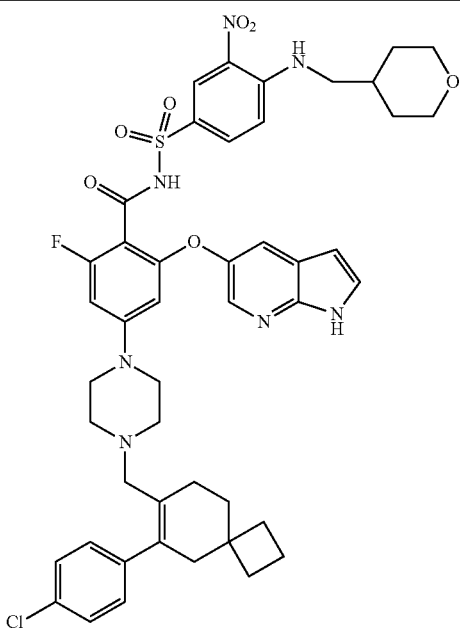 |
| C42 | 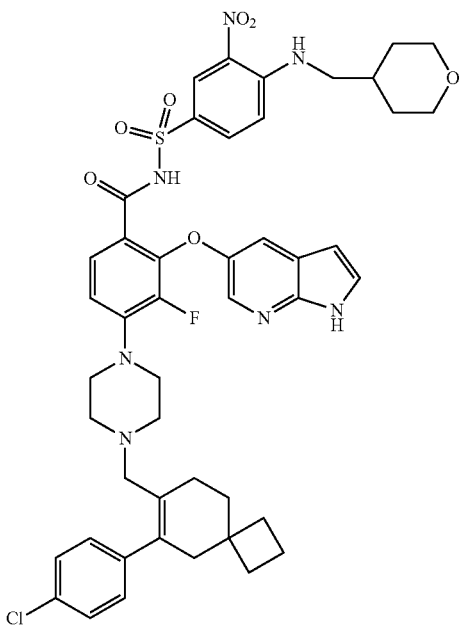 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)c(F)c1Oc1cnc2[nH]ccc2c1] |

TABLE 1-C-continued
| Compound | Structure |
|---|---|
| C43 | 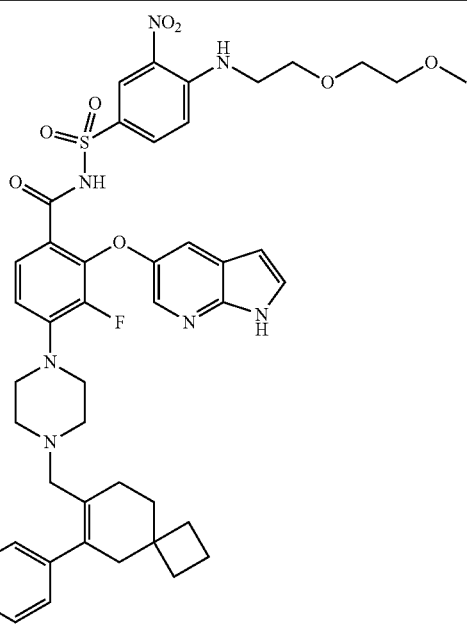 |
| C44 | 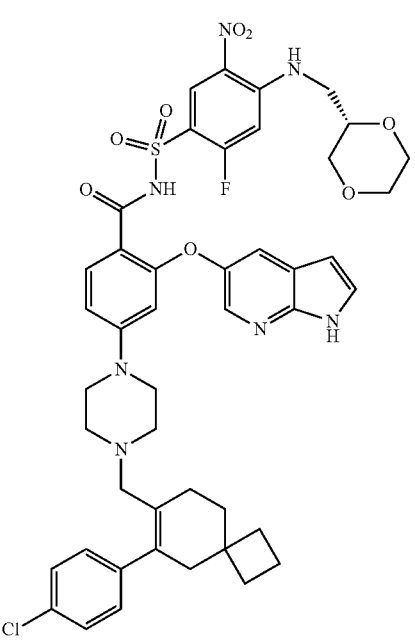 [SMILES: O=C(NS(=O)(=O)c1cc([N+](=O)[O-])c(NC[C@H]2COCCO2)cc1F)c1ccc(N2CCN(CC3=C(c4ccc(Cl)cc4)CC4(CCC4)CC3)CC2)cc1Oc1cnc2[nH]ccc2c1] |

119 120
TABLE 1-C-continued
| Compound | Structure |
|---|---|
| C45 | 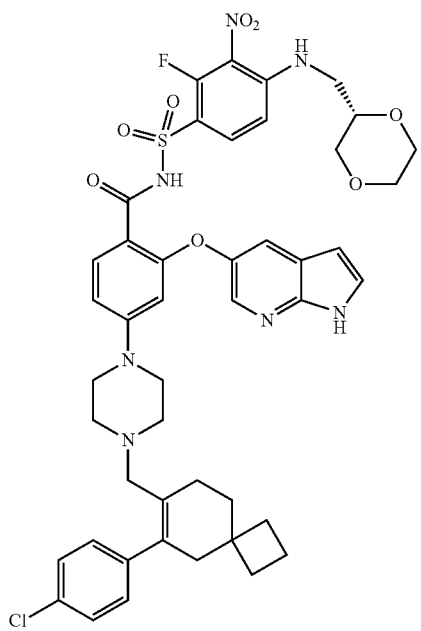 [SMILES: O=C(NS(=O)(=O)c1ccc(NC[C@H]2COCCO2)c([N+](=O)[O-])c1F)c1ccc(N2CCN(CC3=C(c4ccc(Cl)cc4)CC4(CCC4)CC3)CC2)cc1Oc1cnc2[nH]ccc2c1] |
| C46 | 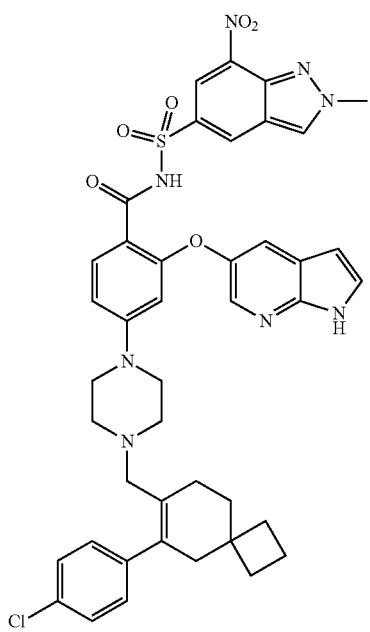 [SMILES: Cn1cc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2n1] |

TABLE 1-C-continued
| Compound | Structure |
|---|---|
| C47 | 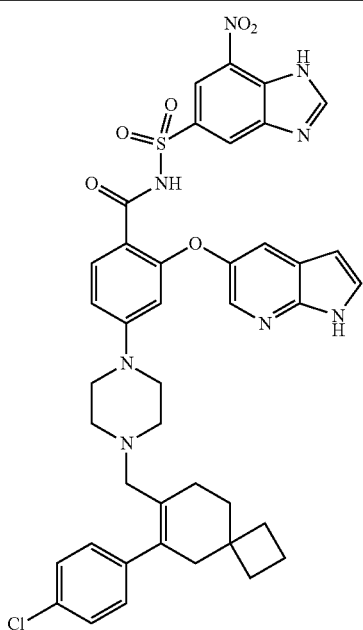 |
| C48 | 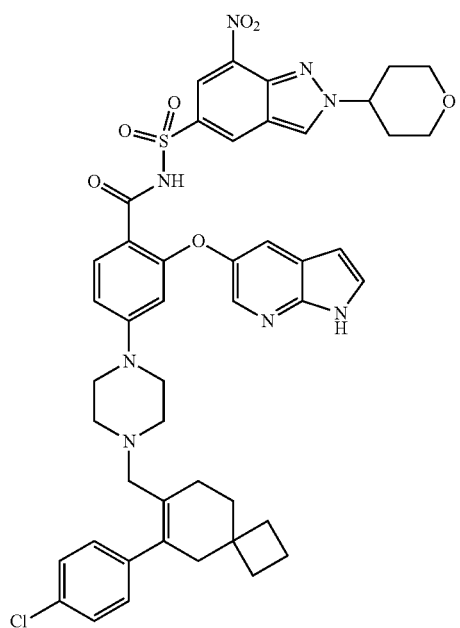 [SMILES: O=C(NS(=O)(=O)c1cc([N+](=O)[O-])c2nn(C3CCOCC3)cc2c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C49 | 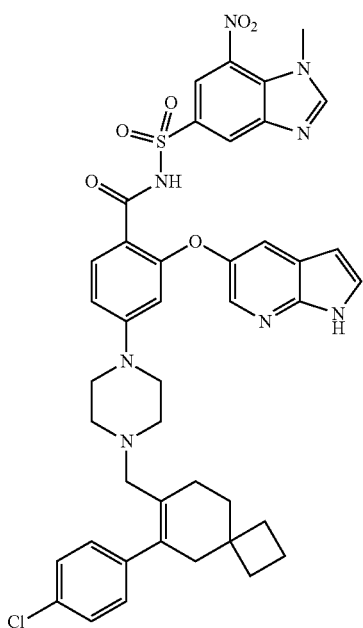 [SMILES: Cn1cnc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c21] |
| C50 | 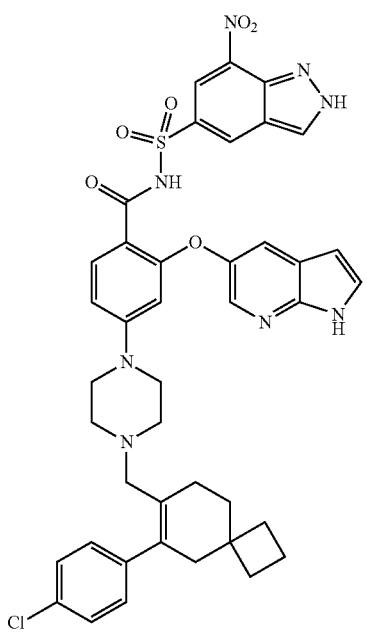 [SMILES: O=C(NS(=O)(=O)c1cc([N+](=O)[O-])c2n[nH]cc2c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C51 | 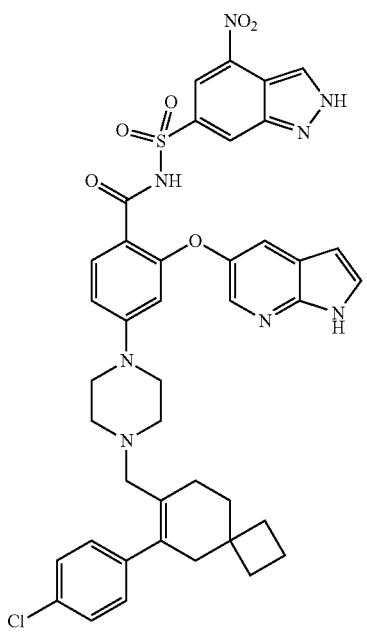 [SMILES: O=C(NS(=O)(=O)c1cc([N+](=O)[O-])c2c[nH]nc2c1)c1ccc(N2CCN(CC3=C(c4ccc(Cl)cc4)CC4(CCC4)CC3)CC2)cc1Oc1cnc2[nH]ccc2c1] |
| C52 | 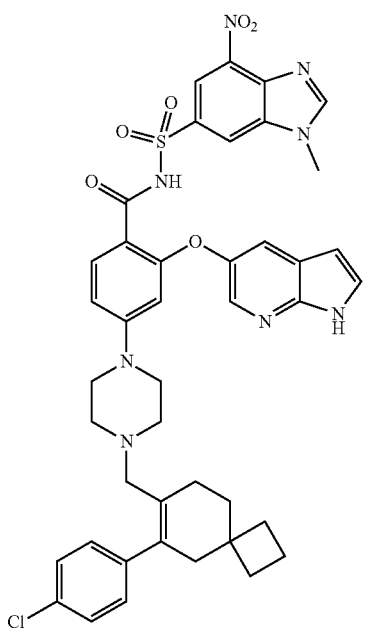 [SMILES: Cn1cnc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc21] |

TABLE 1-C-continued
| Compound | Structure |
|---|---|
| C53 | 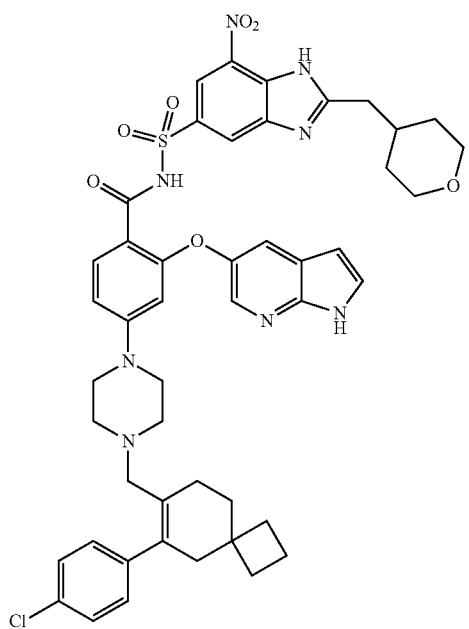 [SMILES: O=C(NS(=O)(=O)c1cc([N+](=O)[O-])c2[nH]c(CC3CCOCC3)nc2c1)c1ccc(N2CCN(CC3=C(c4ccc(Cl)cc4)CC4(CCC4)CC3)CC2)cc1Oc1cnc2[nH]ccc2c1] |
| C54 | 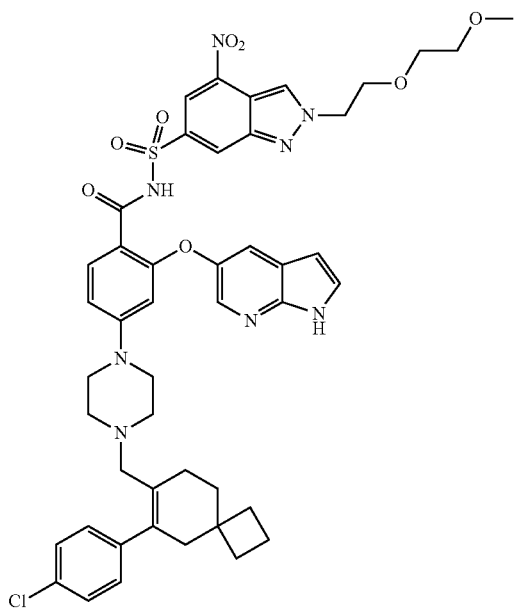 [SMILES: COCCOCCn1cc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2n1] |

TABLE 1-C-continued
| Compound | Structure |
|---|---|
| C55 | 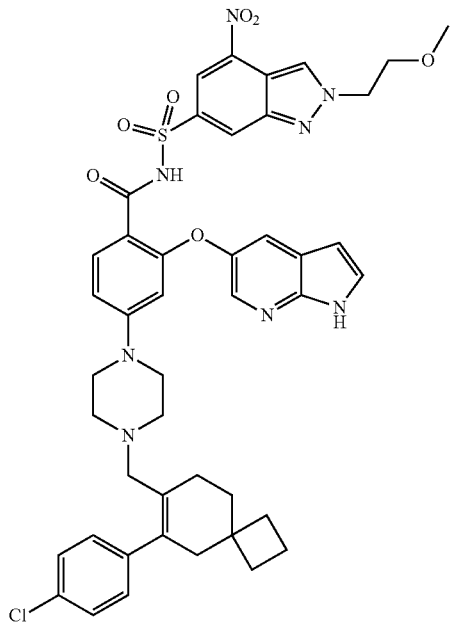 [SMILES: COCCn1cc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2n1] |
| C56 | 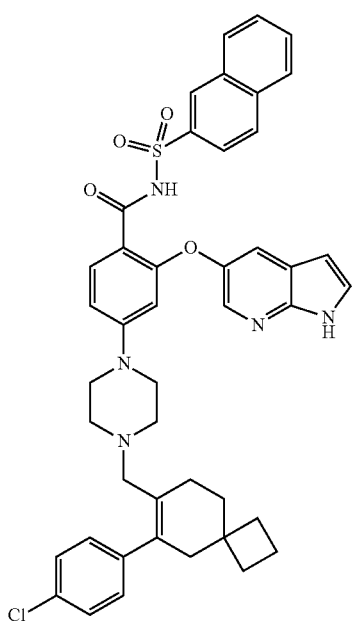 [SMILES: O=C(NS(=O)(=O)c1ccc2ccccc2c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C57 | 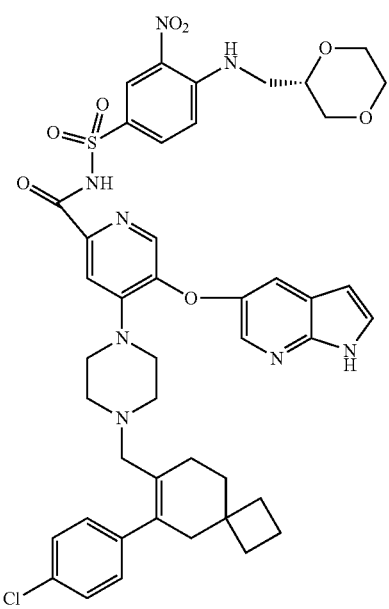 [SMILES: O=C(NS(=O)(=O)c1ccc(NC[C@H]2COCCO2)c([N+](=O)[O-])c1)c1cc(N2CCN(CC3=C(c4ccc(Cl)cc4)CC4(CCC4)CC3)CC2)c(Oc2cnc3[nH]ccc3c2)cn1] |
| C58 | 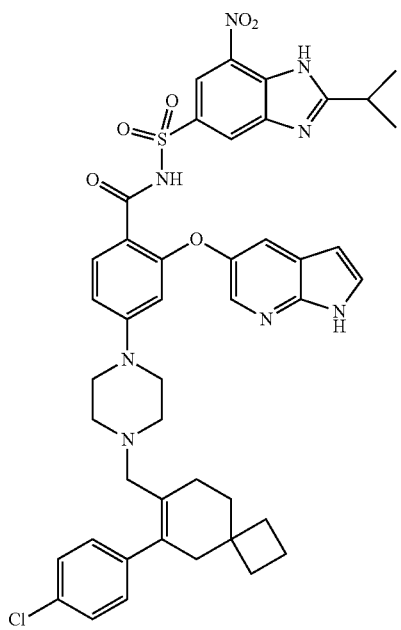 [SMILES: CC(C)c1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2[nH]1] |

TABLE 1-C-continued
| Compound | Structure |
|---|---|
| C59 | 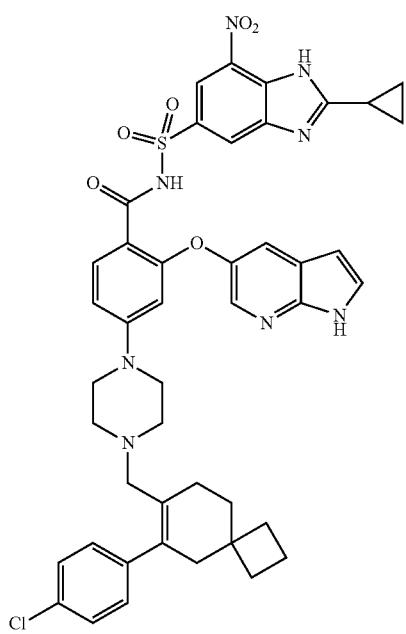 [SMILES: O=C(NS(=O)(=O)c1cc([N+](=O)[O-])c2[nH]c(C3CC3)nc2c1)c1ccc(N2CCN(CC3=C(c4ccc(Cl)cc4)CC4(CCC4)CC3)CC2)cc1Oc1cnc2[nH]ccc2c1] |
| C60 | 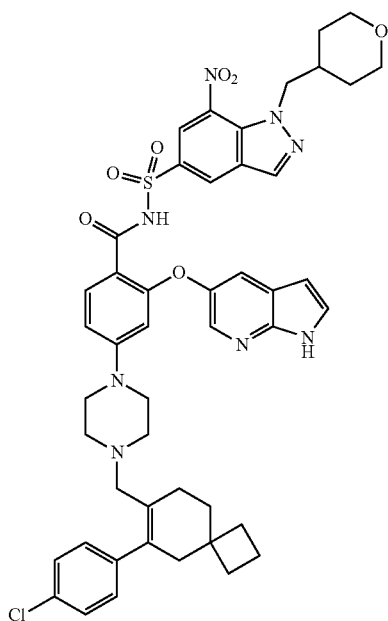 [SMILES: O=C(NS(=O)(=O)c1cc([N+](=O)[O-])c2c(cnn2CC2CCOCC2)c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C61 | 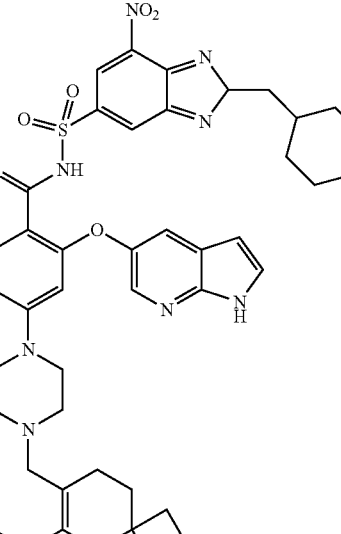 |
| C62 | 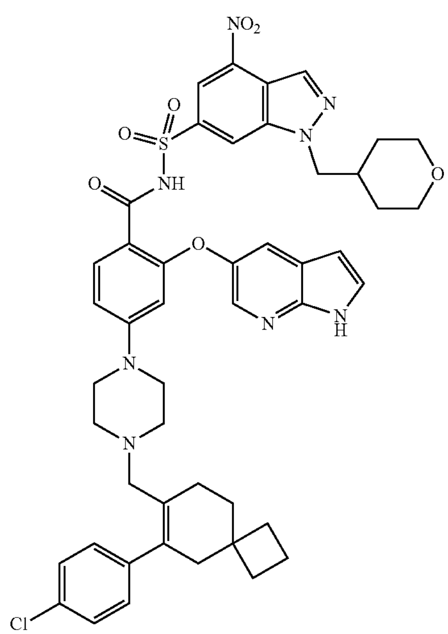 [SMILES: O=C(NS(=O)(=O)c1cc([N+](=O)[O-])c2cnn(CC3CCOCC3)c2c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C63 | 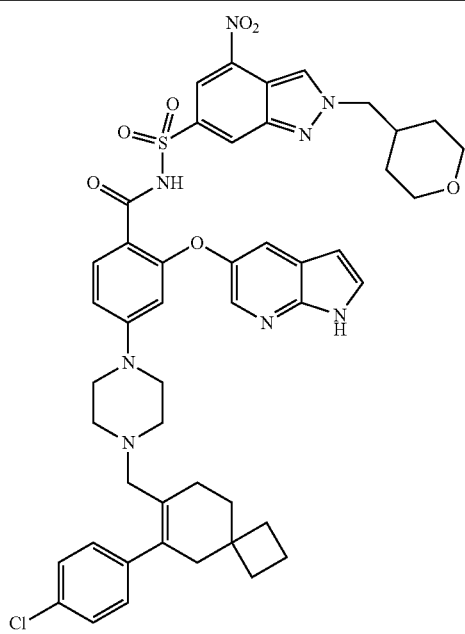 |
| C64 | 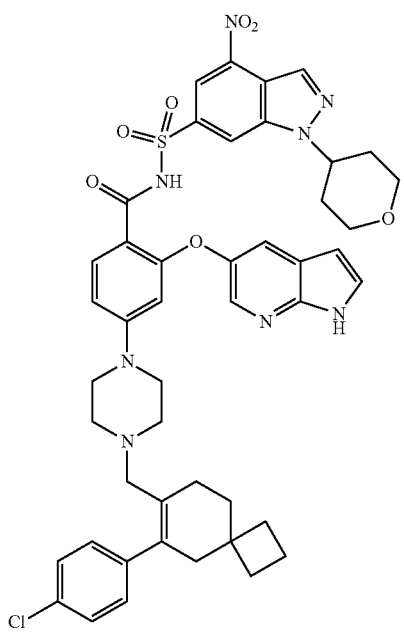 [SMILES: O=C(NS(=O)(=O)c1cc([N+](=O)[O-])c2cnn(C3CCOCC3)c2c1)c1ccc(N2CCN(CC3=C(c4ccc(Cl)cc4)CC4(CCC4)CC3)CC2)cc1Oc1cnc2[nH]ccc2c1] |

TABLE 1-C-continued
| Compound | Structure |
|---|---|
| C65 | 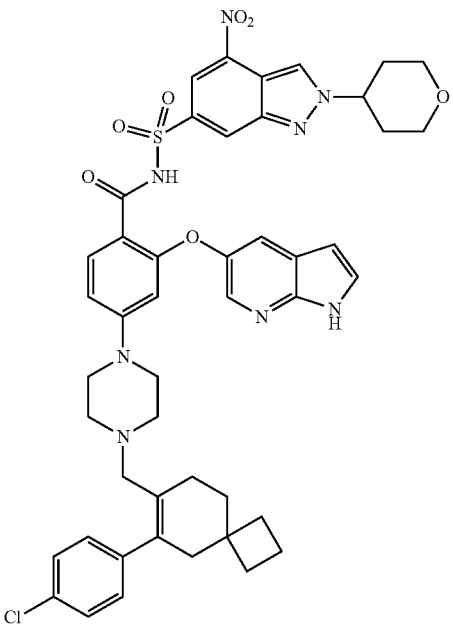 [SMILES: O=C(NS(=O)(=O)c1cc([N+](=O)[O-])c2cn(C3CCOCC3)nc2c1)c1ccc(N2CCN(CC3=C(c4ccc(Cl)cc4)CC4(CCC4)CC3)CC2)cc1Oc1cnc2[nH]ccc2c1] |
| C66 | 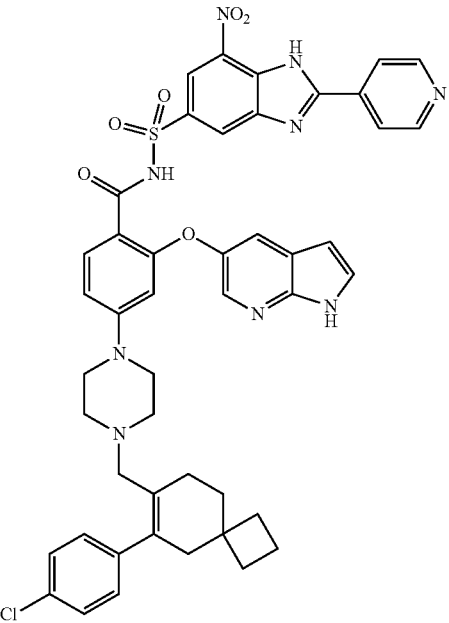 [SMILES: O=C(NS(=O)(=O)c1cc([N+](=O)[O-])c2[nH]c(-c3ccncc3)nc2c1)c1ccc(N2CCN(CC3=C(c4ccc(Cl)cc4)CC4(CCC4)CC3)CC2)cc1Oc1cnc2[nH]ccc2c1] |
In certain embodiments, the Bcl-2/Bcl-xL dual inhibitor is (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4-carbonyloxy)ethylphosphonic acid ("Compound A15") having the following structure

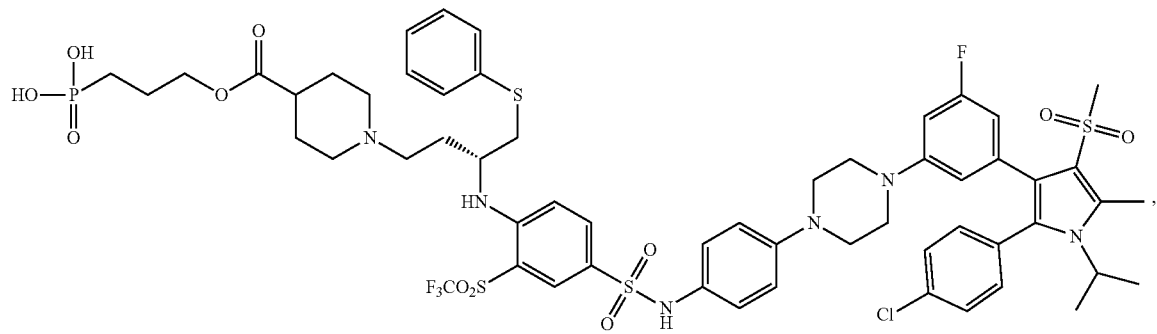

or a pharmaceutically acceptable salt thereof.

In certain embodiments, the Bcl-2/Bcl-xL dual inhibitor is (R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl) sulfamoyl)-2-(trifluoromethylsulfonyl)phenylamino)-4-(phenylthio)butyl)piperidine-4-carboxylic acid ("Compound B4") having the following structure

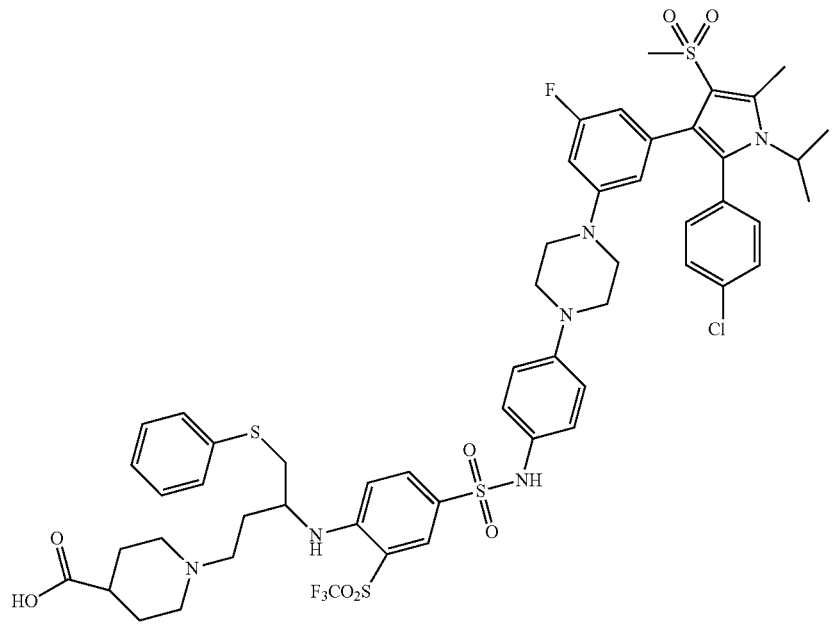

or a pharmaceutically acceptable salt thereof.

Compound A15 is a small-molecule compound that binds to Bcl-2, Bcl-xL and Bcl-w proteins with very high affinities with $IC_{50}$ values of 1.6 nM, 4.4 nM, and 9.3 nM, respectively. Compound A15 has a weak affinity to Mcl-1 protein. Compound A15 demonstrates potent cell growth inhibitory activity in vitro with nanomolar potencies in a subset of cancer cell lines. Mechanistically, Compound A15 effectively induces cleavage of caspase-3 and PARP, biochemical markers of apoptosis of human cancers in cancer cells and in xenograft tumor tissues. Compound B4 is an active metabolite of Compound A15.

In some embodiments, the Bcl-2 inhibitor is selected from the compounds having the following structures

143

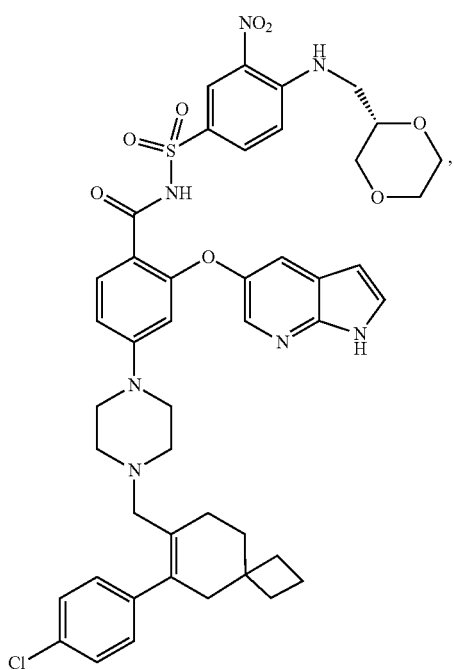 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

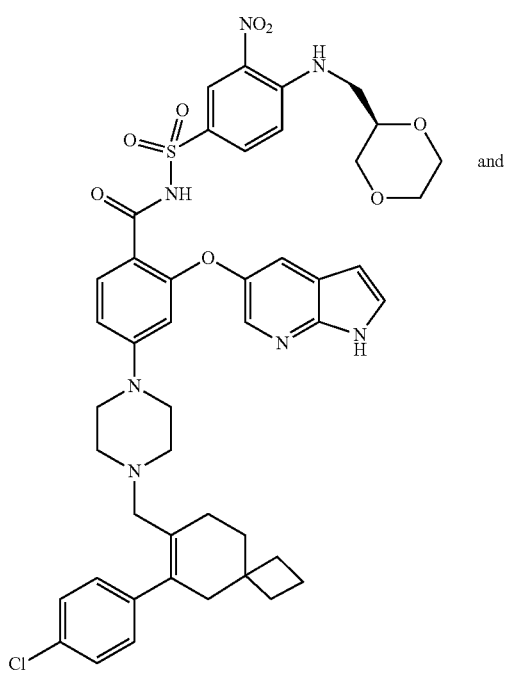

144

-continued

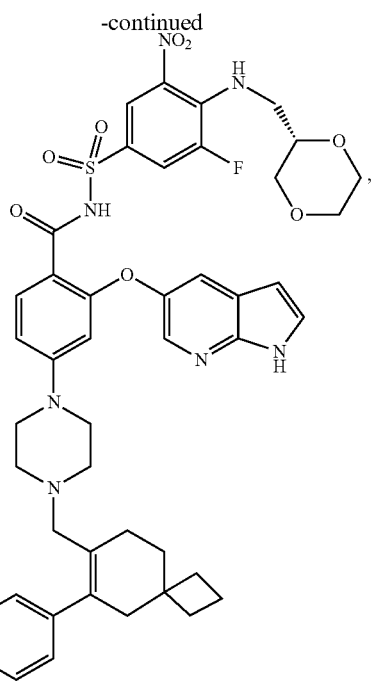

or a pharmaceutically acceptable salt thereof.

A number of Bcl-xL inhibitors are known in the field, such as those described in Urbaniak A, et al., Oncol Lett. 2019 November; 18(5):5097-5106, Zhan Y, et al, Cell Biosci. 2019 Jul. 23, 9:60., Hikita H, et al., Hepatology. 2010, 52:1310-21, Lee B, et al, Biochem Biophys Res Commun. 2019 Jun. 25; 514(2):518-523, Henz K, et al, Biol Chem. 2019 Jan. 28; 400(2):181-185, Wang Q, et al, Leuk Lymphoma. 2019 September; 60(9):2170-2180., Rello-Varona S, et al, Sci Rep. 2019 Mar. 7; 9(1):3816, Levesley J, et al, Neuro Oncol. 2018 Jan. 22; 20(2):203-214 and Lucantoni F, et al, Oncotarget. 2018 May 25; 9(40):26046-26063.

In certain embodiments, the Bcl-xL inhibitors described herein is selected from ABT-263, ABT-737, A-1331852, A-1155463 and WEHI-539.

MDM2 Inhibitors

In certain embodiments, the MDM2 inhibitor comprises the chemical structure of the following formula (VI):

(VI)

or a pharmaceutically acceptable salt thereof, wherein

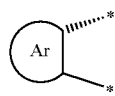

is selected from the group consisting of

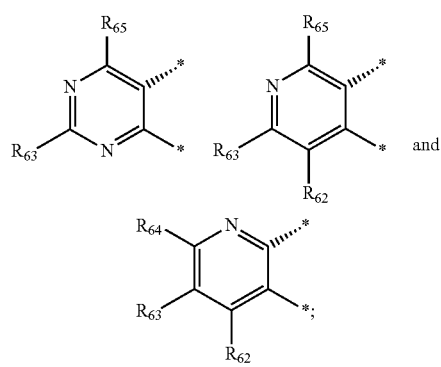

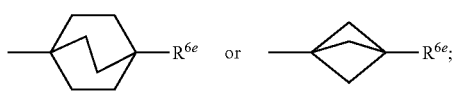

B is a $C_{4-7}$ carbocyclic ring;

$R_{61}$ is H, substituted or unsubstituted $C_{1-4}$ alkyl, substituted or unsubstituted cycloalkyl, substituted or unsubstituted heterocycloalkyl, $OR^{6a}$, or $NR^{6a}R^{6b}$;

$n_3$ is 0, 1, or 2;

$R_{62}$, $R_{63}$, $R_{64}$, $R_{65}$, $R_{67}$, $R_{68}$, $R_{69}$, and $R_{70}$, independently, are selected from the group consisting of H, F, Cl, $CH_3$, and $CF_3$;

$R_{66}$ is

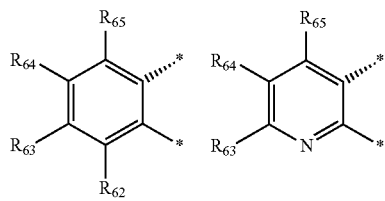

$R^{6a}$ is hydrogen or substituted or unsubstituted $C_{1-4}$ alkyl;
$R^{6b}$ is hydrogen or substituted or unsubstituted $C_{1-4}$ alkyl;
$R^{6c}$ and $R^{6d}$ are substituents on one carbon atom of ring B, wherein
$R^{6c}$ is H, $C_{1-3}$ alkyl, $C_{1-3}$ alkylene-$OR^{6a}$, $OR^{6a}$, or halo;
$R^{6d}$ is H, $C_{1-3}$ alkyl, $C_{1-3}$ alkylene-$OR^{6a}$, $OR^{6a}$, or halo; or
$R^{6c}$ and $R^{6d}$ are taken together with the carbon to which they are attached to form a 4 to 6-membered Spiro substituent, optionally containing an oxygen atom; and
$R^{6e}$ is —C(=O)$OR^{6a}$, —C(=O)$NR^{6a}R^{6b}$, or —C(=O)NHSO$_2$CH$_3$.

In certain embodiments,

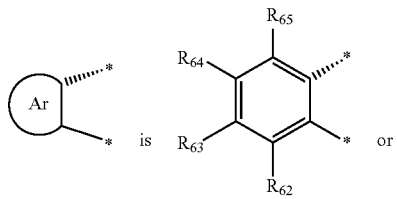

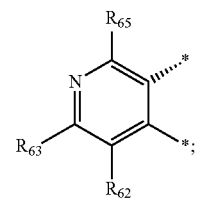

B is

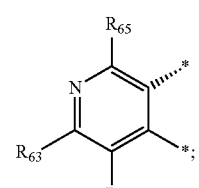

and $R^{6c}$ and $R^{6d}$ are F and F, H and H, OH and $CH_3$, OH and H, $CH_3$ and $CH_3$, $CH_3$ and OH, H and OH, $CH_2CH_3$ and $CH_2CH_3$, or $CH_2OH$ and $CH_2OH$.

In certain embodiments,

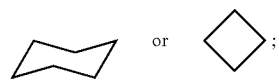

is H, $CH_3$, or $CH_2CH_3$.

In certain embodiments, $R_{62}$ is H; $R_{63}$ is halo; $R_{64}$ and $R_{65}$ are H.

In certain embodiments, $R_{67}$ is fluoro; each of $R_{68}$, $R_{69}$, and $R_{70}$ is H; and $R^{6e}$ is —C(=O)OH, —C(=O)NH$_2$, or —C(=O)NHSO$_2$CH$_3$.

In certain embodiments, the MDM2 inhibitor is a compound selected from:

Compound Q

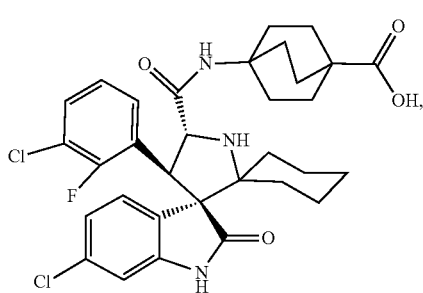

Compound M
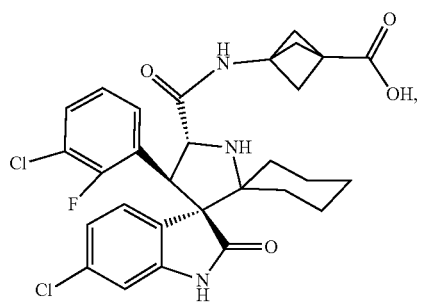
Compound N
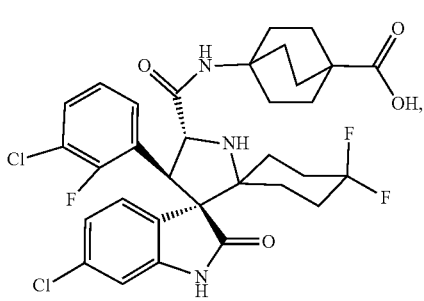
Compound H
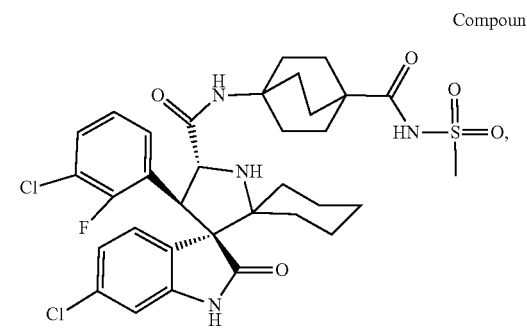
Compound J
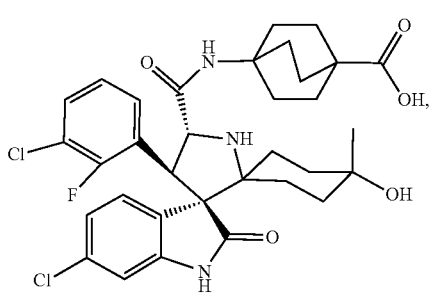
Compound G
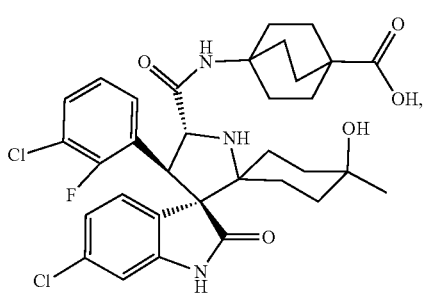
Compound E
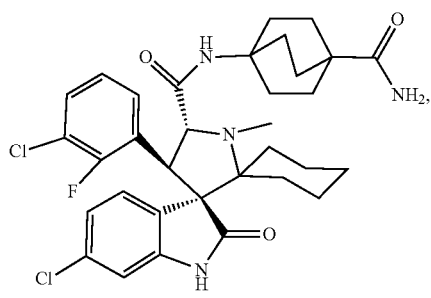
Compound C
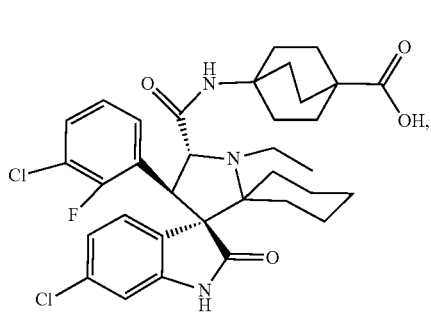
Compound F
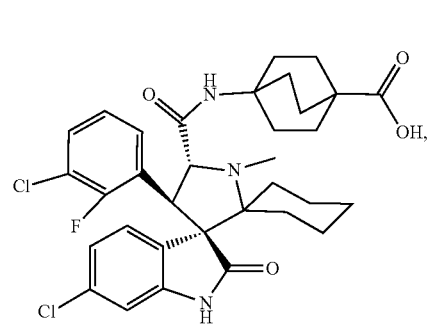
Compound Y
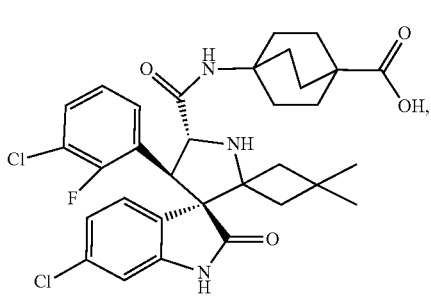
Compound K
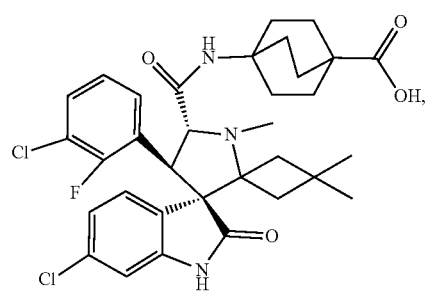

-continued

Compound P

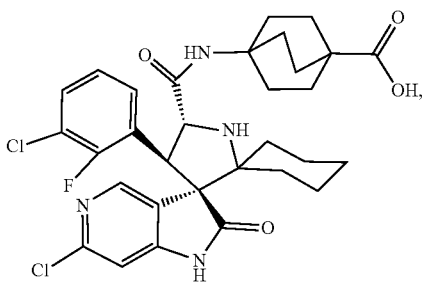

Compound T

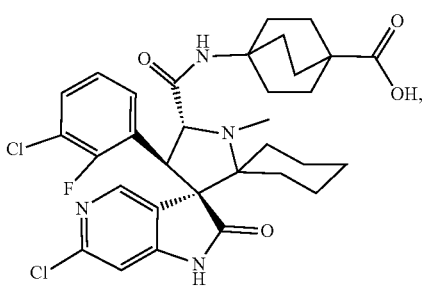

Compound S

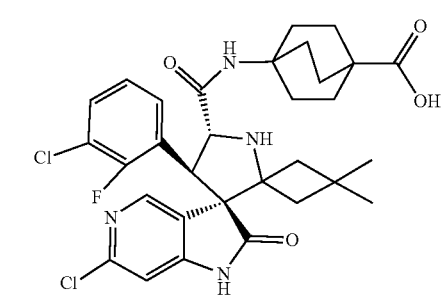

and

Compound W

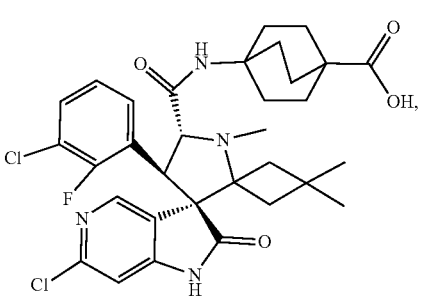

or a pharmaceutically acceptable salt thereof.

In one embodiment, the MDM2 inhibitor is

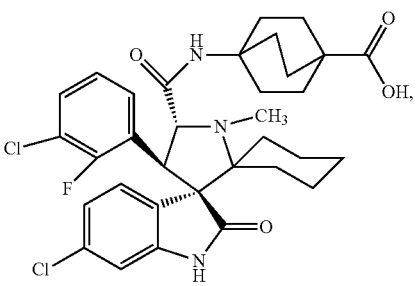 [SMILES: CN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

or a pharmaceutically acceptable salt thereof.

In one embodiment, the MDM2 inhibitor is

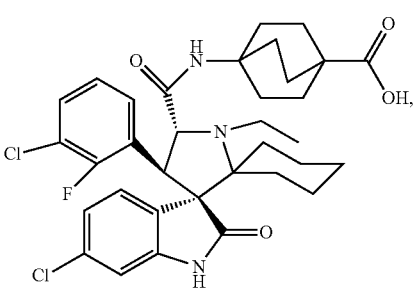 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

or a pharmaceutically acceptable salt thereof.

More MDM2 inhibitors and the synthesis of the MDM2 inhibitors that can be used in the present application are further disclosed in U.S. Pat. No. 9,745,314, which is incorporated herein by reference.

Second Anti-Cancer Therapeutic Agent

In some embodiments, an effective amount of second anti-cancer therapeutic agent is administered in combination with an MDM2 inhibitor or a Bcl-2/Bcl-xL inhibitor or a Bcl-2 inhibitor or Bcl-xL inhibitor to a subject as identified by the method as provided herein as likely to respond to the treatment with an MDM2 inhibitor a Bcl-2/Bcl-xL dual inhibitor or a Bcl-xL inhibitor or a Bcl-2 inhibitor.

In some embodiments, an effective amount of second anti-cancer therapeutic agent is administered in combination with an MDM2 inhibitor or a Bcl-2/Bcl-xL inhibitor or a Bcl-2 inhibitor or Bcl-xL inhibitor to a subject as identified by the method as provided herein as having reduced likelihood to respond to the treatment with an MDM2 inhibitor a Bcl-2/Bcl-xL dual inhibitor or a Bcl-xL inhibitor or a Bcl-2 inhibitor.

In some embodiments, an effective amount of second anti-cancer therapeutic agent in combination with an effective amount of the MDM2 inhibitor or Bcl-2/Bcl-xL dual inhibitor or Bcl-2 inhibitor or Bcl-xL inhibitor is administered to a subject having been determined to have a post-treatment change of at least one biomarker comprising Noxa, ASCL1 or both that does not reach a predetermined threshold as described herein.

In some embodiments, the MDM2 inhibitor or Bcl-2/Bcl-xL dual inhibitor or Bcl-2 inhibitor or Bcl-xL inhibitor is administered at a dosage that is different (e.g. lower) than the standard dosages under the standard of care for treatment for a particular cancer. In certain embodiments, the administered dosage of the MDM2 inhibitor Bcl-2/Bcl-xL dual inhibitor or Bcl-2 inhibitor or Bcl-xL inhibitor is 5%, 10%, 20%, 30%, 40%, 50%, 60%, 70%, 80%, or 90% lower than the standard dosage under the standard of care for treatment for a particular cancer. In certain embodiments, the dosage administered of MDM2 inhibitor Bcl-2/Bcl-xL dual inhibitor or Bcl-2 inhibitor or Bcl-xL inhibitor is 95%, 90%, 85%, 80%, 75%, 70%, 65%, 60%, 55%, 50%, 45%, 40%, 35%, 30%, 25%, 20%, 15%, 10% or 5% of the standard dosage under the standard of care for treatment for a particular cancer.

In a particular embodiment, the second anti-cancer therapeutic agent is an agent that can be used to treat a cancer. For example, the second anti-cancer therapeutic agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the second anti-cancer therapeutic agent may be a traditional small organic chemical molecules or can be macromolecules such as a proteins, antibodies, peptibodies, DNA, RNA or fragments of such macromolecules.

In some embodiments, the additional pharmaceutically active agent is a modulator of an immune checkpoint molecule.

As used herein, an "immune checkpoint" or "immune checkpoint molecule" is a molecule in the immune system that modulates a signal. An immune checkpoint molecule can be a co-stimulatory checkpoint molecule, i.e., turn up a signal, or an inhibitory checkpoint molecule, i.e., turn down a signal. A "co-stimulatory checkpoint molecule" as used herein is a molecule in the immune system that turns up a signal or is co-stimulatory. An "inhibitory checkpoint molecule", as used herein is a molecule in the immune system that turns down a signal or is co-inhibitory.

As used herein, a "modulator of an immune checkpoint molecule" is an agent capable of altering the activity of an immune checkpoint in a subject. In certain embodiments, a modulator of an immune checkpoint molecule alters the function of one or more immune checkpoint molecules including PD-1, PD-L1, PD-L2, CTLA-4, TIM-3, LAG3, CD160, 2B4, TGF β, VISTA, BTLA, TIGIT, LAIR1, OX40, CD2, CD27, ICAM-1, NKG2C, SLAMF7, NKp80, CD160, B7-H3, LFA-1, 1COS, 4-1BB, GITR, CD30, CD40, BAFFR, HVEM, CD7, LIGHT, and CD83. The modulator of the immune checkpoint may be an activator (e.g., an agonist) or an inhibitor (e.g., an antagonist) of the immune checkpoint. In some embodiments, the modulator of the immune checkpoint molecule is an immune checkpoint binding protein (e.g., an antibody, antibody Fab fragment, divalent antibody, antibody drug conjugate, scFv, fusion protein, bivalent antibody, or tetravalent antibody). In some embodiments, the modulator of the immune checkpoint molecule is a monoclonal antibody or an antigen binding fragment thereof. In other embodiments, the modulator of the immune checkpoint molecule is a small molecule. In a particular embodiment, the modulator of the immune checkpoint molecule is an anti-PD1 antibody. In a particular embodiment, the modulator of the immune checkpoint molecule is an anti-PD-L1 antibody. In a particular embodiment, the modulator of the immune checkpoint molecule is an anti-CTLA-4 antibody.

In some embodiments, the modulator of the immune checkpoint molecule restores anti-tumor T-cell activity or blocks T-cell-inhibitory cell activity. In some embodiment, the modulator of the immune checkpoint molecule is an activator of the co-stimulatory checkpoint molecule, and the activator of co-stimulatory checkpoint molecule alters co-stimulatory signal required for full T-cell activation.

In some embodiments, the modulator of the immune checkpoint molecule is pembrolizumab, ipilimumab, nivolumab, atezolizumab, avelumab, durvalumab AGEN-1884, BMS-986016, CS-1002, LAG525, MBG453, MEDI-1884, OREG-103/BY40, lirilumab, tremelimumab, nivolumab, AMP-224, AMP-514, BGB-A317, cemiplimab, JS001, PDR-001, CS-1001, PF-06801591, IBI-308, pidilizumab, SHR-1210, or TSR-042, JS003, LY3300054, MDX-1105, SHR-1316, KN035, or CK-301.

In some embodiments, the second anti-cancer therapeutic agent is a chemotherapeutic drug, either biological (macromolecule) or chemical (small molecule) compound that can be used to treat cancer. The types of chemotherapeutic drugs include, but are not limited to, histone deacetylase inhibitor (HDACI), alkylating agents, antimetabolites, alkaloids, cytotoxic/anti-cancer antibiotics, topoisomerase inhibitors, tubulin inhibitors, proteins, antibodies, kinase inhibitors, and the like. Chemotherapeutic drugs include compounds for targeted therapy and non-targeted compounds of conventional chemotherapy.

Non-limiting examples of chemotherapeutic drugs include: erlotinib, afatinib, docetaxel, adriamycin, 5-FU (5-fluorouracil), panobinostat, gemcitabine, cisplatin, carboplatin, paclitaxel, bevacizumab, trastuzumab, pertuzumab, metformin, temozolomide, tamoxifen, doxorubicin, rapamycin, lapatinib, hydroxycamptothecin, trimetinib. Further examples of chemotherapeutic drugs include: oxaliplatin, bortezomib, sunitinib, letrozole, imatinib, PI3K inhibitor, fulvestrant, leucovorin, lonafamib, sorafenib, gefitinib, crizotinib, irinotecan, topotecan, valrubicin, vemurafenib, telbivinib, capecitabine, vandetanib, chlorambucil, panitumumab, cetuximab, rituximab, tositumomab, temsirolimus, everolimus, pazopanib, canfosfamide, thiotepa, cyclophosphamide; alkyl sulfonates e.g., busulfan, improsulfan and piposulfan; ethyleneimine, benzodopa, carboquone, meturedopa, uredopa, methylmelamine, including altretamine, triethylenemelamine, triethyl phosphamide, triethyl thiophosphamide and trimethylenemelamine; bullatacin, bullatacinone; bryostatin; callystatin, CC-1065 (including its adozelesin, carzelesin, bizelesin synthetic analogue), cryptophycin (in particular, cryptophycin 1 and cryptophycin 8); dolastatin, duocarmycin (including synthetic analogue KW-2189 and CB1-TM1); eleutherobin; pancratistatin, sarcodictyin, spongistatin; nitrogen mustards, e.g., chlorambucil, chlomaphazine, cyclophosphamide, estramustine, ifosfamide, bis-chloroethyl-methylamine, Mechlorethaminoxide, melphalan, novembichin, phenesterine, prednimustine, trofosfamide, uramustine, nitrosourea, e.g., carmustine, chlorozotocin, fotemustine, lomustine, nimustine, ranimnustine, antibiotics, e.g., enediyne antibiotics (e.g., calicheamicin, calicheamicin γ1I, calicheamicin ωI1, dynemicin, dynemicin A; diphosphate, e.g, clodronate, esperamicin, and neocarzinostatin chromophore and related chromoprotein enediyne antibiotics chromophore), aclacinomycin, actinomycin, all-trans retinoic acid, anthramycin, azaserine, bleomycin, actinomycin C, carabicin, carminomycin, carzinophilin, chromomycinis, actinomycin D, daunorubicin, deoxy-fluorouridine, detorubicin, 6-dizao-5-oxo-L-norleucine, morpholino-doxorubicin, cyno-morpholino-doxorubicin, 2-pyrroline-doxorubicin, eoxy doxorubicin, epirubicin, esorubicin, idarubicin, marcellomycin, mitomycin, mycophenolic acid, nogalamycin, olivomycin, peplomycin, porfiromycin, puromycin, quelamycin, rodorubicin, streptonigrin, streptozocin, tubercidin, ubenimex, zinostatin, zorubicin; antimetabolite, e.g., methotrexate;

folate analogue, e.g., dimethylfolate, methotrexate, pteropterin, trimetrexate, purine analogue, e.g., fludarabine, 6-mercaptopurine, methotrexate, thiamiprine, tioguanine; pyrimidine analogue, e.g., ancitabine, azacitidine, azathioprine, bleomycin, 6-nitrouridine, carmofur, cytarabine, dideoxyuridine, doxifluridine, enocitabine, floxuridine; androgen, calusterone, dromostanolone propionate, epitiostanol, mepitiostane, testolactone; antiadrenergic agent, e.g. aminoglutethimide, mitotane, trilostane; folate supplement, e.g. folinate; aceglatone; aldophosphamide glycoside; aminolevulinic acid; eniluracil, amsacrine, bestrabucil, bisantrene, edatraxate, defofamine, demecolcine, diaziquone, elfomithine, elliptinium acetate, epothilone, etoglucid; gallium nitrate; hydroxycarbamide; lentinan, lonidainine, maytansinoid, maytansine, ansamitocin, mitoguazone, mitoxantrone, mopidamol, nitraerine, pentostatin, phenamet, pirarubicin, losoxantrone, podophyllinic acid; 2-ethylhydrazine; procarbazine, PSK® polysaccharide complex (JHS Natural Products, Eugene, OR), razoxane, rhizoxin, sizofiran, spirogermanium, tenuazonic acid, triaziquone; 2,2',2"-trichloro-triethylamine; trichothecene (in particular, T-2toxin, verracurin A, roridin A and anguidine); urethane, vindesine, dacarbazine, mannomustine; dibromomannitol; dibromodulcitol; pipobroman, gacytosine, arabinoside ("Ara-C"); cyclophosphamide; thiotepa; tioguanine; 6-mercaptopurine; methotrexate; Vinblastine; etoposide, ifosfamide, mitoxantrone, vincristine, vinorelbine, novantrone; pemetrexed; teniposide, edatrexate, daunomycin; aminopterin; ibandronate; CPT-11; topoisomerase inhibitor RFS 2000; DMFO, retinoid, e.g., Retinoic acid; and a pharmaceutically acceptable salt or derivative thereof.

The chemotherapeutic drug used herein is preferably selected from the group consisting of panobinostat, actinomycin, all-trans retinoic acid, azacitidine, azathioprine, bleomycin, bortezomib, carboplatin, capecitabine, cisplatin, chlorambucil, cyclophosphamide, cytosine arabinoside, daunorubicin, docetaxel, 5-fluorouracil, deoxyfluorouridine, doxorubicin, epirubicin, adriamycin, epothilone, etoposide, fluorouracil, gemcitabine, hydroxyurea, idarubicin, imatinib, irinotecan, nitrogen mustard, Mercaptopurine, methotrexate, mitoxantrone, oxaliplatin, paclitaxel, pemetrexed, teniposide, thioguanine, topotecan, valrubicin, vemurafenib, vinblastine, vincristine, vindesine, vinorelbine and hydroxycamptothecin.

In some embodiments, an immune checkpoint molecule is administered as a second anti-cancer therapeutic agent in combination with an MDM2 inhibitor. In some embodiments, a chemotherapeutic agent is administered as a second anti-cancer therapeutic agent in combination with a Bcl-2/Bcl-xL inhibitor or a Bcl-2 inhibitor or a Bcl-xL inhibitor. The second anti-cancer therapeutic can be administered simultaneously, separately or sequentially with the MDM2 inhibitor or Bcl-2/Bcl-xL inhibitor or Bcl-2 inhibitor or Bcl-xL inhibitor.

Kits

In another aspect, the present disclosure further provides one or more reagents useful in any of the assays as described herein for measuring the level of the at least one biomarker provided herein. The reagents can be primers, probes and antibodies.

In some embodiments, the present disclosure provides oligonucleotide probes attached to a solid support, such as an array slide or chip, e.g., as described in Eds., Bowtell and Sambrook *DNA Microarrays: A Molecular Cloning Manual* (2003) Cold Spring Harbor Laboratory Press. Construction of such devices are well known in the art, for example as described in US patents and patent Publications U.S. Pat. No. 5,837,832; PCT application WO95/11995; U.S. Pat. Nos. 5,807,522; 7,157,229, 7,083,975, 6,444,175, 6,375,903, 6,315,958, 6,295,153, and 5,143,854, 2007/0037274, 2007/0140906, 2004/0126757, 2004/0110212, 2004/0110211, 2003/0143550, 2003/0003032, and 2002/0041420. Nucleic acid arrays are also reviewed in the following references: *Biotechnol Annu Rev* (2002) 8:85-101; Sosnowski et al. *Psychiatr Genet* (2002)12(4): 181-92; Heller, *Annu Rev Biomed Eng* (2002) 4: 129-53; Kolchinsky et al., *Hum. Mutat* (2002) 19(4):343-60; and McGail et al., *Adv Biochem Eng Biotechnol* (2002) 77:21-42.

In another aspect, the present disclosure provides kits for use in the methods described above. Typically, the kit contain reagents useful in any of the methods provided herein in a carrier or compartmentalized container. The carrier can be a container or support, in the form of, e.g., bag, box, tube, rack, and is optionally compartmentalized.

The kits comprise one or more of the primers, the probes, and/or the antibodies, or microarray provided herein. The primers, the probes, and/or the antibodies may or may not be detectably labeled. In certain embodiments, the kits may further comprise other reagents to perform the methods described herein. In such applications the kits may include any or all of the following: suitable buffers, reagents for isolating nucleic acid, reagents for amplifying the nucleic acid (e.g. polymerase, dNTP mix), reagents for hybridizing the nucleic acid, reagents for sequencing the nucleic acid, reagents for quantifying the nucleic acid (e.g. intercalating agents, detection probes), reagents for isolating the protein, and reagents for detecting the protein (e.g. antibody).

In certain embodiments, the kits can further comprise a standard negative control, and/or a standard positive control.

In addition, the kits may include instructional materials containing directions (i.e., protocols) for the practice of the methods provided herein. While the instructional materials typically comprise written or printed materials they are not limited to such.

In certain embodiments, the kits can further comprise a computer program product stored on a computer readable medium. When computer program product is executed by a computer, it performs the step of comparing the level of the at least one biomarker with a corresponding reference level of the at least one biomarker to determine difference from the reference level. Any medium capable of storing such computer executable instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The computer programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

This example shows the correlation between Noxa expression and compound efficacy of Compound A15 in gastric cancer PDX models and esophageal cancer PDX models.

Materials and Methods

Twelve gastric PDX cancer models and 4 esophageal cancer PDX models were selected for efficacy study. Mice bearing patient-derived xenograft (PDX) were randomly allocated to the 2 different study groups, based on their tumor volume. The mean tumor volume at randomization was 100-200 mm³. Randomization was performed based on "Matched distribution" randomization method (StudyDirector™ software) on day 1. Mice was either administered with vehicle or Compound A15 for 21 days (i.v. biw).

Tumor volumes were measured twice weekly in two dimensions using a caliper, and the volume was expressed in mm3 using the formula: Tumor Volume (mm3)=0.5 a×b2 where a and b are the long and short diameters of the tumor, respectively. Relative tumor volume (RTV) was calculated using the following formula: RTV=Vt/V1 where V1 and Vt are the average tumor volumes on the first day of treatment (Day 1) and the average tumor volumes on a certain time point. Percent tumor growth inhibition (% T/C) was calculated as the mean RTV of treated tumors (T) divided by the mean RTV of control tumors (C)×100%. The percentage T/C value is an indication of antitumor effectiveness: a value of T/C<42% is considered significant antitumor activity by the NCI. A T/C value <10% is considered to indicate highly significant antitumor activity, and is the level used by the NCI to justify a clinical trial if toxicity and certain other requirements are met (termed DN-2 level activity). A body weight loss (mean of group) of greater than 20%, or greater than 20% of drug deaths are considered to indicate an excessively toxic dosage. All data were analyzed in SPSS (Statistical Product and Service Solutions) version 18.0 (IBM, Armonk, NY, U.S.). Prism version 6 (GraphPad Software Inc., San Diego, CA) was used for graphic presentation. $R^2$ (correlation of determination) shows percentage variation in y which is explained by all the x variables which ranges from 0 to 1. 1 indicates the strongest possible agreement, a perfect correlation.

Results

Figure 1B:
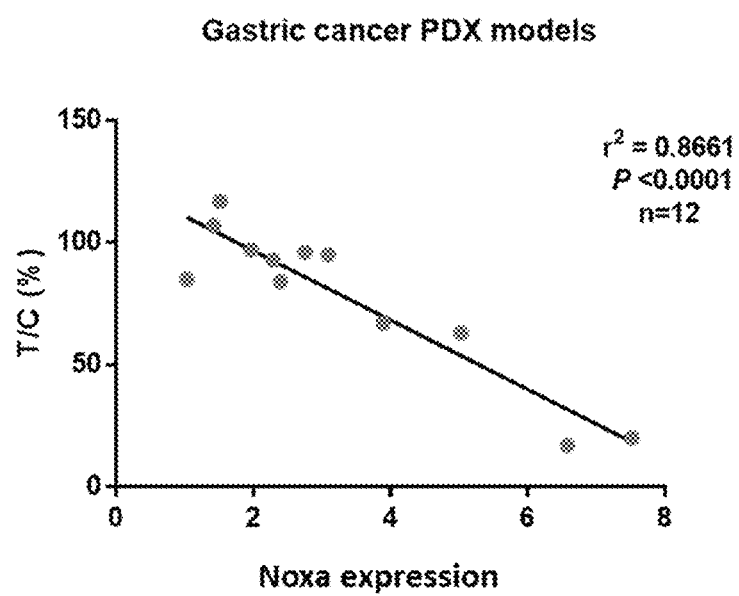

In the efficacy trial in gastric cancer PDX models, 12 PDX models (Bcl-xL$^{hi}$, Bcl2$^{hi}$, Mcl1$^{low-normal}$) were employed and treated with 100 mg/kg Compound A15, i.v., biw for 21 days (7 doses in total). T/C values of these models varied between 17-117 (FIGS. 1A and 1B) (T/C value, average tumor volumes in treatment group vs. the vehicle control group). RNA sequencing has been performed for these models, and the RNA sequencing data are represented as Log 2 (FPKM), where FPKM refers to Fragments Per Kilobase of transcript per Million mapped reads. Based on the RNA sequencing data, the expression level of Noxa ranged from 1.0354 to 7.5223 (represented by Log 2 (FPKM)) in these models. T/C values and respective RNA expression was analyzed through linear regression and R squared was calculated to be 0.8661, indicating 86.61% variation in T/C can be explained by the RNA expression of Noxa (p<0.0001).

Figure 2A:
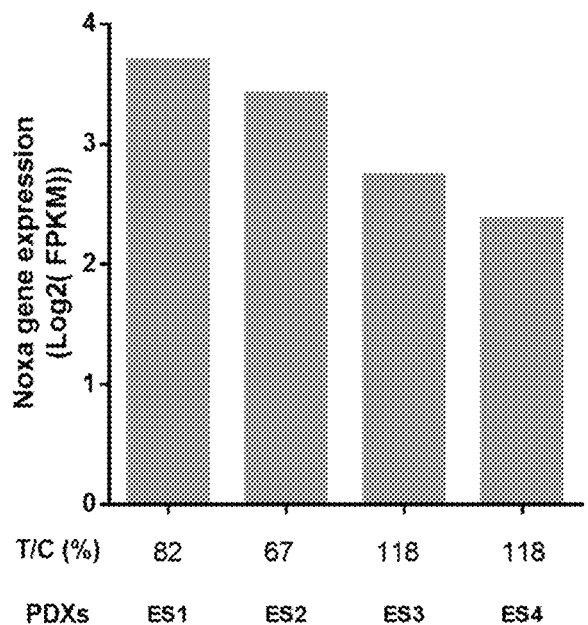
FIGS. 2A and 2B illustrate that Noxa expression level correlates with tumor regression in esophageal cancer PDX (patients derived xenograft) models treated with Bcl-2/Bcl-xL dual inhibitor Compound A15.
Figure 2B:
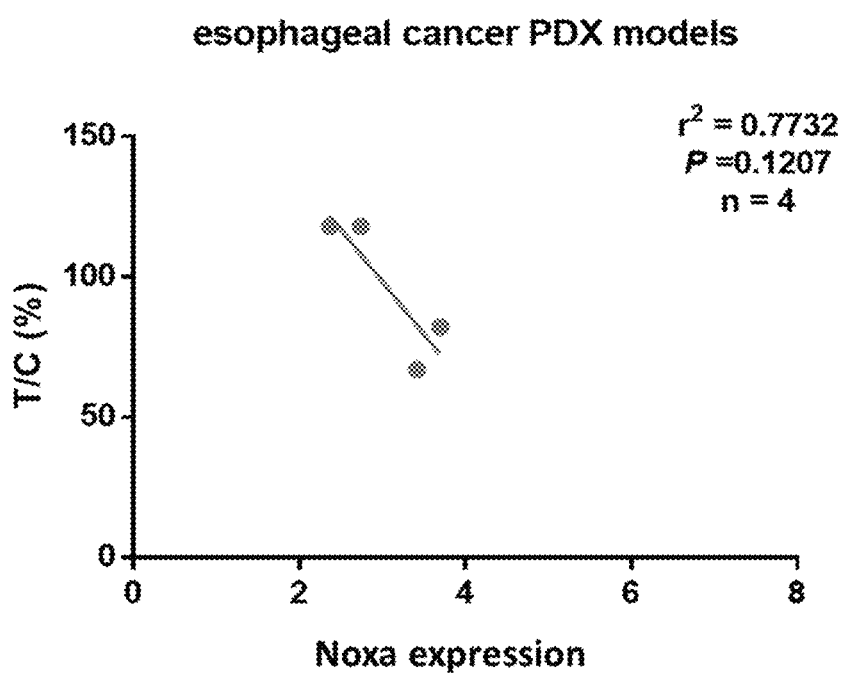
Figure 3A:
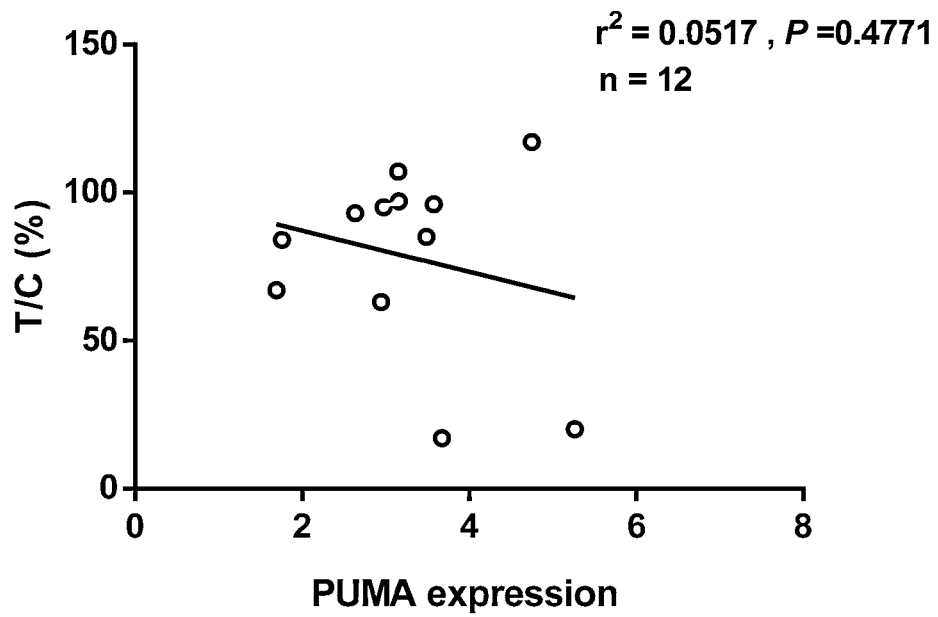
FIGS. 3A to 3E illustrate the correlation of additional biomarkers including PUMA (FIG. 3A), BIM (FIG. 3B), Bcl-xL (FIG. 3C), and Mcl-1 (FIG. 3D), Bcl-2 (FIG. 3E) to tumor regression in the gastric cancer PDX models.
Figure 3B:
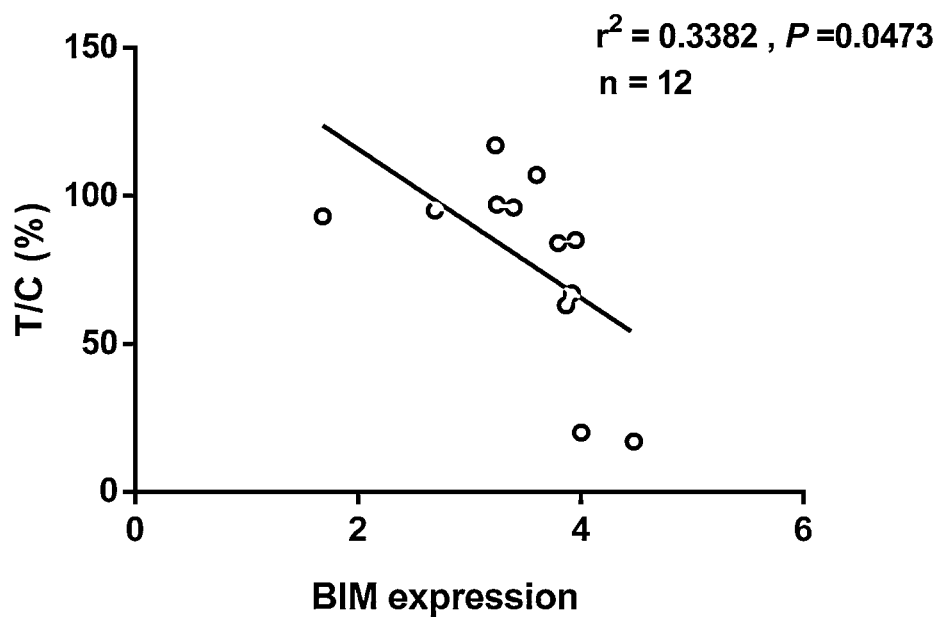
Figure 3C:
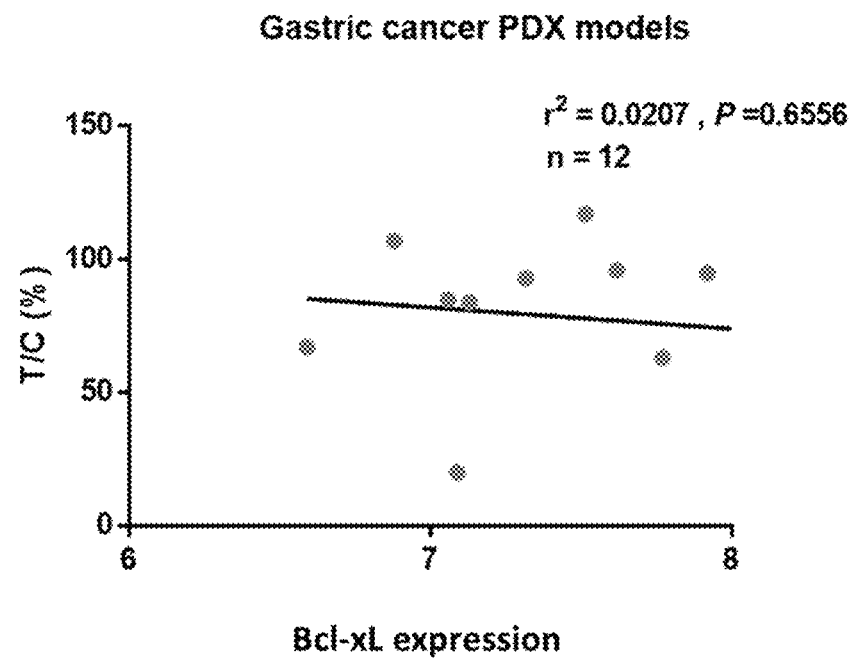
Figure 3D:
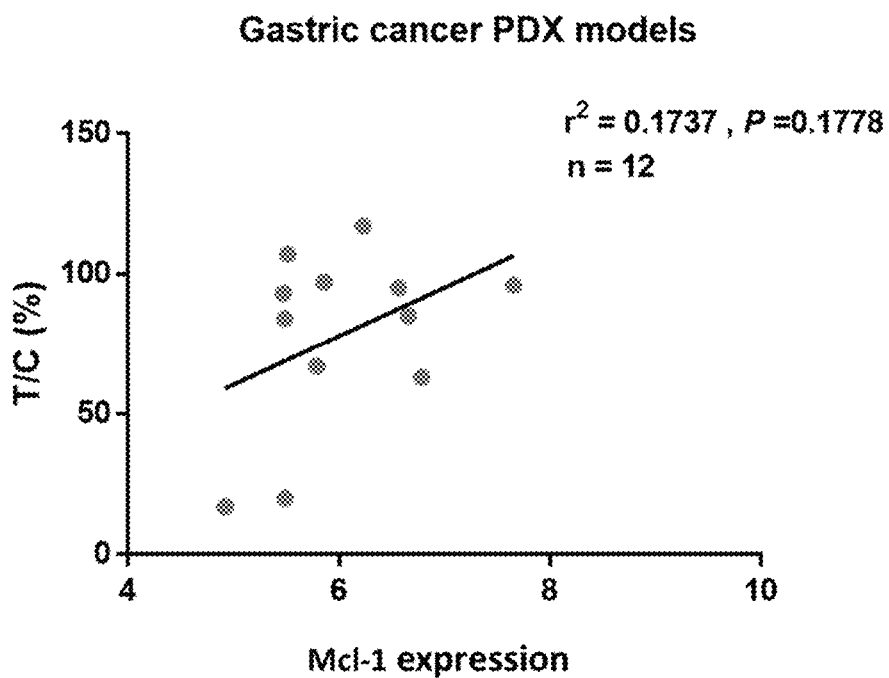
Figure 3E:
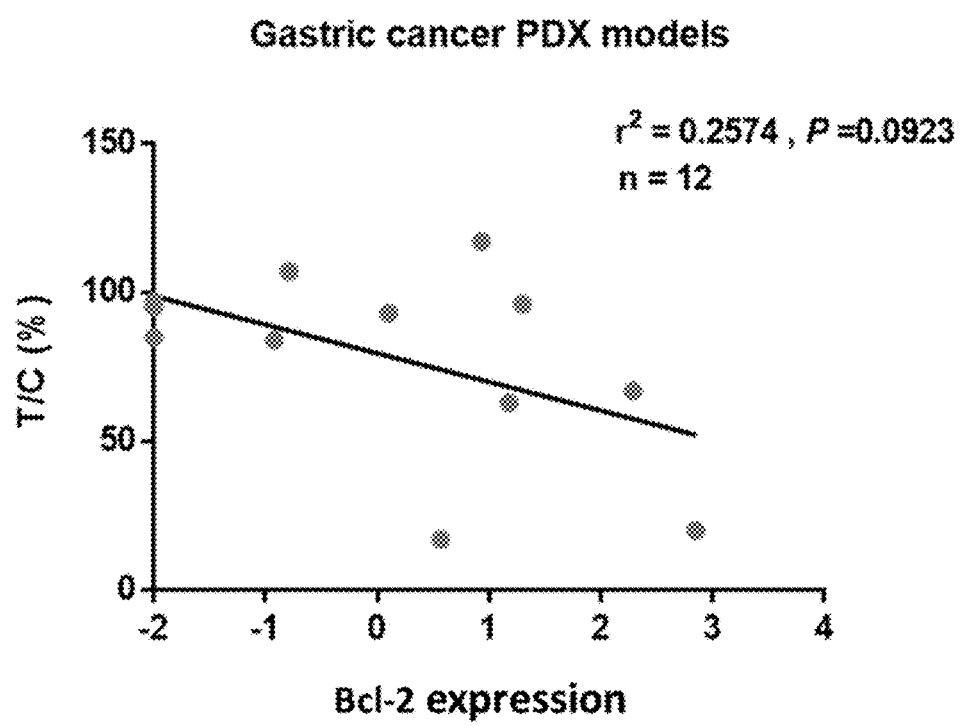

From an independent set of experiments, whereas esophageal cancer PDX models were employed (n=4), similar correlation between T/C and expression of Noxa was observed (FIGS. 2A and 2B). $R^2$ value was recorded as 0.7732 with P<0.05.

Correlation of T/C with the RNA expression of Bcl-2, Bcl-xL, Mcl-1, BIM and PUMA are also tested and the R squared are respectively shown in FIG. 3: 0.2574 (Bcl-2, FIG. 3E), 0.0207 (Bcl-xL, FIG. 3C), 0.1737 (Mcl-1, FIG. 3D), 0.3382 (BIM, FIG. 3B) and 0.0517 (PUMA, FIG. 3A) respectively.

In summary, RNA expression level of Noxa highly correlates with degree of tumor regression in Bcl-2/Bcl-xL dual inhibitor Compound A15 treated gastric and esophageal cancer PDX models. This correlation is much higher than any other biomarkers tested: BIM, Mcl-2, Bcl-2, PUMA and Bcl-xL.

Example 2

This study shows Compound B4 is more dependent on Bcl-xL than on Bcl-2 in function as a Bcl-2/Bcl-xL dual inhibitor.

ABT-737 (IUPAC name: 4-{4-[(4'-Chloro-2-biphenylyl)methyl]-1-piperazinyl}-N-[(4-{[(2R)-4-(dimethylamino)-1-(phenylsulfanyl)-2-butanyl]amino}-3-nitrophenyl)sulfonyl]benzamide) is one of earliest BH3 mimetic developed by Abbott Laboratories (now Abbvie). It acts as a dual BCl-2/Bcl-xL inhibitor and promotes tumor cell apoptosis. The study compared the binding for Bcl-2 and BCl-xL between Compound B4 or ABT-737.

A diffuse large B cell lymphoma line, Toledo, and an acute lymphocytic leukemia line, RS4; 11, were chosen for the study. Cells were treated for 24 hours with Compound B4 or ABT-737 at indicated concentrations (0.025 uM, 0.04 uM and 0.06 uM, respectively) and harvested for complex analysis. Both Bcl-2:BIM and Bcl-xL:BIM complex were analyzed using MSD advanced ELISA methods.

Figure 4A:
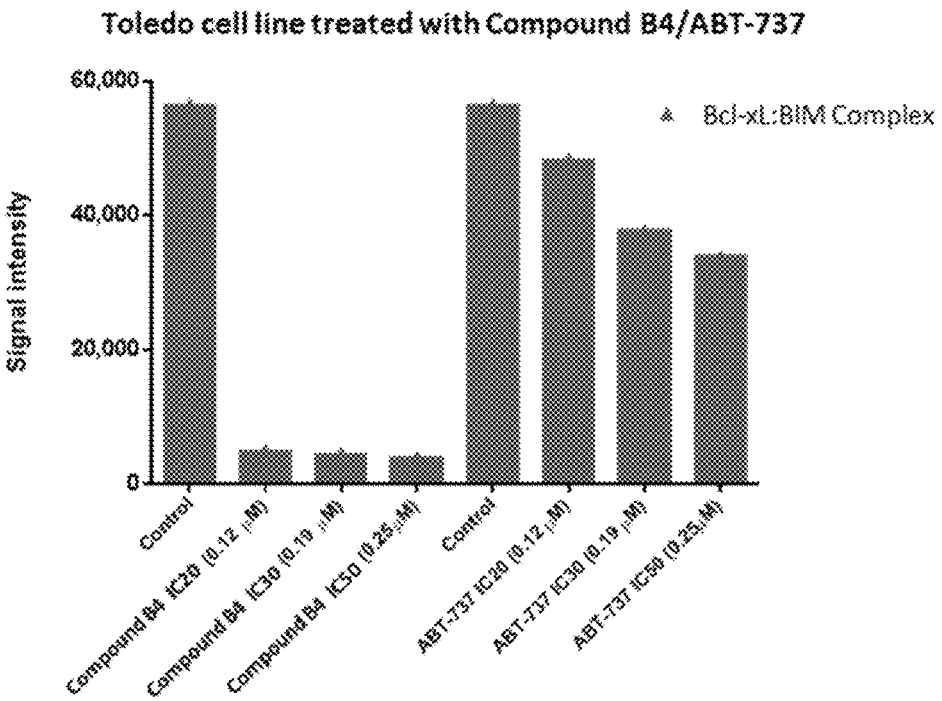
FIGS. 4A and 4B illustrate the comparison of Compound B4 and reference compound ABT-737 in reducing the level of protein complexes of Bcl-xL: BIM or Bcl2: BIM in Toledo cell line (FIG. 4A), and in RS4; 11 cell line (FIG. 4B).
Figure 4A:
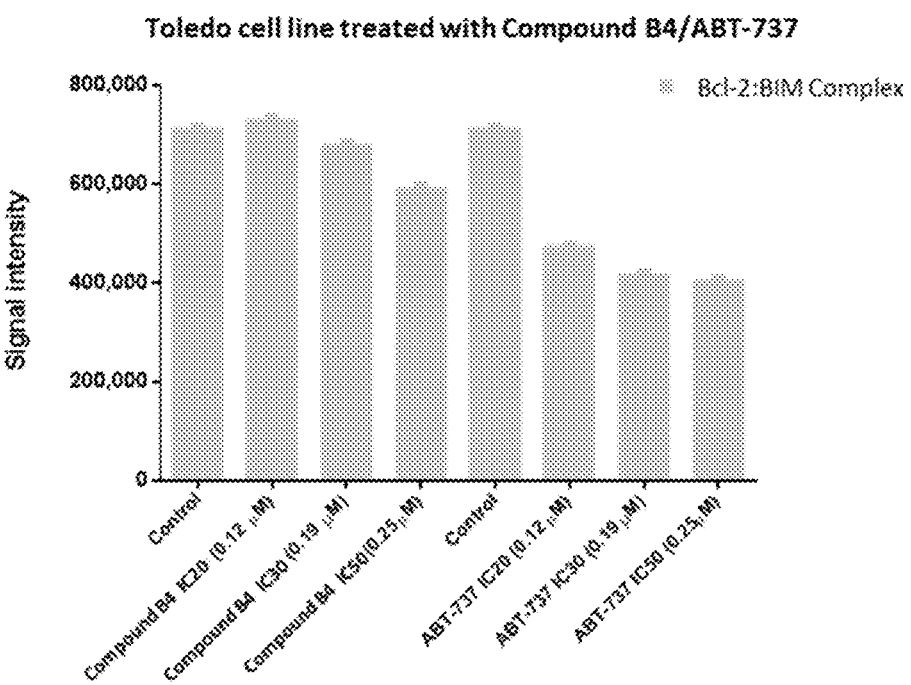
Figure 4B:
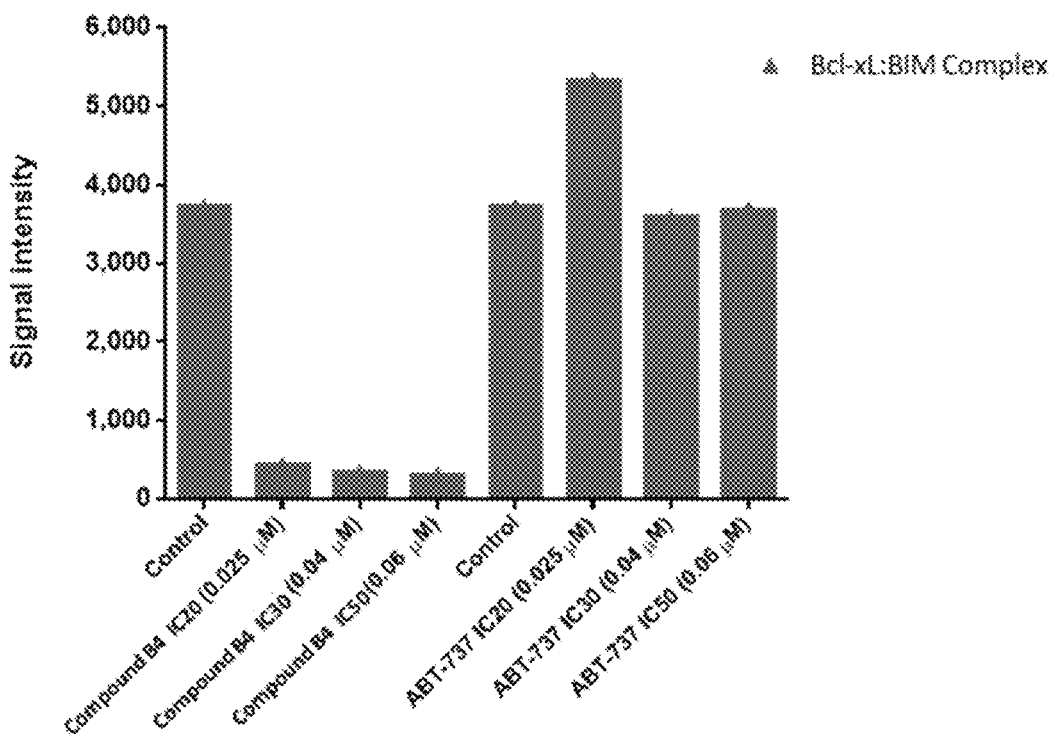
Figure 4B:
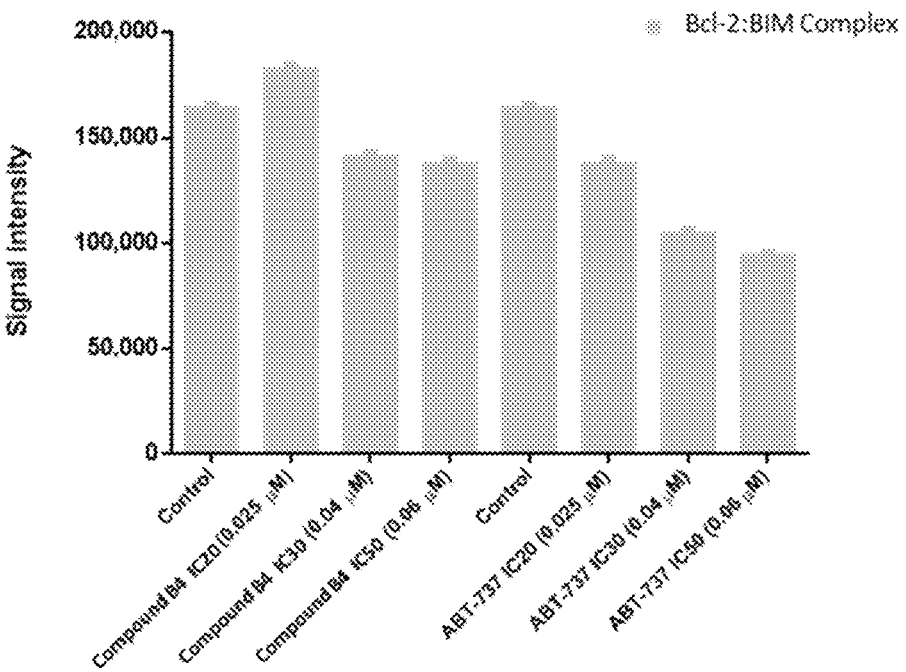

The results showed that Compound B4 more potently disrupted Bcl-xL:BIM than Bcl-2:BIM complex in Toledo (FIG. 4A) and RS4; 11 (FIG. 4B) cell lines. In particular, Compound B4 disrupted Bcl-xL:BIM complex more intensely than ABT-737.

These cell line results are consistent with relevant gastric/esophageal cancer PDX trials with Compound A15 (data not shown), confirming that both Compound A15 (in PDX) and Compound B4 (in cell line) can target Bcl-xL than Bcl-2 complex, and are distinct from the reference compound ABT-737.

Example 3

This study shows antitumor activity of Compound A15 in ASCL-1-high and Noxa-high SCLC PDX models.

SCLC is a heterogeneous disease with extremely high mutation rates but lack of identified driver oncogenes for molecular targeted therapy. It is currently treated as a single disease entity in clinics. Recent studies advanced our understanding in SCLC and distinct subtypes are characterized based on the mutual exclusive expression of either ASCL1, NEUROD1, POU2F3 or YAP1 (Rudin et al, 2019). ASCL1 expressing SCLC is the most frequent subtype accounting for 70% of cases.

Figure 5A:
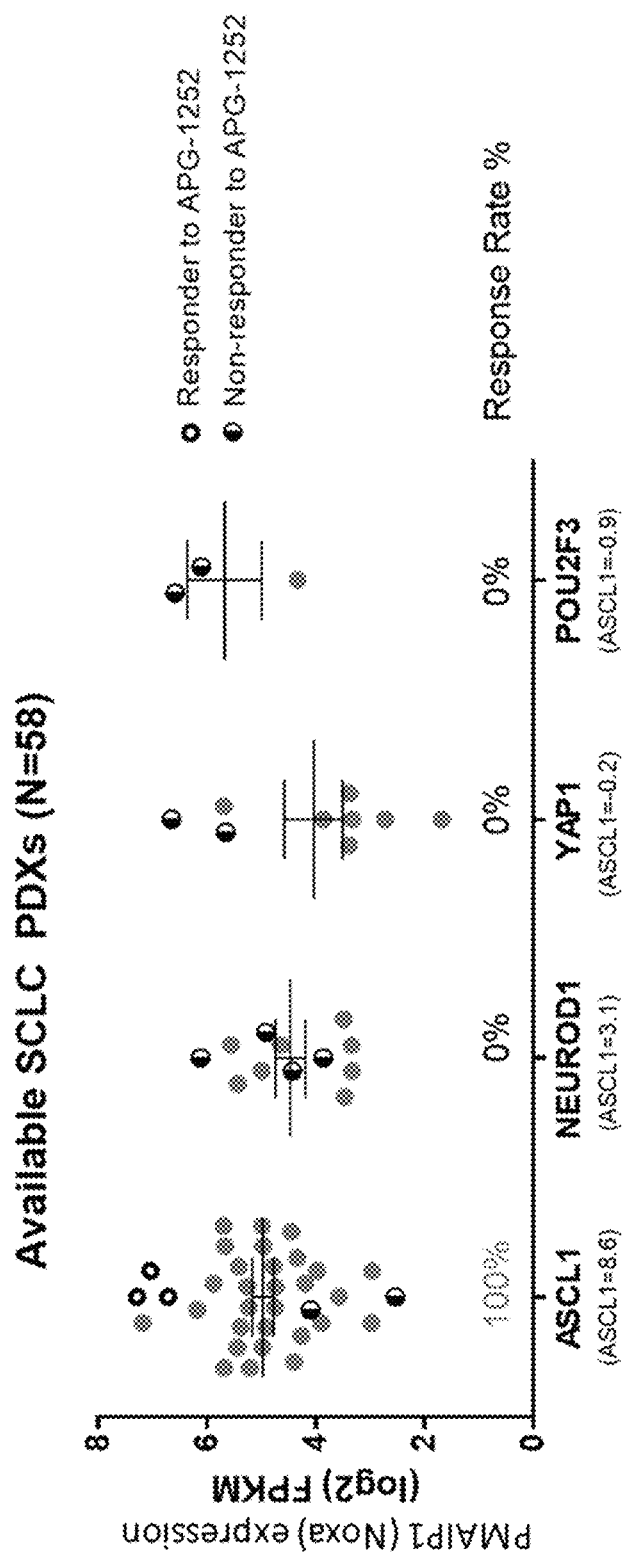
FIGS. 5A, 5B and 5C illustrate antitumor activity of Compound A15 in ASCL-1-high and Noxa-high small cell lung cancer (SCLC) PDXs (FIG. 5A), correlation between antitumor activity of Compound A15 and Noxa expression in all SCLC PDX model (FIG. 5B), and correlation between antitumor activity of Compound A15 and Noxa expression in ASCL-1-high SCLC PDXs (and 5C).

Noxa expression levels were obtained from 58 commercially available PDX models of SCLC (PDX models available from Crownbio). Noxa expression levels of these 58 PDX models have been determined by RNA sequencing, and are plotted in FIG. 5A, with each point representing one PDX model. Based on the RNA sequencing data, the expression level of Noxa ranged from below 2 to above 6 (represented by Log 2 (FPKM)) in these models. Average level of PMAIP1 (encoded protein Noxa) is shown on the plot as a straight line with error bars in FIG. 5A.

13 of these 58 PDX models are tested for antitumor activity of Compound $A_{15}$. Compound A15 monotherapy was given intravenously twice weekly at 50 mg/kg and tumor inhibition rate of 60% was set as the cut-off value for tumor regression.

Results revealed that Compound A15 achieved tumor regression in 3 of the total 13 models tested (FIG. 5A, indicated as hallow circle), but not in the other 10 tested models. Surprisingly, these three responsive models all have above-average Noxa expression (e.g. above 6 in log 2 FPKM in FIG. 5A), and also harbor ASCL1 expression. In contrast, the other 10 non-responsive models (FIG. 5A, indicated as half-filled circle) either do not show ASCL1 expression, despite of expressing NEUROD1, POU2F3 or YAP1, respectively, or show ASCL1 expression but have below-average Noxa expression. The 45 models that were not tested for antitumor activity of Compound A15 in the study were indicated as grey dots.

The results showed that ASCL1 subtype of SCLC with high Noxa expression is highly sensitive to Compound A15 monotherapy.

Figure 5B:
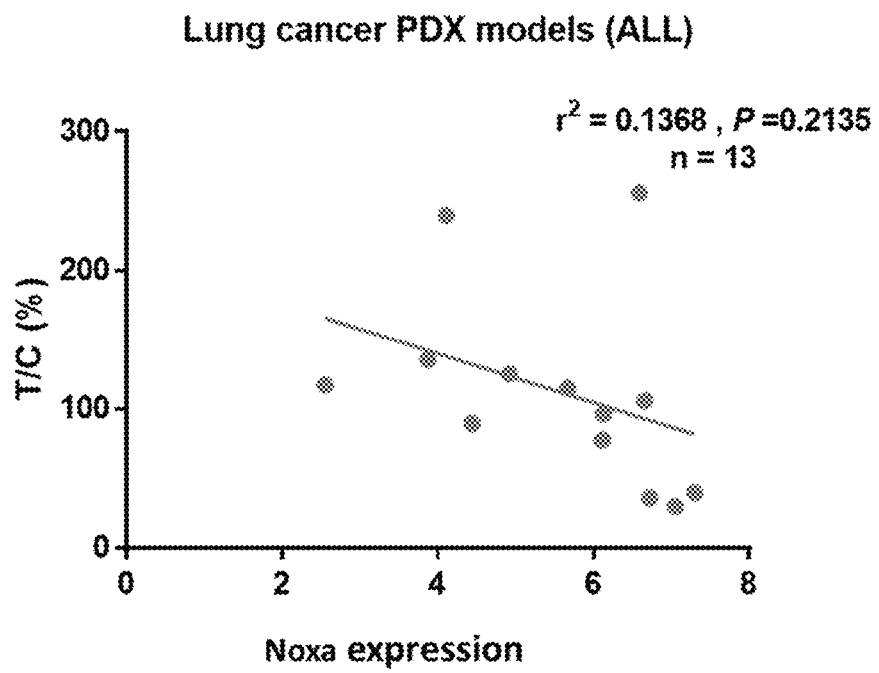
Figure 5C:
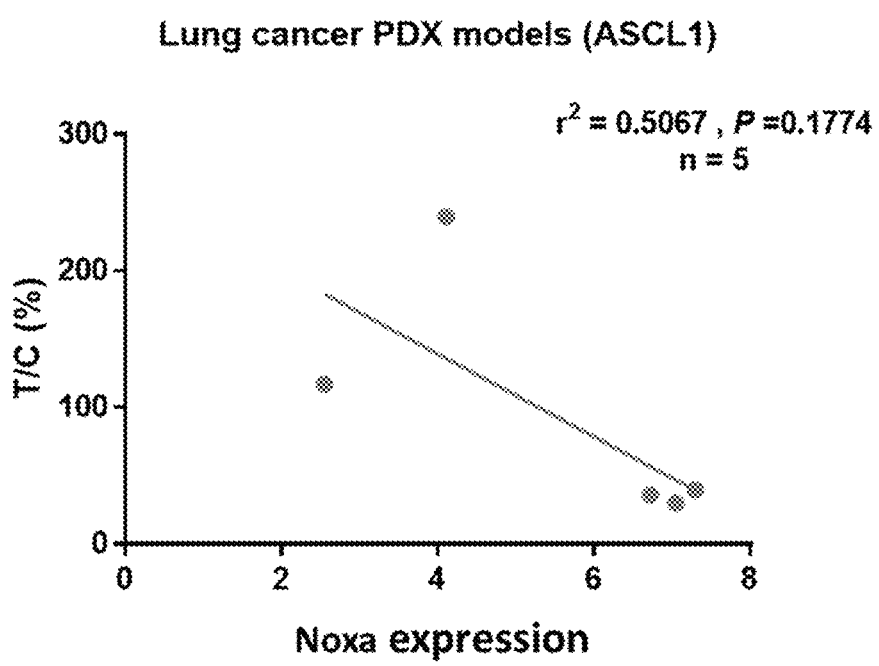

Further statistics using linear regression showed that in all test models (n=13), coefficient of determination ($R_2$) between antitumor activity of Compound A15 and Noxa expression is 0.138 (FIG. 5B). When considering ASCL-1 expression (test model 5/13), coefficient of determination ($R_2$) between antitumor activity of Compound A15 and Noxa expression can increase to 0.5067 (FIG. 5C). Our results showed that using ASCL1 and Noxa as co-biomarkers will select SCLC patients most likely responding to Compound A15 treatment.

Example 4

The object of the study is to evaluate the anti-tumor activity of MDM2 inhibitor Compound C and the level of Noxa in gastric cancer PDX models.

The experimental methods and procedures are similar to those described in Example 1. Mice was either administered with vehicle or Compound C . . . .

In the efficacy trial, the gastric cancer PDX models were employed and treated with 100 mg/kg Compound C, oral for 14 days (7 doses in total) or treated with 10-50 mg/kg Compound C, oral for QOD. The expression level of Noxa is determined by RNA sequencing. It is expected that the high expression level of Noxa relative to the reference level correlates with degree of tumor regression in Compound C treated gastric PDX models.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

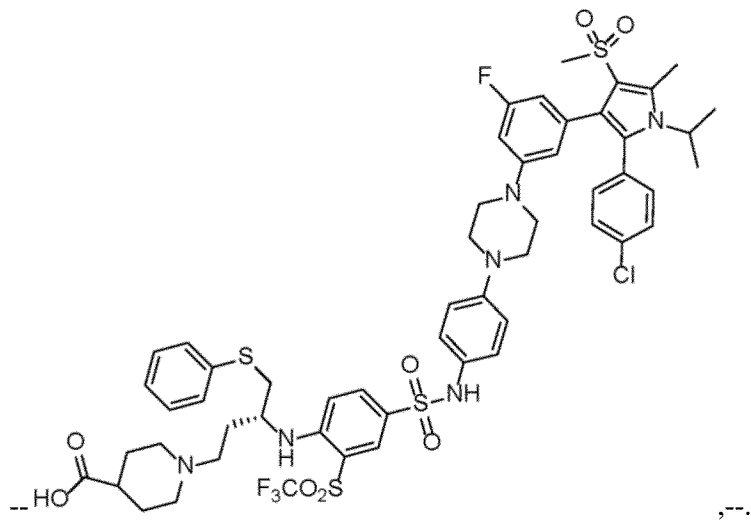

What is claimed is:

1. A method for treating a cancer in a subject in need thereof, the method comprising:

a) measuring a level of at least one biomarker comprising Noxa and ASCL1 in a test sample derived from the subject;

b) comparing the level of the at least one biomarker comprising Noxa and ASCL1 with a corresponding reference level of the at least one biomarker comprising Noxa and ASCL1 to determine difference from the reference level; and c) administering to the subject an amount of an MDM2 inhibitor, a Bcl-2/Bcl-xL dual inhibitor, a Bcl-xL inhibitor, or a Bcl-2 inhibitor to the subject-if the difference exceeds a predetermined threshold, wherein:
i) the MDM2 inhibitor is

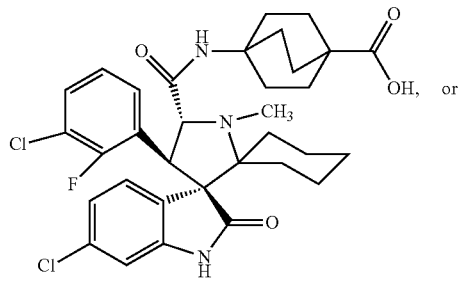

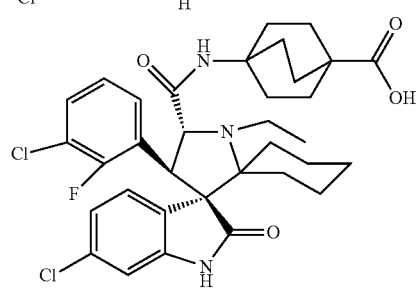

or a pharmaceutically acceptable salt thereof,
ii) the Bcl-2/Bcl-xL dual inhibitor is
(R)-2-(1-(3-(4-(N-(4-(4-(3-(2-(4-chlorophenyl)-1-iso-
propyl-5-methyl-4-(methylsulfonyl)-1H-pyrrol-3-
yl)-5-fluorophenyl) piperazin-1-yl)phenyl) sulfa-
moyl)-2-(trifluoromethylsulfonyl)phenylamino)-4-
(phenylthio)butyl) piperidine-4-carbonyloxy)
ethylphosphonic acid, having the following
structure:

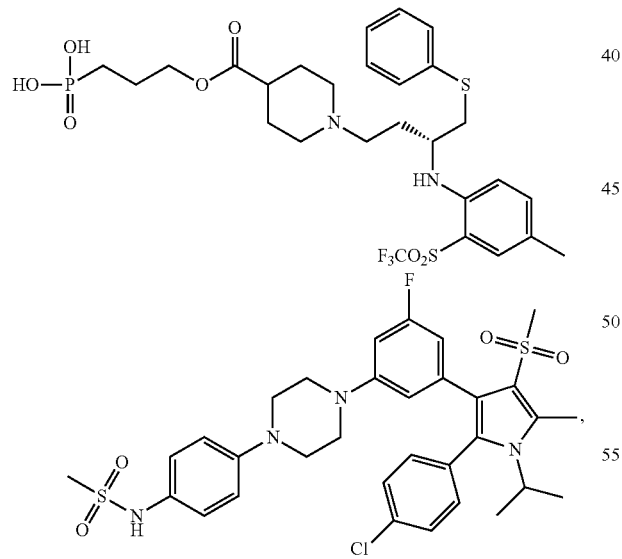

or a pharmaceutically acceptable salt thereof; or
(R)-1-(3-(4-(N-(4-(4-(3-(2-(4-chlorophenyl)-1-isopro-
pyl-5-methyl-4-(methylsulfonyl)-1H-pyrrol-3-yl)-5-
fluorophenyl) piperazin-1-yl)phenyl) sulfamoyl)-2-
(trifluoromethylsulfonyl)phenylamino)-4-
(phenylthio)butyl) piperidine-4-carboxylic acid,
having the following structure:

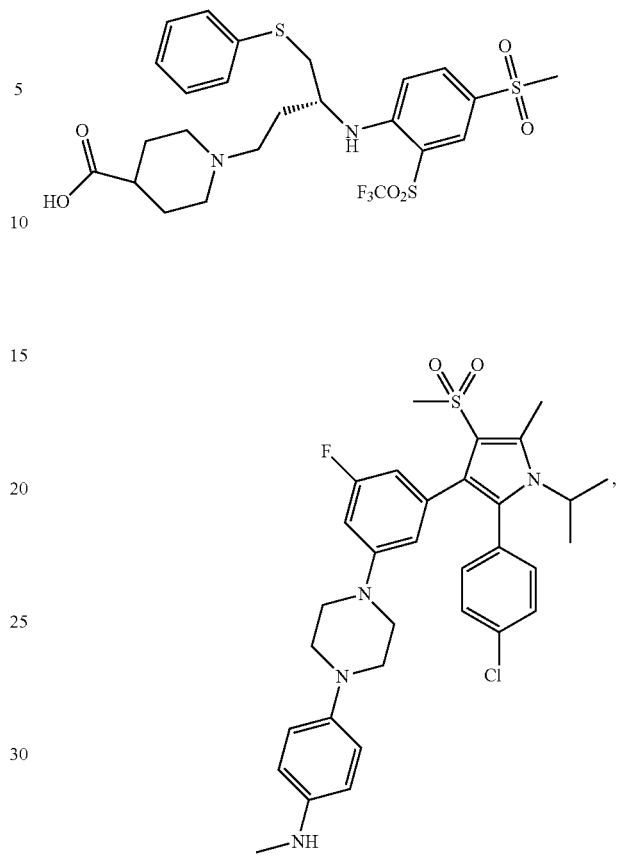

or a pharmaceutically acceptable salt thereof, and
iii) the Bcl-2/Bcl-xL dual inhibitor, Bcl-xL inhibitor, or
Bcl-2 inhibitor is selected from the compounds hav-
ing the following structures:

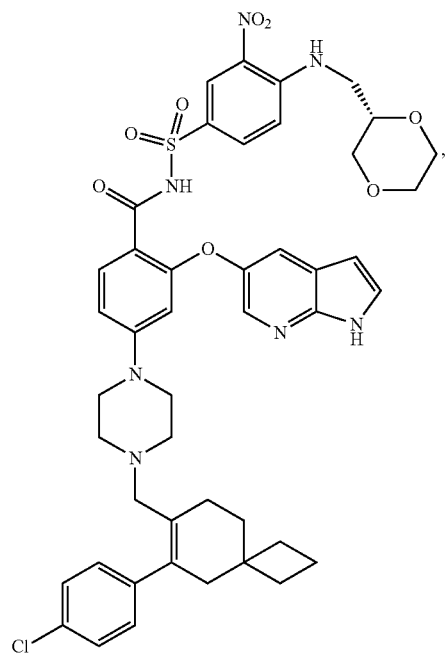 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

183

-continued

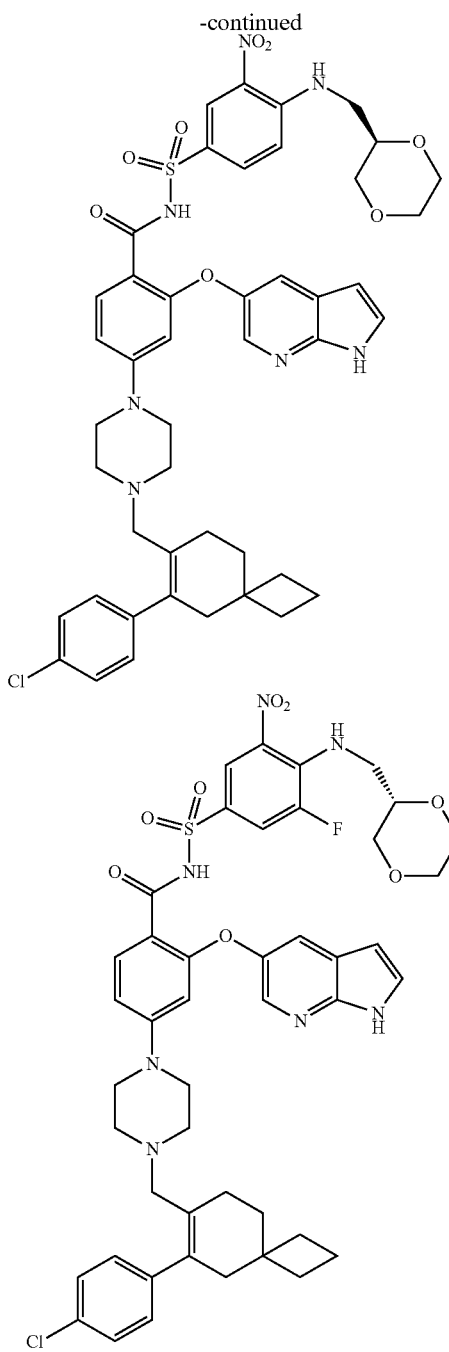

and

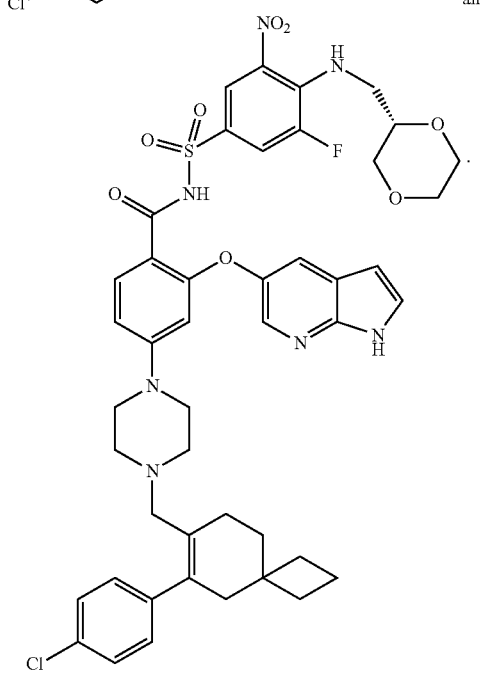

2. A method for identifying a subject having a cancer as likely to respond to treatment with an MDM2 inhibitor, a Bcl-2/Bcl-xL dual inhibitor, a Bcl-xL inhibitor, or a Bcl-2 inhibitor, the method comprising:
  a) measuring a level of at least one biomarker comprising Noxa and ASCL1 in a test sample derived from the subject;
  b) comparing the level of the at least one biomarker comprising Noxa and ASCL1 with a corresponding reference level of the at least one biomarker comprising Noxa and ASCL1 to determine difference from the reference level; and
  c) identifying the subject as likely to respond to the treatment with the MDM2 inhibitor, the Bcl-2/Bcl-xL

184 dual inhibitor, the Bcl-xL inhibitor, or the Bcl-2 inhibitor if the difference exceeds a predetermined threshold, wherein:
  i) the MDM2 inhibitor is

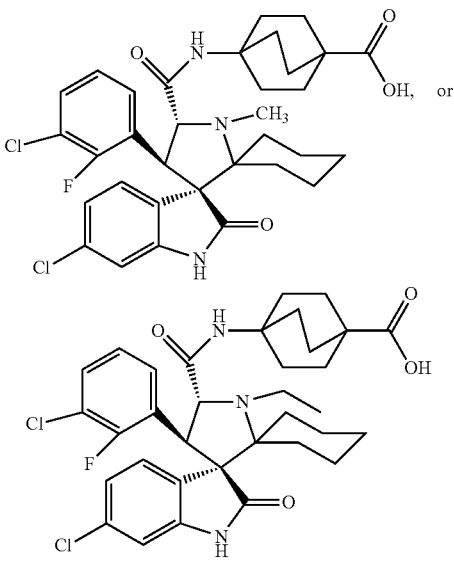

or a pharmaceutically acceptable salt thereof,
  ii) the Bcl-2/Bcl-xL dual inhibitor is
    (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl) piperazin-1-yl)phenyl) sulfamoyl)-2-(trifluoromethylsulfonyl)phenylamino)-4-(phenylthio)butyl) piperidine-4-carbonyloxy) ethylphosphonic acid, having the following structure

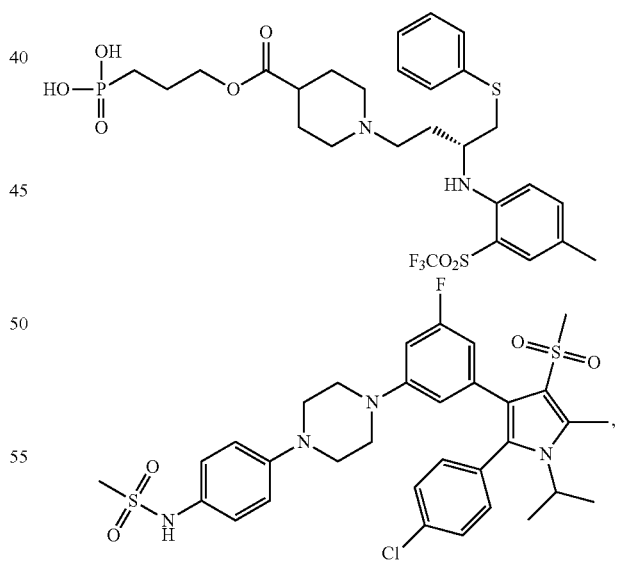

or a pharmaceutically acceptable salt thereof; or
  (R)-1-(3-(4-(N-(4-(4-(3-(2-(4-chlorophenyl)-1-isopropyl-5-methyl-4-(methylsulfonyl)-1H-pyrrol-3-yl)-5-fluorophenyl) piperazin-1-yl)phenyl) sulfamoyl)-2-(trifluoromethylsulfonyl)phenylamino)-4-(phenylthio)butyl) piperidine-4-carboxylic acid, having the following structure:

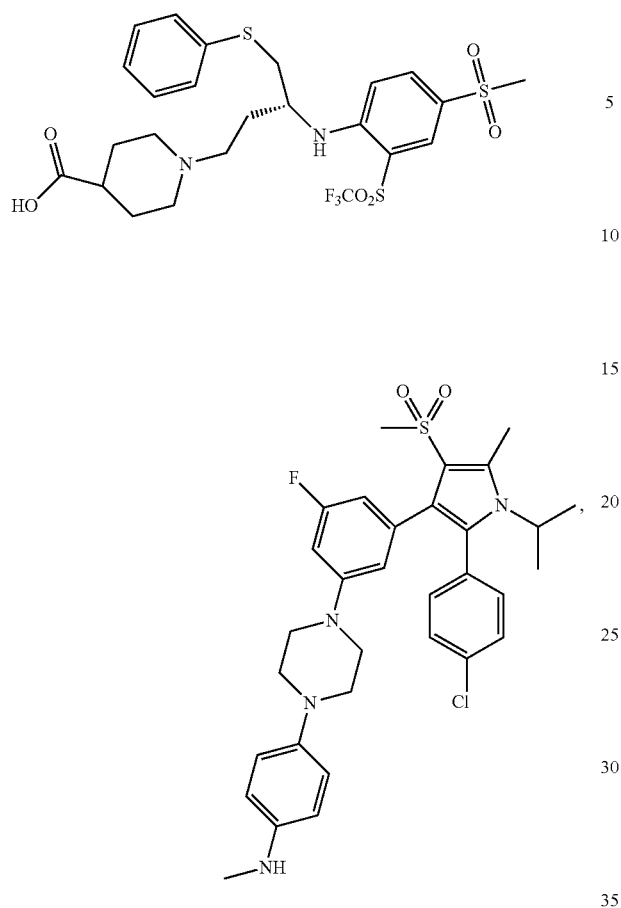

or a pharmaceutically acceptable salt thereof, and
  iii) the Bcl-2/Bcl-xL dual inhibitor, Bcl-xL inhibitor, or Bcl-2 inhibitor is selected from the compounds having the following structures:

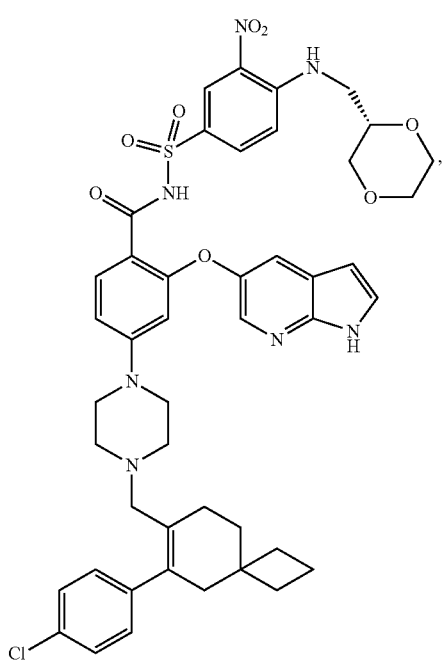 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

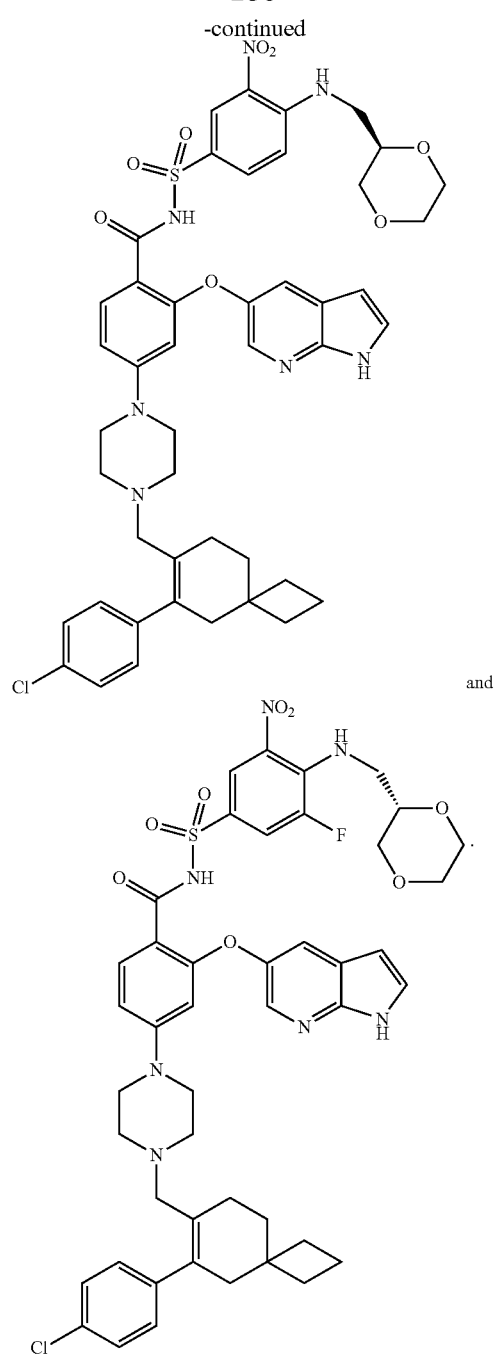

3. A method for monitoring therapeutic efficacy in a subject having a cancer and having been treated with an MDM2 inhibitor, a Bcl-2/Bcl-xL dual inhibitor, a Bcl-xL inhibitor, or a Bcl-2 inhibitor for a therapeutic period, the method comprising:
  a) obtaining a test sample from the subject after the therapeutic period;
  b) measuring a level of at least one biomarker comprising Noxa and ASCL1 in the test sample to obtain a post-treatment level of the at least one biomarker comprising Noxa and ASCL1;
  c) comparing the post-treatment level with a baseline level of the at least one biomarker comprising Noxa and ASCL1 in the test sample derived from the subject before the therapeutic period, to determine post-treatment change in the level of the at least one biomarker comprising Noxa and ASCL1; and d1) when the post-treatment change exceeds a predetermined threshold, then continuing administering to the subject the MDM2 inhibitor, the Bcl-2/Bcl-xL dual inhibitor, the Bcl-xL inhibitor, or the Bcl-2 inhibitor to the subject, or d2) when the post-treatment change does not reach the predetermined threshold, then (d2-1) increasing the dose of the MDM2 inhibitor, the Bcl-2/Bcl-xL dual inhibitor, the Bcl-xL inhibitor, or the Bcl-2 inhibitor to the subject, (d2-2) administering to the subject an amount of a second anti-cancer therapeutic agent in combination with the MDM2 inhibitor, the Bcl-2/Bcl-xL dual inhibitor, the Bcl-xL inhibitor, or the Bcl-2 inhibitor, or (d2-3) discontinuing administering to the subject the MDM2 inhibitor, the Bcl-2/Bcl-xL dual inhibitor, the Bcl-xL inhibitor, or the Bcl-2 inhibitor, wherein;

(i) the MDM2 inhibitor is

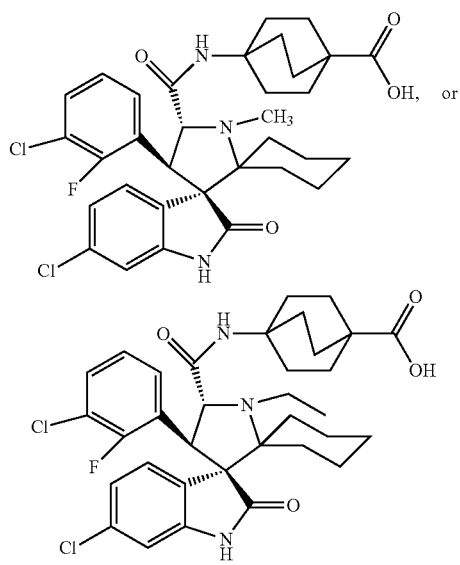

or a pharmaceutically acceptable salt thereof, (ii) the Bcl-2/Bcl-xL dual inhibitor is (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl) piperazin-1-yl)phenyl) sulfamoyl)-2-(trifluoromethylsulfonyl)phenylamino)-4-(phenylthio)butyl) piperidine-4-carbonyloxy) ethylphosphonic acid, having the following structure;

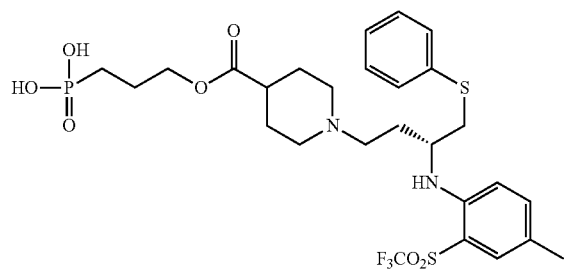

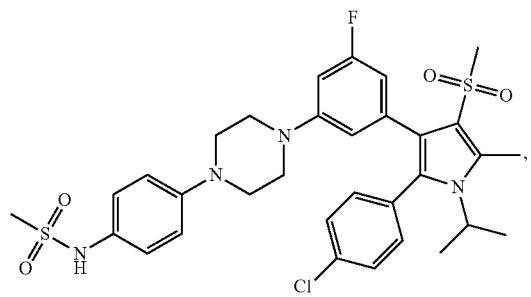

or a pharmaceutically acceptable salt thereof; or (R)-1-(3-(4-(N-(4-(4-(3-(2-(4-chlorophenyl)-1-isopropyl-5-methyl-4-(methylsulfonyl)-1H-pyrrol-3-yl)-5-fluorophenyl) piperazin-1-yl)phenyl) sulfamoyl)-2-(trifluoromethylsulfonyl)phenylamino)-4-(phenylthio)butyl) piperidine-4-carboxylic acid, having the following structure:

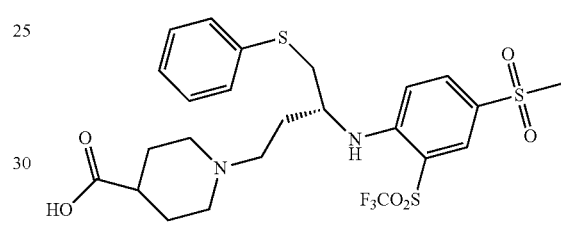

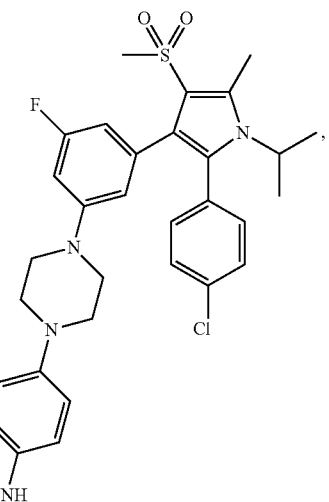

or a pharmaceutically acceptable salt thereof, and (iii) the Bcl-2/Bcl-xL dual inhibitor, Bcl-xL inhibitor, or Bcl-2 inhibitor is selected from the compounds having the following structures:

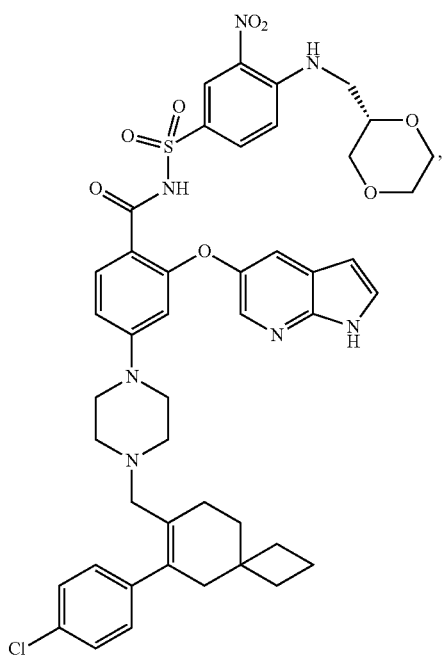 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

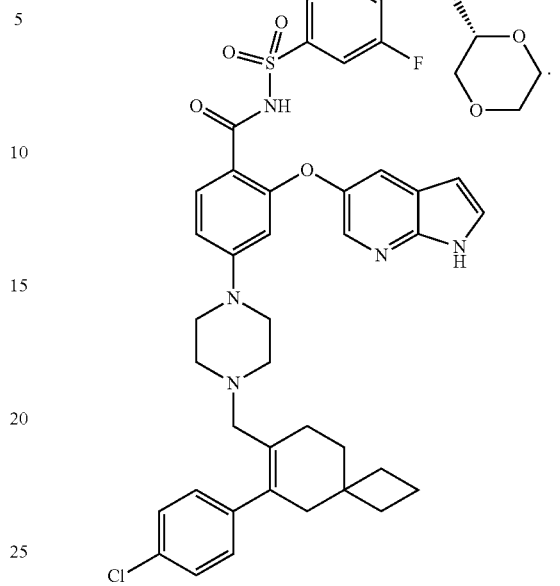

-continued

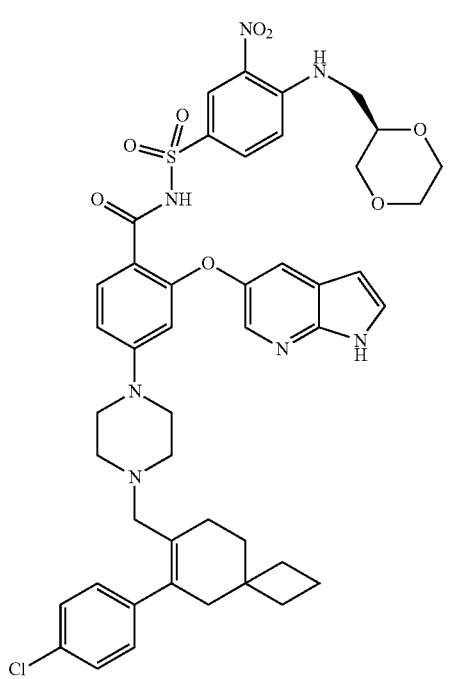

and

4. The method of claim 1, wherein the cancer is a solid tumor or a hematological cancer, wherein
the solid tumor is selected from adrenocortical carcinoma, anal cancer, astrocytoma, childhood cerebellar or cerebral, basal-cell carcinoma, bile duct cancer, bladder cancer, bone tumor, brain cancer, cerebellar astrocytoma, cerebral astrocytoma/malignant glioma, ependymoma, medulloblastoma, supratentorial primitive neuroectodermal tumors, visual pathway and hypothalamic glioma, breast cancer, Burkitt's lymphoma, cervical cancer, colon cancer, emphysema, endometrial cancer, esophageal cancer, Ewing's sarcoma, gastric cancer, glioma, head and neck cancer, heart cancer, Hodgkin lymphoma, islet cell carcinoma, Kaposi sarcoma, kidney cancer, laryngeal cancer, liver cancer, lung cancer, neuroblastoma, non-Hodgkin lymphoma, ovarian cancer, pancreatic cancer, gastro-intestinal cancer, pharyngeal cancer, prostate cancer, rectal cancer, retinoblastoma, Ewing family of tumors, skin cancer, stomach cancer, testicular cancer, throat cancer, thyroid cancer, cholangiocarcinoma, vaginal cancer, and small cell carcinoma, melanoma, cutaneous squamous cell carcinoma, glioblastoma, hysterocarcinoma, osteosarcoma, uterine cancer, uterine CS, colorectal cancer, sarcoma, chromophobe, renal cell carcinoma (RCC), clear cell RCC, papillary RCC, uveal melanoma, testicular germ cell, low grade glioma (LGG), mesothelioma, pheochromocytomas and paragangliomas (PCPG), and thymoma; and
the hematological cancer is selected from chronic lymphocytic leukemia (CLL), acute myeloid leukemia (AML), T-cell prolymphocytic leukemia, multiple myeloma (MM), Waldenstrom macroglobulinemia (WM), acute lymphoblastic leukemia (ALL), and lymphoma.

5. The method of claim 1, wherein the cancer is neuroendocrine cancer.

6. The method of claim 1, wherein the level of the at least one biomarker comprising Noxa and ASCL1 is measured by mRNA level, protein level or DNA level.

7. The method of claim 6, wherein the level of the at least one biomarker comprising Noxa and ASCL1 is measured by an amplification assay, a hybridization assay, a sequencing assay, or an immunoassay.

8. The method of claim 7, wherein the amplification assay is a polymerase-chain reaction (PCR)-based method.

9. The method of claim 1, wherein the predetermined threshold is set by statistical method, or is determined using classification algorithm.

10. The method of claim 1, wherein the predetermined threshold for Noxa is reached when the level of Noxa in the test sample is at least 15% higher than the corresponding reference level of Noxa.

11. The method of claim 10, wherein the reference level of Noxa is representative of an average level of Noxa in a general population of subjects having cancer.

12. A kit for use in the method of claim 1, comprising one or more reagents for measuring the level of at least one biomarker comprising Noxa.

* * * * *

UNITED STATES PATENT AND TRADEMARK OFFICE
CERTIFICATE OF CORRECTION

| | | |
|---|---|---|
| PATENT NO. | : 12,287,338 B2 | Page 1 of 5 |
| APPLICATION NO. | : 17/297188 | |
| DATED | : April 29, 2025 | |
| INVENTOR(S) | : Yifan Zhai et al. | |

It is certified that error appears in the above-identified patent and that said Letters Patent is hereby corrected as shown below:

In the Claims

At Column 180, Line 66, replace "or a Bcl-2 inhibitor to the subject-if the" with --or a Bcl-2 inhibitor if the--.

At Column 181, Line 40, replace " 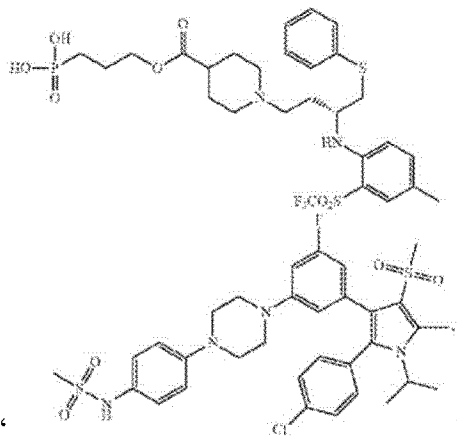 " with

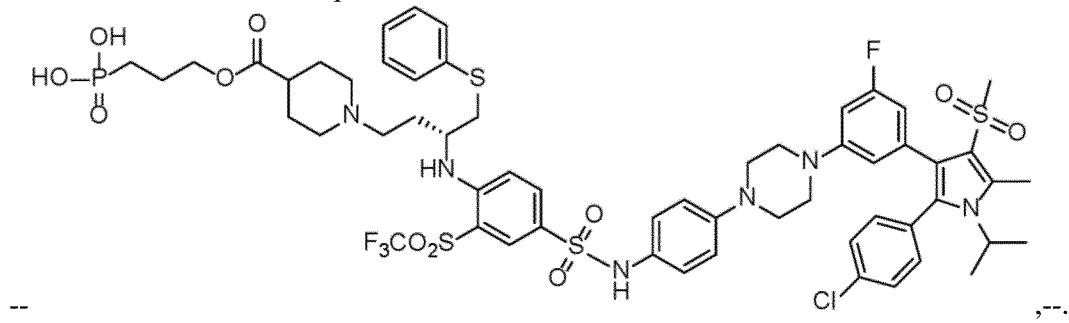

--,--.

Signed and Sealed this
Second Day of September, 2025

Coke Morgan Stewart
*Acting Director of the United States Patent and Trademark Office*

At Column 182, Line 5, replace " 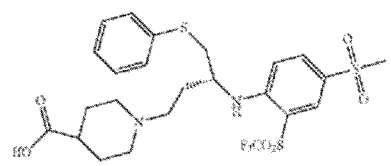 " with 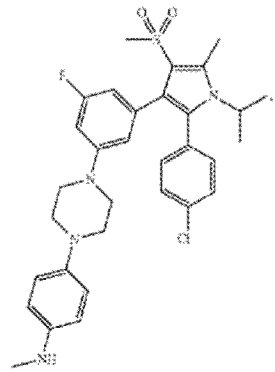 ,--.
At Column 184, Line 40, replace " 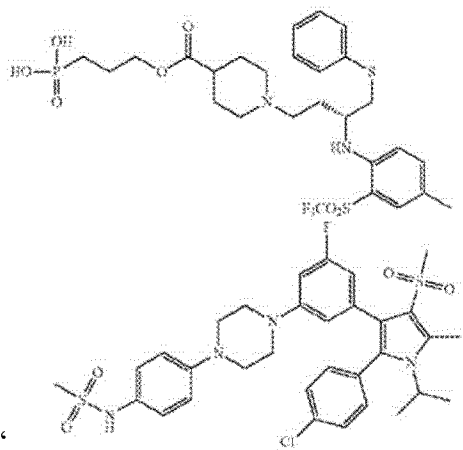 " with

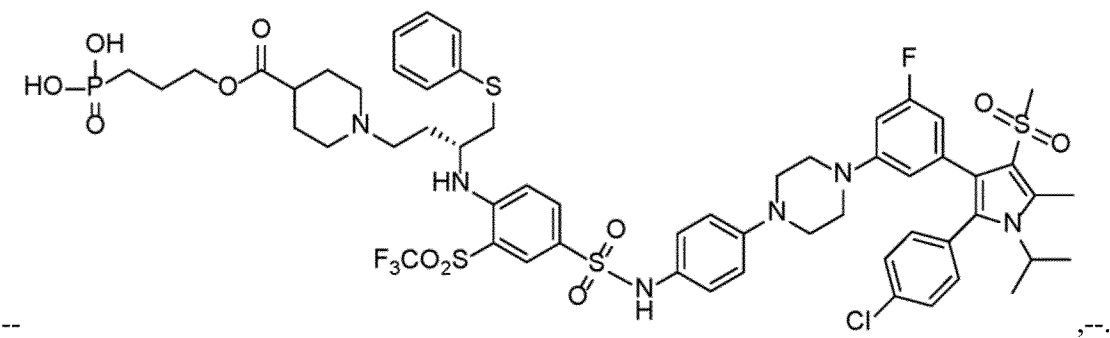
At Column 185, Line 5, replace " 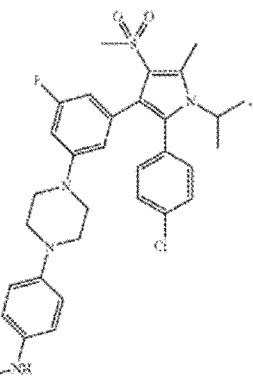 " with 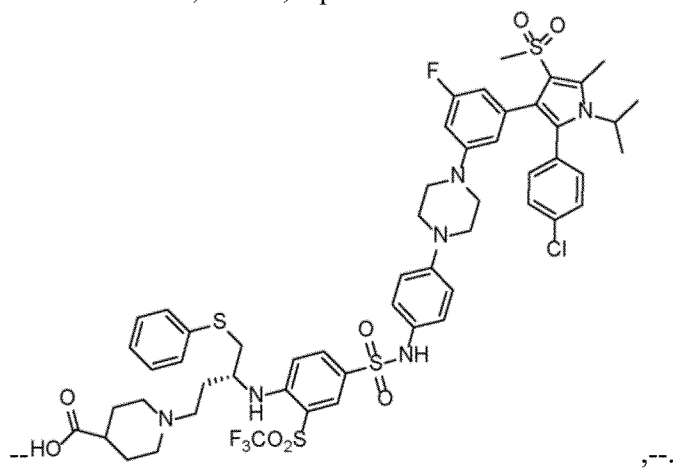
At Column 187, Line 20, replace "wherein;" with --wherein:--.
At Column 187, Line 54, replace "structure;" with --structure:--.

CERTIFICATE OF CORRECTION (continued)
U.S. Pat. No. 12,287,338 B2

From Column 187, Line 55 to Column 188, Line 14, replace " 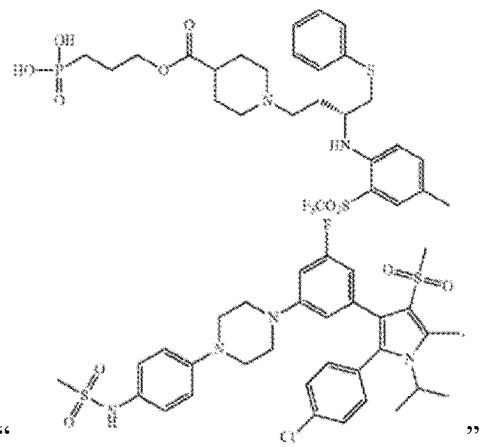 "

with -- 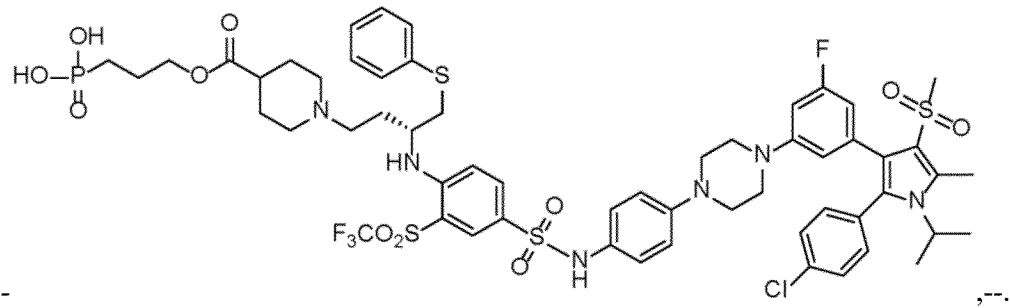 ,--.

At Column 188, Line 25, replace " 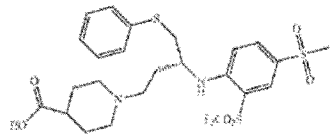 " with " 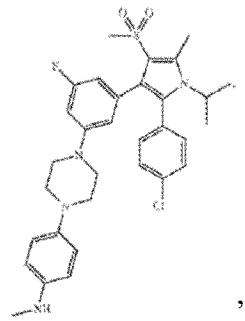 "

CERTIFICATE OF CORRECTION (continued)